(12) United States Patent
Etkin et al.

(10) Patent No.: US 12,115,383 B2
(45) Date of Patent: Oct. 15, 2024

(54) BRAIN STIMULATION TREATMENT IN DEPRESSION

(71) Applicants: The Board of Trustees of the Leland Stanford Junior University, Stanford, CA (US); The United States Government as Represented by the Department of Veterans Affairs, Washington, DC (US)

(72) Inventors: Amit Etkin, Stanford, CA (US); Corey Keller, Palo Alto, CA (US); Wei Wu, Palo Alto, CA (US)

(73) Assignees: THE BOARD OF TRUSTEES OF THE LELAND STANFORD JUNIOR UNIVERSITY, Palo Alto, CA (US); THE UNITED STATES GOVERNMENT AS REPRESENTED BY THE DEPARTMENT OF VETERANS AFFAIRS, Washington, DC (US)

( * ) Notice: Subject to any disclaimer, the term of this patent is extended or adjusted under 35 U.S.C. 154(b) by 0 days.

(21) Appl. No.: 17/703,639

(22) Filed: Mar. 24, 2022

(65) Prior Publication Data

US 2022/0280801 A1 Sep. 8, 2022

Related U.S. Application Data

(63) Continuation of application No. 16/095,661, filed as application No. PCT/US2017/029687 on Apr. 26, 2017, now Pat. No. 11,324,963.

(Continued)

(51) Int. Cl.
*A61N 2/00* (2006.01)
*A61B 5/00* (2006.01)

(Continued)

(52) U.S. Cl.
CPC .......... *A61N 2/006* (2013.01); *A61B 5/0075* (2013.01); *A61B 5/246* (2021.01); *A61B 5/372* (2021.01); *A61N 1/36025* (2013.01); *A61N 2/02* (2013.01)

(58) Field of Classification Search
CPC .......... A61N 2/00; A61N 2/002; A61N 2/004; A61N 2/006; A61N 2/008; A61N 2/02
See application file for complete search history.

(56) References Cited

U.S. PATENT DOCUMENTS 8,262,714 B2 9/2012 Hulvershorn et al.
2002/0007128 A1* 1/2002 Ives .................. A61N 2/02
600/15

(Continued)

FOREIGN PATENT DOCUMENTS

WO WO 2009/063435 * 5/2009 .............. A61N 2/02
WO 2013172981 A1 11/2013

OTHER PUBLICATIONS

International Search Report mailed on Jul. 26, 2017, for PCT/US2017/029687, filed on Apr. 26, 2017, 3 pages.

(Continued)

*Primary Examiner* — Carrie R Dorna
(74) *Attorney, Agent, or Firm* — Mintz, Levin, Cohn, Ferris, Glovsky and Popeo, P.C.

(57) ABSTRACT

Provided herein are, for example, systems and methods of diagnosing and treating depression, in which a transcranial magnetic stimulation (TMS) therapy is administered to a subject in need thereof and measuring a TMS evoked response in the subject, are provided. The systems and methods allow tailoring or optimizing of a treatment protocol for maximal individual benefit, thereby providing an individualized and optimized treatment protocol for psychiatric disorders such as depression.

22 Claims, 28 Drawing Sheets

Related U.S. Application Data

(60) Provisional application No. 62/459,814, filed on Feb. 16, 2017, provisional application No. 62/328,719, filed on Apr. 28, 2016.

(51) Int. Cl.
    *A61B 5/246*     (2021.01)
    *A61B 5/372*     (2021.01)
    *A61N 1/36*     (2006.01)
    *A61N 2/02*     (2006.01)

(56) References Cited

U.S. PATENT DOCUMENTS

| | | |
|---|---|---|
| 2005/0154426 A1 | 7/2005 | Boveja et al. |
| 2009/0024021 A1 | 1/2009 | George et al. |
| 2010/0113959 A1* | 5/2010 | Pascual-Leone ...... A61N 2/008 600/13 |
| 2010/0249577 A1 | 9/2010 | Schneider |
| 2011/0112427 A1 | 5/2011 | Phillips et al. |
| 2012/0101327 A1 | 4/2012 | Dissing et al. |
| 2013/0204330 A1 | 8/2013 | Schneider et al. |
| 2013/0281759 A1 | 10/2013 | Hagedorn et al. |
| 2013/0289433 A1 | 10/2013 | Jin et al. |
| 2013/0317281 A1 | 11/2013 | Schneider et al. |
| 2014/0058189 A1 | 2/2014 | Stubbeman |
| 2016/0220836 A1 | 8/2016 | Parks |

OTHER PUBLICATIONS

Written Opinion mailed on Jul. 26, 2017, for PCT/US2017/029687, filed on Apr. 26, 2017, 4 pages.
Ahdab et al. (Mar. 2010) "Comparison of "Standard" and "Navigated" Procedures of TMS Coil Positioning Over Motor, Premotor and Prefrontal Targets in Patients with Chronic Pain and Depression", Neurophysiologie Clinique, 40(1):27-36.
Andersson et al. (Oct. 2003) "How to Correct Susceptibility Distortions in Spin-echo Echo-planar Images Application to Diffusion Tensor Imaging", NeuroImage, 20(2):870-888.
Bakker et al. (Mar.-Apr. 2015) "rTMS of the Dorsomedial Prefrontal Cortex for Major Depression: Safety, Tolerability, Effectiveness, and Outcome Predictors for 10 Hz Versus Intermittent Theta-burst Stimulation", Brain Stimulation, 8(2):208-215.
Beam et al. (2009) "An Efficient and Accurate New Method for Locating the F3 Position for Prefrontal TMS Applications", Brain Stimulation, 2(1):50-54.
Benali et al. (Jan. 26, 2011) "Theta-burst Transcranial Magnetic Stimulation Alters Cortical Inhibition", The Journal of Neuroscience, 31(4):1193-2203.
Berlim et al. (2013) "Clinically Meaningful Efficacy and Acceptability Of Low-frequency Repetitive Transcranial Magnetic Stimulation (rTMS) For Treating Primary Major Depression: A Meta-analysis Of Randomized, Double-blind And Sham-controlled Trials", Neuropsychopharmacology, 38(4):543-551.
Blanchard et al. (1996) "Psychometric Properties of the PTSD Checklist (PCL)", Behaviour Research and Therapy, 34(8):669-673.
Bliss et al. (Jan. 7, 1993) "A synaptic model of memory: long-term potentiation in the hippocampus", Nature, 361(6407):31-39.
Burt et al. (Mar. 2002) "Neuropsychiatric Applications of Transcranial Magnetic Stimulation: a Meta-Analysis", The International Journal of Neuropsychopharmacology, 5(1):73-103.
Carpenter et al. (2012) "Transcranial Magnetic Stimulation (TMS) for Major Depression: a Multisite, Naturalistic, Observational Study of Acute Treatment Outcomes in Clinical Practice", Depression and Anxiety, 29(7):587-596.
Casarotto et al. (2010) "EEG Responses to TMS Are Sensitive to Changes in the Perturbation Parameters and Repeatable Over Time", Plos One, 5(4):e10281 (10 pages).
Chen et al. (Dec. 3, 2013) "Causal Interactions Between Fronto-Parietal Central Executive and Default-Mode Networks in Humans", Proceedings of the National Academy of Sciences of the United States of America, 110(49):19944-19949.
Chen et al. (Sep. 2013) "Hippocampal Network Connectivity and Activation Differentiates Post-Traumatic Stress Disorder from Generalized Anxiety Disorder", Neuropsychopharmacology, 38(10):1889-1898.
Chen et al. (2013) "Left Versus Right Repetitive Transcranial Magnetic Stimulation in Treating Major Depression: A Meta-analysis Of Randomised Controlled Trials", Psychiatry Research, 210(3):1260-1264.
Chung et al. (Nov.-Dec. 2015) "Measuring Brain Stimulation Induced Changes in Cortical Properties Using TMS-EEG", Brain Stimulation, 8(6):1010-1020.
Chung et al. (2015) "Theta-burst Stimulation: A New Form of TMS Treatment For Depression", Depress Anxiety, 32(3):182-192.
Cordes et al. (Aug. 2001) "Frequencies Contributing to Functional Connectivity in the Cerebral Cortex in "Resting-state" Data", American Journal of Neuroradiology, 22(7):1326-1333.
Daskalakis et al. (Nov. 2008) "Long-interval Cortical Inhibition from the Dorsolateral Prefrontal Cortex: A TMS-EEG Study", Neuropsychopharmacology, 33(12):2860-2869.
Eranti et al. (Jan. 2007) "A Randomized, Controlled Trial With 6-month Follow-up of Repetitive Transcranial Magnetic Stimulation and Electroconvulsive Therapy for Severe Depression", The American Journal of Psychiatry, 164(1):73-81.
Etkin et al. (2011) "Common Abnormalities and Disorder-Specific Compensation During Implicit Regulation of Emotional Processing in Generalized Anxiety and Major Depressive Disorders", The American journal of psychiatry, 168(9):968-978.
Etkin et al. (2009) "Disrupted Amygdalar Subregion Functional Connectivity and Evidence of a Compensatory Network in Generalized Anxiety Disorder", Archives of General Psychiatry, 66(12):1361-1372.
Etkin et al. (2010) "Failure of Anterior Cingulate Activation and Connectivity with the Amygdala During Implicit Regulation of Emotional Processing in Generalized Anxiety Disorder", The American Journal of Psychiatry, 167(5):545-554.
Faul et al. (May 2007) "G*power 3: A Flexible Statistical Power Analysis Program for the Social, Behavioral, and Biomedical Sciences", Behavior Research Methods, 39(2):175-191.
Fava et al. (Apr. 15, 2003) "Diagnosis and Definition of Treatment-resistant Depression", Biological Psychiatry, 53(8):649-659.
Feinberg et al. (Apr. 2013) "Ultra-fast MRI of the Human Brain with Simultaneous Multi-slice Imaging", Journal of Magnetic Resonance, 229:90-100.
First et al. (1996) "Structured Clinical Interview for the DSM-IV Axis I Disorders (SCID PTSD Module)", Research Version, Patient Edition.2002, New York: Biometrics Research, New York State Psychiatric Institute, 2 pages.
Fitzgerald et al. (Jan. 2009) "A Randomized Trial of rTMS Targeted with MRI Based Neuro-Navigation in Treatment-Resistant Depression", Neuropsychopharmacology, 34(5):1255-1262.
Fitzgerald et al. (Sep. 2009) "GABA and Cortical Inhibition in Motor and Non-Motor Regions Using Combined TMS-EEG: a Time Analysis", Clinical Neurophysiology, 120(9):1706-1710.
Fox et al. (Oct. 1, 2012) "Efficacy of Transcranial Magnetic Stimulation Targets for Depression is Related to Intrinsic Functional Connectivity with the Subgenual Cingulate", Biological Psychiatry, 72(7):595-603.
François et al. (Apr. 13, 2011) "Brainstorm: A user-friendly application for MEG/EEG analysis", Computational Intelligence and Neuroscience, 2011:879716 (13 pages).
Friston et al. (1995) "Spatial Registration and Normalization of Images", Human Brain Mapping, 2:165-189.
Friston et al. (1995) "Statistical Parametric Maps in Functional Imaging: A General Linear Approach", Human Brain Mapping, 2:189-210.
George et al. (May 2010) "Daily Left Prefrontal Transcranial Magnetic Stimulation Therapy for Major Depressive Disorder: A Sham-controlled Randomized Trial", Archives of General Psychiatry, 67(5):507-516.

(56) References Cited

OTHER PUBLICATIONS

George et al. (Oct. 2, 1995) "Daily Repetitive Transcranial Magnetic Stimulation (rTMS) Improves Mood in Depression", Neuroreport, 6(14):1853-1856.
George et al. (1994) "Prefrontal Cortex Dysfunction in Clinical Depression", Depression, 2(2):59-72.
George et al. (2013) "Treating the Depressions with Superficial Brain Stimulation Methods", Handbook of Clinical Neurology, 116:399-413.
Gershon et al. (2003) "Transcranial Magnetic Stimulation in the Treatment of Depression", The American Journal of Psychiatry, 160(5):835-845.
Glasser et al. (Jul. 20, 2016) "A Multi-modal Parcellation of Human Cerebral Cortex", Nature, 536(7615):171-178.
Glover et al. (Jul. 2000) "Image-based Method for Retrospective Correction of Physiological Motion Effects in fMRI: RETROICOR", Magnetic Resonance in Medicine, 44(1):162-167.
Grunhaus et al. (Feb. 15, 2003) "A Randomized Controlled Comparison of Electroconvulsive Therapy and Repetitive Transcranial Magnetic Stimulation in Severe and Resistant Nonpsychotic Major Depression", Biological Psychiatry, 53(4):324-331.
Hadley et al. (Mar. 2011) "Safety, Tolerability, and Effectiveness of High Doses of Adjunctive Daily Left Prefrontal Repetitive Transcranial Magnetic Stimulation for Treatment-resistant Depression in a Clinical Setting", The Journal of ECT, 27(1):18-25.
Hallett et al. (Jul. 19, 2007) "Transcranial Magnetic Stimulation: A Primer", Neuron, 55(2):187-199.
Hamilton M. (Feb. 1960) "A Rating Scale for Depression", Journal of neurology, neurosurgery, and psychiatry, 23(1):56-62.
Herbsman et al. (Sep. 2009) "More Lateral and Anterior Prefrontal Coil Location Is Associated with Better Repetitive Transcranial Magnetic Stimulation Antidepressant Response", Biological Psychiatry, 66(5):509-515.
Herwig et al. (Jul. 1, 2001) "Transcranial Magnetic Stimulation in Therapy Studies: Examination of the Reliability of "Standard" Coil Positioning by Neuronavigation", Biological Psychiatry, 50(1):58-61.
Hill et al. (May 2016) "TMS-EEG: A Window into The Neurophysiological Effects Of Transcranial Electrical Stimulation In Non-Motor Brain Regions", Neuroscience & Biobehavioral Reviews, 64:175-184.
Holland et al. (Mar. 2010) "Efficient Correction of Inhomogeneous Static Magnetic Field-induced Distortion in Echo Planar Imaging", Neuroimage, 50(1):175-183.
Holtzheimer et al. (2001) "A Meta-analysis of Repetitive Transcranial Magnetic Stimulation in the Treatment of Depression", Psychopharmacology Bulletin, 35(4):149-169.
Hoppenrath et al. (Mar. 30, 2016) "Intermittent Theta-Burst Transcranial Magnetic Stimulation Alters Electrical Properties of Fast-Spiking Neocortical Interneurons in an Age-Dependent Fashion", Frontiers in Neural Circuits, 10:22.
Ilmoniemi et al. (Jan. 2010) "Methodology for Combined TMS and EEG", Brain Topography, 22(4):233-248.
Insel et al. (Jul. 2010) "Research Domain Criteria (RDoC): Toward a New Classification Framework for Research on Mental Disorders", The American Journal of Psychiatry, 167(7):748-751.
Janicak et al. (Apr. 15, 2002) "Repetitive Transcranial Magnetic Stimulation Versus Electroconvulsive Therapy for Major Depression: Preliminary Results of a Randomized Trial", Biological Psychiatry, 51(8):659-667.
Kaiser et al. (Jun. 2015) "Large-Scale Network Dysfunction in Major Depressive Disorder: A Meta-analysis of Resting-State Functional Connectivity", JAMA Psychiatry, 72(6):603-611 (19 pages).
Keller et al. (Jun. 2, 2011) "Intrinsic Functional Architecture Predicts Electrically Evoked Responses in the Human Brain", Proceedings of the National Academy of Sciences of the United States of America, 108(25):10308-10313.
Keller et al. (Apr. 10, 2013) "Neurophysiological Investigation of Spontaneous Correlated and Anticorrelated Fluctuations of the BOLD Signal", The Journal of Neuroscience, 33(15):6333-6342.
Kim et al. (Oct. 2002) "Regularized Higher-Order In Vivo Shimming", Magnetic Resonance in Medicine, 48(4):715-722.
Klein et al. (Jul. 1, 2009) "Evaluation of 14 Nonlinear Deformation Algorithms Applied to Human Brain MRI Registration", Neuroimage, 46(3):786-802.
Koch et al. (2013) "Hebbian and Anti-Hebbian Spike-Timing-Dependent Plasticity of Human Cortico-Cortical Connections", The Journal of Neuroscience, 33(23):9725-9733.
Kozyrev et al. (Sep. 3, 2014) "Voltage-sensitive Dye Imaging of Transcranial Magnetic Stimulation-induced Intracortical Dynamics", Proceedings of the National Academy of Sciences of the United States of America, 111 (37) 13553-13558.
Kroenke et al. (2010) "The Patient Health Questionnaire Somatic, Anxiety, and Depressive Symptom Scales: a systematic review", General Hospital Psychiatry, 32(4):345-359.
Lisanby et al. (Jan. 2009) "Daily Left Prefrontal Repetitive Transcranial Magnetic Stimulation in the Acute Treatment of Major Depression: Clinical Predictors of Outcome in a Multisite, Randomized Controlled Clinical Trial", Neuropsychopharmacology, 34(2):522-534.
Liston et al. (Oct. 1, 2014) "Default Mode Network Mechanisms of Transcranial Magnetic Stimulation in Depression", Biological Psychiatry, 76(7):517-526.
Matsumoto et al. (Oct. 2004) "Functional Connectivity in Human Cortical Motor System: A Cortico-cortical Evoked Potential Study", Brain, 127(Pt 10):2316-2330.
Matsumoto et al. (2007) "Functional Connectivity in Human Cortical Motor System: A Cortico-cortical Evoked Potential Study", Brain, 130(Pt 1):181-197.
Mcnamara et al. (Oct. 2001) "Transcranial Magnetic Stimulation for Depression and Other Psychiatric Disorders", Psychological Medicine, 31(7):1141-1146.
Mosher et al. (Apr. 1999) "EEG and MEG: forward solutions for inverse methods", IEEE Transactions on Biomedical Engineering, 46(3):245-259.
Noda et al. (Dec. 2015) "Neurobiological Mechanisms of Repetitive Transcranial Magnetic Stimulation of the Dorsolateral Prefrontal Cortex in Depression: a Systematic Review", Psychological Medicine, 45(16):3411-3432.
O'Connor et al. (Jun. 2003) "Relative Effects of Repetitive Transcranial Magnetic Stimulation and Electroconvulsive Therapy on Mood and Memory: A Neurocognitive Risk-benefit Analysis", Cognitive and Behavioral Neurology, 16(2):118-27.
Opitz et al. (Feb. 15, 2016) "An Integrated Framework for Targeting Functional Networks via Transcranial Magnetic Stimulation", Neuroimage, 127:86-96.
P O'Reardon et al. (Dec. 1, 2007) "Efficacy and Safety of Transcranial Magnetic Stimulation in the Acute Treatment of Major Depression: A Multisite Randomized Controlled Trial", Biological Psychiatry, 62(11):1208-1216.
Posner et al. (Dec. 2011) "The Columbia-suicide Severity Rating Scale: Initial Validity and Internal Consistency Findings From Three Multisite Studies With Adolescents And Adults", The American Journal of Psychiatry, 168(12):1266-1277.
Privman et al. (Jun. 6, 2007) "Enhanced Category Tuning Revealed by Intracranial Electroencephalograms in High-order Human Visual Areas", The Journal of Neuroscience, 27(23):6234-6242.
Quartarone et al. (Apr. 2006) "Task-specific Hand Dystonia: Can Too Much Plasticity Be Bad for You?", Trends in Neurosciences, 29(4):192-199.
Rogasch et al. (Jul. 2013) "Assessing cortical network properties using TMS-EEG", Human Brain Mapping, 34(7):1652-1669.
Rogasch et al. (Nov. 1, 2014) "Removing Artefacts From TMS-EEG Recordings Using Independent Component Analysis: Importance for Assessing Prefrontal and Motor Cortex Network Properties", Neuroimage, 101:425-439.
Setsompop et al. (May 2012) "Blipped-controlled Aliasing in Parallel Imaging for Simultaneous Multislice Echo Planar Imaging with Reduced G-factor Penalty", Magnetic Resonance in Medicine, 67(5):1210-1224.
Skevington et al. (Apr. 2004) "The World Health Organization's WHOQOL-BREF Quality of Life Assessment: Psychometric properties and Results of the International Field Trial. A Report from the WHOQOL Group", Quality of Life Research, 13(2):299-310.

(56) References Cited

OTHER PUBLICATIONS

Slotema et al. (Mar. 2010) "Should We Expand the Toolbox of Psychiatric Treatment Methods to Include Repetitive Transcranial Magnetic Stimulation (rTMS)? A Meta-Analysis of the Efficacy of rTMS in Psychiatric Disorders", The Journal of Clinical Psychiatry, 71(7):873-884.
Smith et al. (2004) "Advances in Functional and Structural MR Image Analysis and Implementation as FSL", Neuroimage, 23(Suppl 1):S208-S219.
Thut et al. (Jan. 2010) "A Review of Combined TMS-EEG Studies to Characterize Lasting Effects of Repetitive TMS and Assess Their Usefulness in Cognitive and Clinical Neuroscience", Brain Topography, 22(4):219-232.
Valls-Solé et al. (Dec. 1992) "Human Motor Evoked Responses to Paired Transcranial Magnetic Stimuli", Electroencephalography and Clinical Neurophysiology, 85(6):355-364.
Watson et al. (Feb. 1995) "Testing A Tripartite Model: I. Evaluating the Convergent And Discriminant Validity Of Anxiety And Depression Symptom Scales", Journal of Abnormal Psychology, 104(1):3-14.
Watson et al. (Feb. 1995) "Testing A Tripartite Model: II. Exploring the Symptom Structure Of Anxiety And 20 Depression In Student, Adult, And Patient Samples", Journal of Abnormal Psychology, 104(1):15-25.
Winkler et al. (2011) "Automatic Classification of Artifactual ICA-Components for Artifact Removal in 1-3, 36-38, 71, 72 EEG Signals", Behavioral and Brain Functions, Online available: https://behavioralandbrainfunctions.biomedcentral.com/track/pdfil 0.1186/1744-9081-7-30?siterbehavioralandbrainfunctions.biomedcentral.com, 7:30 (15 pages).
Ziemann et al. (Jan. 2008) "Modifying Motor Learning Through Gating and Homeostatic Metaplasticity", Brain Stimulation, 1(1):60-66.

\* cited by examiner

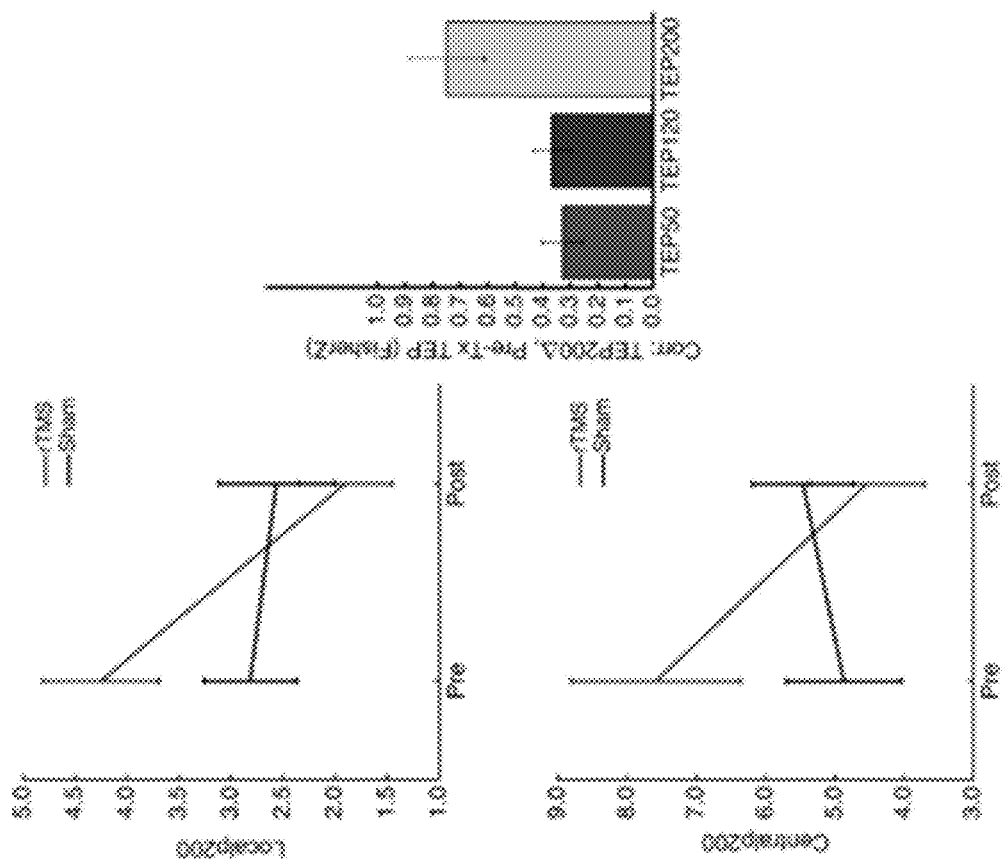

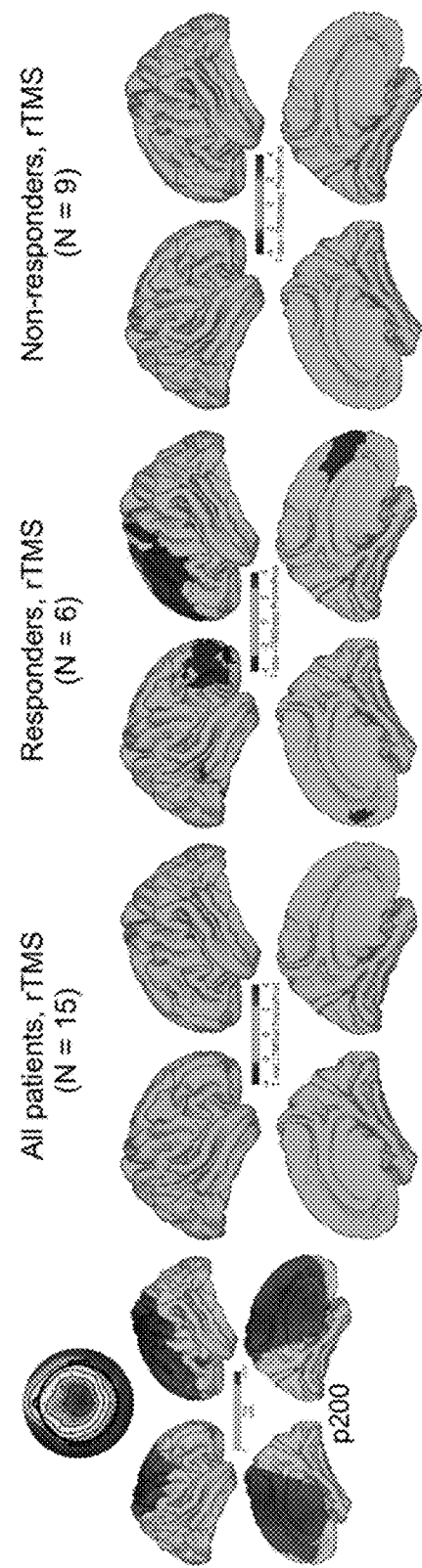

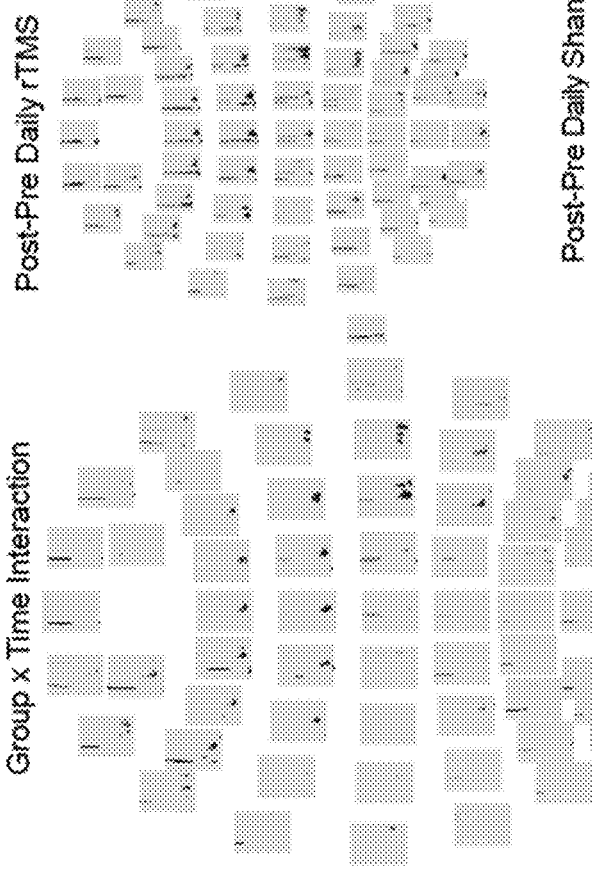
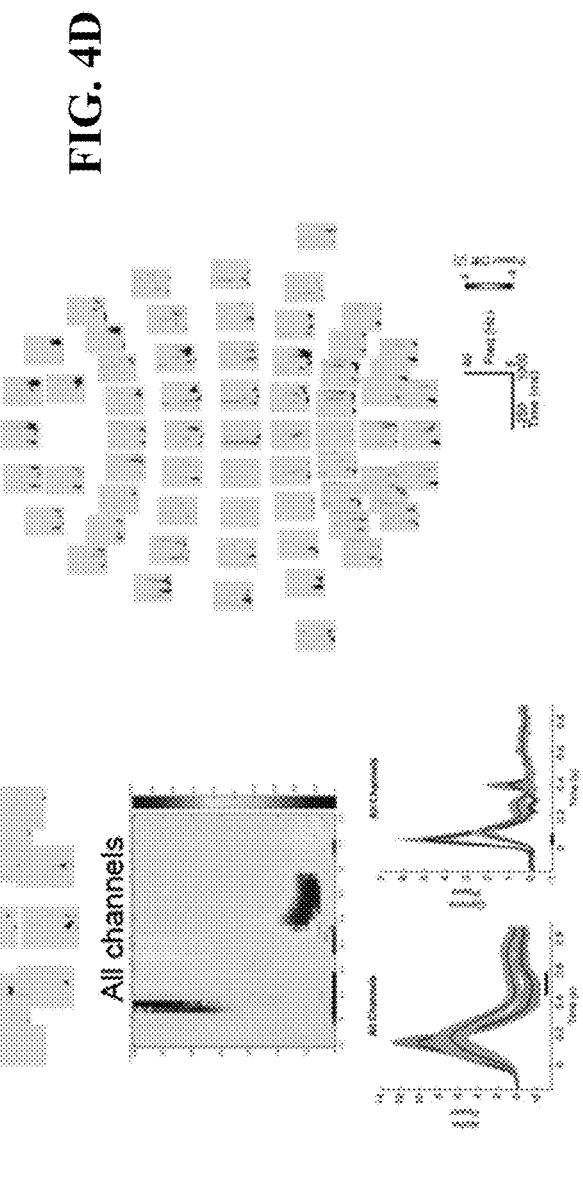
FIG. 4A  FIG. 4B  FIG. 4C  FIG. 4D

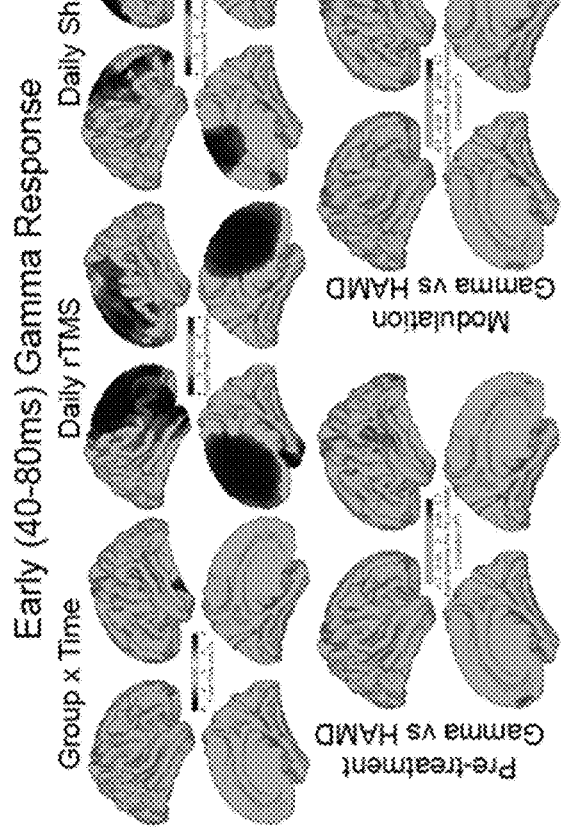
FIG. 4E
FIG. 4F
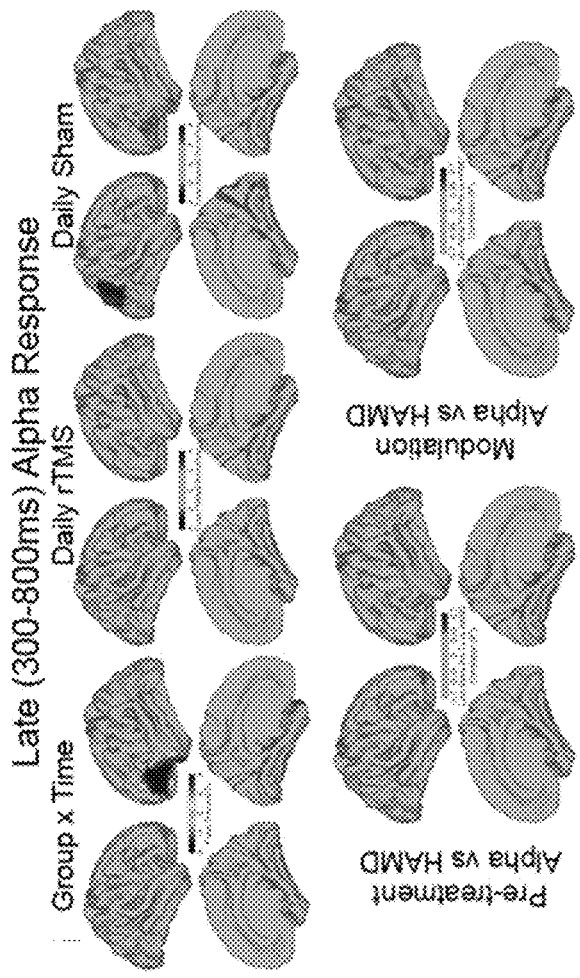
FIG. 4G
FIG. 4H

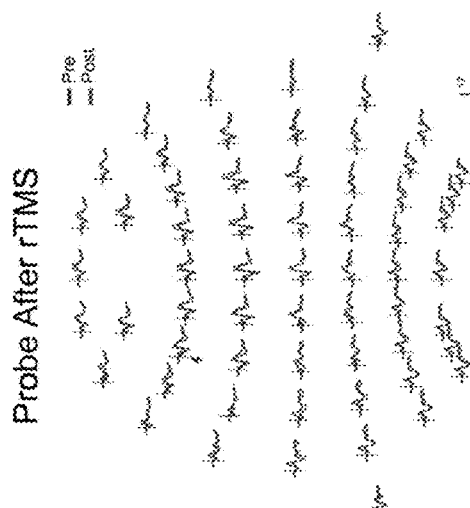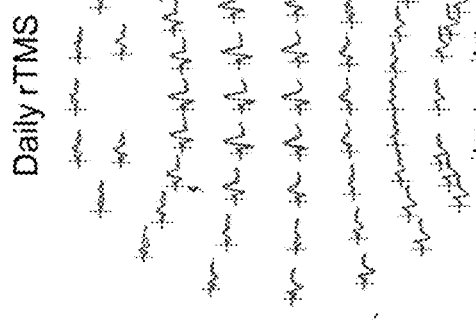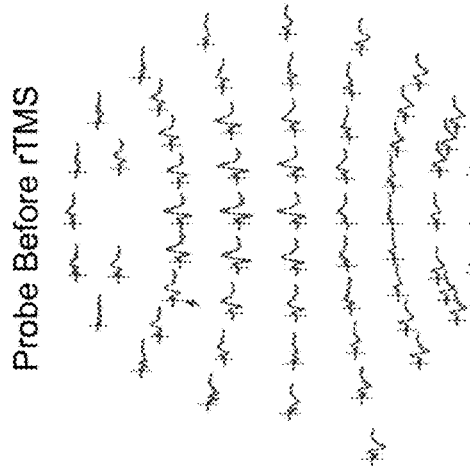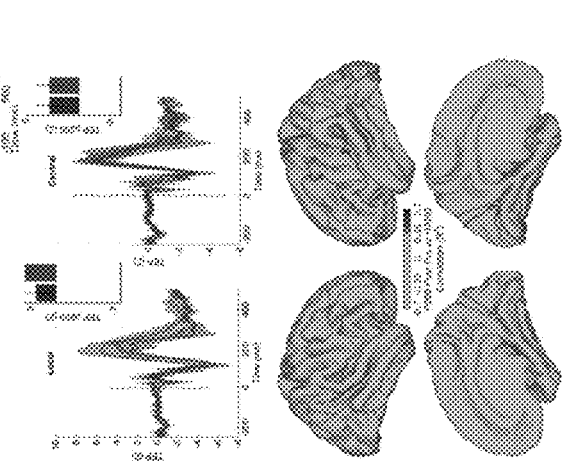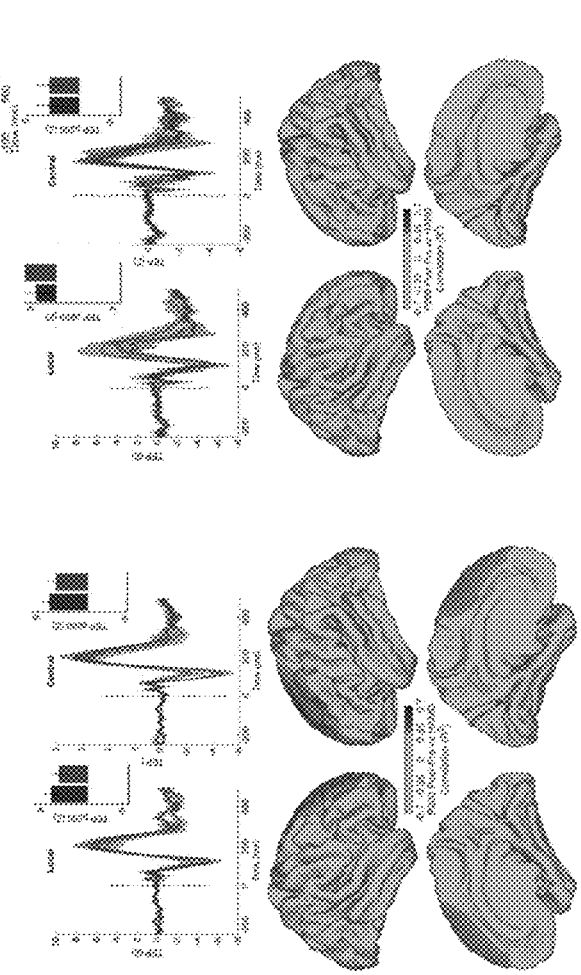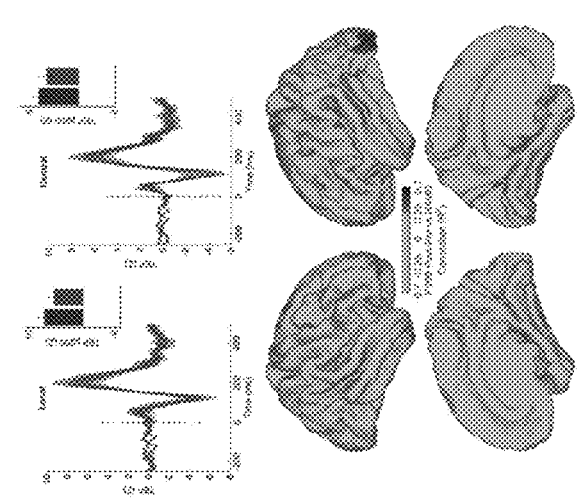
FIG. 5A  FIG. 5B  FIG. 5C

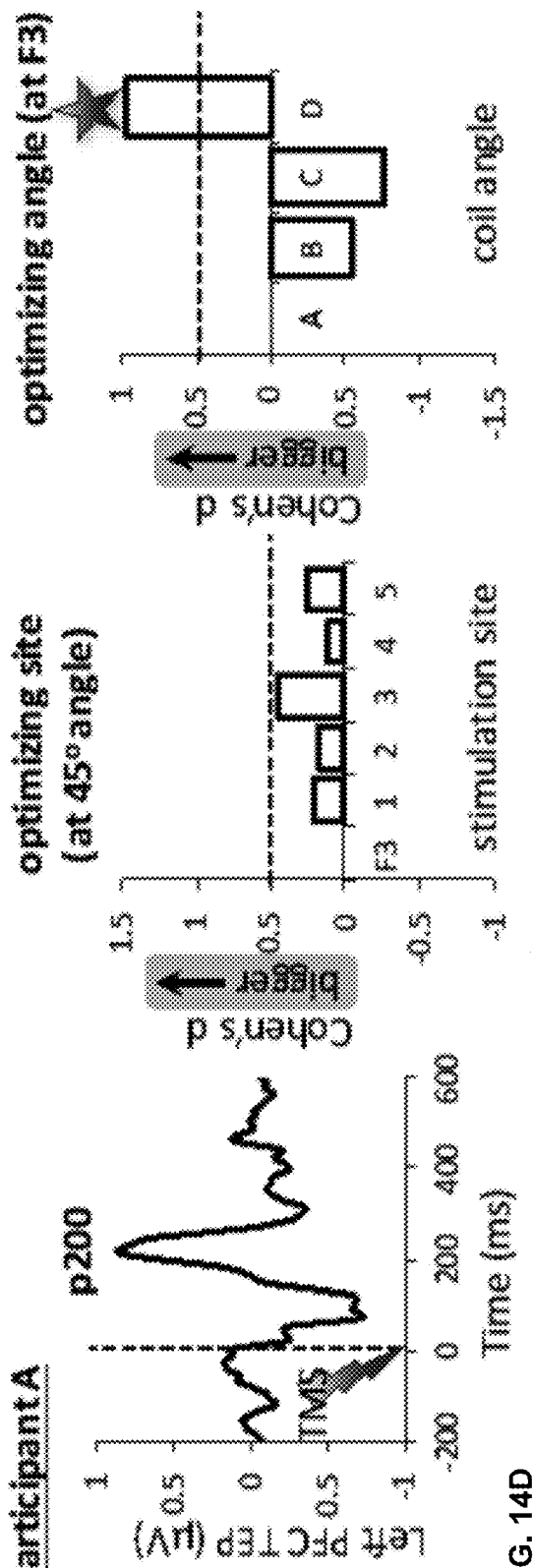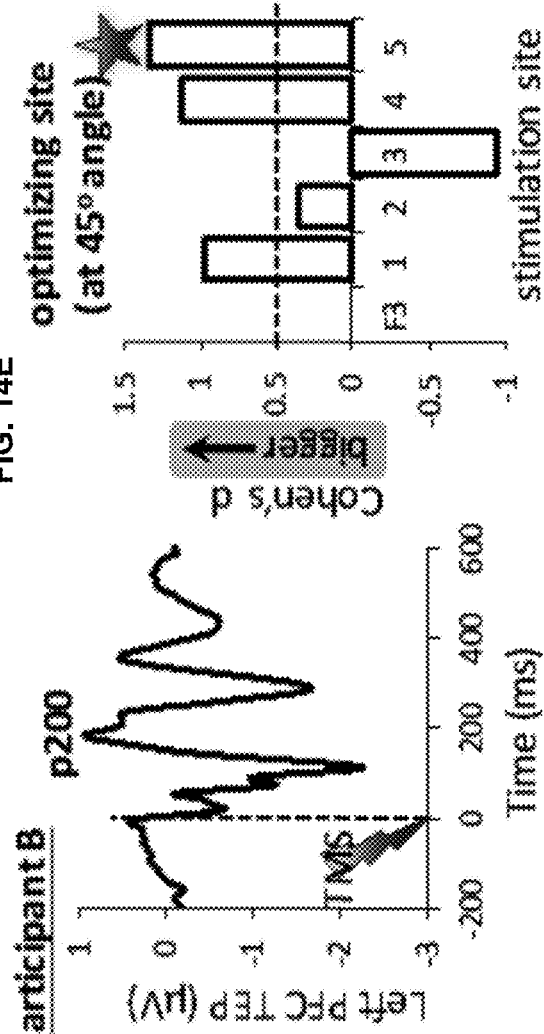
FIG. 14A FIG. 14B FIG. 14C
FIG. 14D FIG. 14E FIG. 14F

Responder<non-responder
(FDR p<.05 whole brain corrected)

BRAIN STIMULATION TREATMENT IN DEPRESSION

CROSS-REFERENCE TO RELATED APPLICATIONS

This application is a continuation of U.S. patent application Ser. No. 16/095,661 filed Oct. 22, 2018, now U.S. Pat. No. 11,324,963 issued May 10, 2022, which is a National Stage Entry of PCT/US2017/029687 filed Apr. 26, 2017, which claims priority to U.S. Provisional Application No. 62/459,814, filed Feb. 16, 2017 and U.S. Provisional Application No. 62/328,719, filed Apr. 28, 2016, the contents of which are incorporated herein in their entirety and for all purposes.

FIELD

The disclosures provided herewith relate, inter alia, to diagnosis and treatment of depression.

BACKGROUND

Depression is a highly prevalent and serious mental illness, with unsatisfying success rates for even the best-calibrated combination of pharmacotherapy and psychotherapy. Newer treatments such as transcranial magnetic stimulation (TMS) target specific brain networks and provide a promising non-invasive therapy for those who are medication-resistant or suffer intolerable side effects from antidepressants. However, the understanding of the mechanism by which TMS exerts its antidepressant effect is minimal. Furthermore, there is currently a need for a neural circuit biomarker to track and predict clinical outcome.

Up to 20% of the population struggles with depression over the course of their lives, making it the leading cause of years lost to disability worldwide and the third leading cause of death in adolescents and young adults. Antidepressant medications and psychotherapy have been the mainstay therapies for depression; however, 50% of treated patients fail to achieve remission after one year. Additionally, the last resort for patients is electroshock therapy (ECT) which, while highly effective, requires anesthesia, and often induces retrograde amnesia.

Accordingly, there is a need in the field to have more consistent and effective systems and method for diagnosis and treatment of depression. Provided herein are solutions for these and other problems in the art.

BRIEF SUMMARY

In a first aspect, there is provided a method for treating depression. The method includes administering transcranial magnetic stimulation (TMS) therapy to a subject in need thereof. The method further includes measuring a TMS evoked response in the subject. In some embodiments, the method for treating depression may include administering an effective amount of TMS therapy where the effective amount may be an amount of TMS therapy effective in treating depression.

BRIEF DESCRIPTION OF THE DRAWINGS

FIG. 1A) Schematic of TMS protocol for both active and sham arms. Each participant was assessed using spTMS/EEG prior to and after daily rTMS. Additionally, each participant received both active and sham probe rTMS sessions as part of the spTMS/EEG assessment, before and active treatment. FIG. 1B) The probe rTMS session assessed the acute effects of DLPFC rTMS on site of stimulation spTMS/EEG responses, using a short six-minute rTMS block (4 s on, 26 s off, 480 pulses). Daily rTMS consisted of twenty 37.5 minute sessions using the same stimulation regimen and delivering 3000 pulses. Each spTMS session was comprised of 60 suprathreshold spTMS pulses delivered with a jittered inter-pulse-interval of three seconds. Sham rTMS was performed by delivering electrical scalp stimulation concurrent with TMS pulses performed on an unmarked shielded face of a specially-designed active/placebo TMS coil.

FIGS. 2A-2F. Daily rTMS modulates the TMS-evoked potential. FIG. 2A) Distribution and strength of spTMS-evoked TMS-evoked potentials (TEPs) before and after daily rTMS. The lightning bolt denotes the approximate site of daily rTMS stimulation (which was guided by MRI-based neuronavigation). FIG. 2B) Pre- and post-treatment TEPs for both daily rTMS and daily sham arms at the electrodes near the site of stimulation (local) and centrally for daily rTMS and sham rTMS. FIG. 2C) Group x time interaction analysis for TEP200 responses. FIG. 2D) Correspondence between pre-treatment TEPs and change in the TEP200. For each patient, electrode, and time period, the mean correlation between the baseline TEP amplitude and the change in TEP200 was computed, averaged across electrodes, Z-transformed and averaged across subjects. FIG. 2E) Topography and source-localized map of the TEP200 potential for all patients prior to receiving rTMS treatment. FIG. 2F) Changes in the TEP200 induced by daily rTMS. Brain maps are group averaged comparisons for all patients receiving daily rTMS ('All Patients, rTMS)', patients that demonstrated a clinical response (>50% reduction in symptoms) to treatment ('Responders, rTMS)', and patients that did not respond to treatment ('Non-responders, rTMS)'. T-stats are thresholded at +/−2.13. *p<0.05.

FIG. 3A) Single channel comparison of pre-treatment TEP200 amplitude to clinical outcome. FIG. 3B) Bar graphs represent the data from A) stratified by treatment response. FIGS. 3C-3D) Correlation between clinical outcome and changes in TEP200 amplitude at single channels. FIGS. 3E-3F) Correlation between clinical outcome and pretreatment TEP200 magnitudes from source-localized regions of interest or change in TEP200 from these areas. FIG. 3G) Voxel-wise regression between baseline TEP200 TEP or change in TEP200 and clinical outcome. Warm-colored regions represent voxels with high correlation. *p<0.05; **p<0.01.

FIGS. 4A-4H. rTMS suppresses early frontal gamma power and increases later centrally-located alpha power. FIG. 4A) ERSP maps of group (rTMS/sham) x time (pre/post) interactions showing only significant effects. FIG. 4B) Top panel: ERSP interaction map across all channels. Note the gamma power decrease and alpha power increase. Bottom panel: Time course across all channels for alpha (left) and gamma (right) power for pre- (blue) and post- (red) daily rTMS. FIGS. 4C-4D) Effects of daily rTMS and sham on ERSP. Group ERSP difference maps for FIG. 4C) daily rTMS and FIG. 4D) daily sham treatment. Only significant time periods and frequencies are plotted. FIG. 4E) Effects of daily rTMS on early gamma power. Left panel: source localized group x time interaction analysis. Middle panel: Gamma power changes after daily rTMS treatment. Right panel: Gamma power changes after sham treatment. FIG. 4F) Voxel-wise correlation maps between early (40-80 milliseconds (msecs or ms)) gamma power and clinical outcome. Surface maps using pre-treatment early gamma power is on left, change in early gamma power after daily rTMS ('modulation gamma') is on right. Only voxels with strong correlation are shown. FIGS. 4G-4H) Same as E-F but for late (300 800 ms) alpha power.

FIGS. 5A-5C. Acute vs chronic effects of rTMS. FIGS. 5A-5C) Group TEP plots of spTMS response to the probe rTMS session (performed before and after daily rTMS) and spTMS response before/after daily treatment sessions. For each plot, blue and red waveforms denote TEPs before and after the session, respectively. Below are voxel-wise prediction of clinical outcome based on probe rTMS-induced changes in brain activity or daily rTMS-related changes. Colored voxels represent those whose source-localized change in TEP200 demonstrates strong correlation with clinical outcome.

FIG. 6A) Relationship of train number and GMFP. GMFP computed from the TEP200 timeframe of the last pulse in each train. FIG. 6B) Relationship of train number and regional MFP within the TEP200 potential across multiple brain regions. Error bars represent standard errors across subjects.

FIG. 7A) Group baseline TEP maps of healthy controls and patients with MDD. FIGS. 7B-7C) Pre- and post-probe TEP maps for MDD and healthy controls. Inset TEP figures show local and central TEP responses.

FIG. 9A) dlPFC rTMS normalizes DLPFC-medial FPC fMRI hyperconnectivity in depression, and FIG. 9B) reduces the p200 response to single spTMS/EEG pulses. FIG. 9C) Source localization shows that the spTMS/EEG p200 reduction occurred in the dlPFC and medial prefrontal cortex.

FIG. 11A) The more abnormally hyperconnected the dlPFC and medical PFC during resting state fMRI at baseline, the better the outcome of rTMS treatment. FIG. 11B) The larger the baseline dlPFC p200 TEP (shown as a median split), the better the outcome of rTMS treatment. FIG. 11C) p200 amplitudes are increased in depression and correlated with symptoms. FIG. 11D) The greater the decrease indlPFC p200 with rTMS, the greater the symptomatic improvement with treatment.

FIGS. 14A-14F. Data from two example participants for a site and angle optimization study. FIGS. 14A-14C) Participant A, left PFC TEP (µV), Cohen's d at 450 angle, and Cohen's d optimizing angle (at F3), respectively. FIGS. 14D-14F) Participant B, left PFC TEP (µV), Cohen's d at 450 angle, and Cohen's d optimizing angle (at F3), respectively. The dotted line is at the d=0.5 cutoff, and stars indicate optimized variation for that individual.

FIG. 15A) Overview of the TMS/EEG processing pipeline and ARTIST algorithm. FIG. 15B) Automated TMS/EEG artifact rejection with ARTIST results in TEP magnitudes that are nearly identical to manually-processed data. FIG. 15C) The TEP time course is likewise nearly identical between ARTIST and manual processing (shown is the global mean field power).

FIGS. 17A and 17B demonstrate the dlPFC resting connectivity before and after rTMS.

FIGS. 17A and 17B demonstrate the dlPFC resting connectivity before and after rTMS.

FIG. 19 demonstrates the resting connectivity data and its relationship with TMS/EEG data.

DETAILED DESCRIPTION OF CERTAIN EMBODIMENTS

Figure 1B:
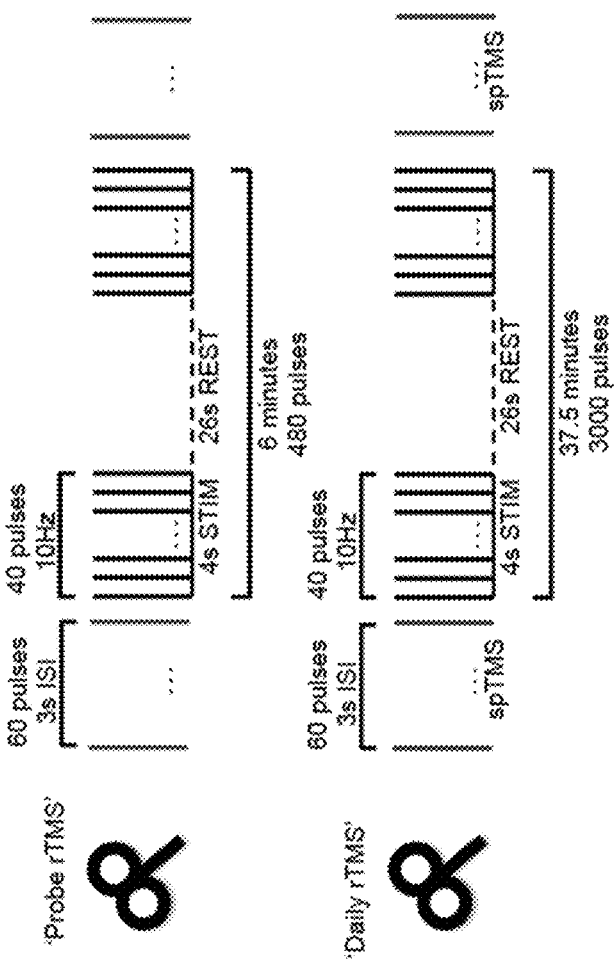
FIGS. 1A-1B. Experimental protocol.

In embodiments, the disclosures herewith provide, inter alia, systems and methods for the detection, diagnosis and identification of appropriate treatment protocol for depression. In embodiments, the methods provided herein utilize real time assessment of individual response to transcranial magnetic stimulation (TMS) and provide mechanisms to assess the efficacy of that treatment. In embodiments, the disclosures herewith provide feedback for TMS treatment, allowing for individualized alterations of treatment protocols and assessment of patient responsiveness.

Definitions

As used herein, the term "cognitive network" or "cognitive module" designates a grouping of cognitive regions or nodes that support associated cognitive processes. Example cognitive networks include the frontoparietal network (also called the executive control, central executive, or attentional network), the dorsal attention network (also called the visuospatial or spatial attention network), the salience network (also called the ventral attention or cingulo-opercular network) and the default mode network. Each cognitive network may comprise a number of cognitive nodes or cognitive regions, identifiable by, for example, independent component analysis (ICA).

As used herein, the term "cognitive region" or "cognitive node" is a continuous physical portion of the brain (e.g. cerebral cortex, hippocampus, thalamus or cerebellum) that supports a cognitive process. Cognitive regions may include, for example a gyrus, a sulcus or an area covering a collection of gyri or sulci. Cognitive regions may be grouped by associated function, activity, or connectivity into cognitive networks (also called cognitive modules).

As used herein, the term "connectivity" in relation to one or more cognitive regions refers to anatomical connectivity, functional connectivity, or causal connectivity between cognitive regions. Anatomical (or structural) connectivity includes intact structural links such as neuronal, synaptic or fiber pathways. Functional connectivity includes simultaneous or near simultaneous change in activity (e.g. less than 1 second when read via electrical stimulus, or on a time scale of several seconds when viewed by changes in blood flow, for example as analyzed by fMRI) between cognitive regions. The change in activity may be an increase or decrease from an average level activity. Functional connectivity, therefore, includes phasic relationships or waveform activity between cognitive regions. Causal connectivity is related to functional activity in that it is a response evoked in one region in response to stimulation of another region. Examples of methods of assaying neural activity include blood flow analysis (e.g. fMRI, or near infrared spectroscopy (NIRS)), functional connectivity analysis (e.g. electroencephalogram (EEG) or magnetoencephalography (MEG)), or structural connectivity analysis (e.g. diffusion-weighted structural connectivity analysis).

As used herein, the term "depression" may refer to a condition or disorder, which can range from being mild to severe, that negatively affects how people feel, the way they think and how they act. Depression may cause feelings of sadness and/or a loss of interest in activities once enjoyed. Depression symptoms can vary from mild to severe and can include: feeling sad or having a depressed mood, loss of interest or pleasure in activities once enjoyed, changes in appetite weight loss or gain unrelated to dieting, trouble sleeping or sleeping too much, loss of energy or increased fatigue, increase in purposeless physical activity (e.g., hand-wringing or pacing) or slowed movements and speech (actions observable by others), feeling worthless or guilty, difficulty thinking, concentrating or making decisions and thoughts of death or suicide.

"Treatment," "therapy," "treating," and "treat" are defined as acting upon a disease, disorder, or condition such as depression to reduce or ameliorate harmful or any other undesired effects of the disease, disorder, or condition and/or its symptoms. "Treatment," or "therapy" as used herein, covers the treatment of a subject in need thereof, and includes treatment of depression. "Treating," "treatment" or "therapy" of a condition or subject in need thereof refers to (1) taking steps to obtain beneficial or desired results, including clinical results such as the reduction of symptoms; (2) preventing the disease from reoccurring; (3) inhibiting the disease, for example, arresting or reducing the development of the disease or its clinical symptoms; (4) relieving the disease, for example, causing regression of the disease or its clinical symptoms; or (5) delaying the disease. In some embodiments, beneficial or desired clinical results include, but are not limited to, reduction and/or elimination of any symptoms related to depression with treatment as compared to the symptoms before or without the treatment.

As used herein, the term "a blood flow analysis" refers to any type of assays or tests that can detect changes in blood flow, for example, in any part or entire brain.

As used herein, the term "intracortical inhibition" may refer to the action of inhibitory neuronal processes within the cortex (e.g. inhibitory neural responses to stimulation). These may be assessed with a variety of procedures, such as short-interval intracortical inhibition (SICI) and long-interval intracortical inhibition (LICI), which are both assessed using pairs of TMS pulses delivered at different intervals. Short-interval intracortical inhibition may refer to paired pulses typically about <10 ms apart and long-interval intracortical inhibition may refer to paired pulses typically about 50-250 ms apart.

As used herein, the term "functional magnetic resonance imaging or functional MRI (fMRI)" refers to a functional neuroimaging procedure using MRI technology that measures brain activity by detecting changes associated with blood flow.

As used herein, the term "near-infrared spectroscopy (NIRS)" refers to a spectroscopic method that uses the near-infrared region of the electromagnetic spectrum (from about 700 nm to 2500 nm). For example, NIRS can be used for non-invasive assessment of brain function through the intact skull in human subjects by detecting changes in blood hemoglobin concentrations associated with neural activity, e.g., in branches of cognitive psychology.

As used herein, the term "electroencephalography (EEG)" refers to a neurological test that uses an electronic monitoring device to measure and record electrical activity in the brain.

As used herein, the term "magnetoencephalography (MEG)" refers to a non-invasive neurophysiological technique that measures the magnetic fields generated by neuronal activity of the brain. The spatial distributions of the magnetic fields are analyzed to localize the sources of the activity within the brain.

As used herein, the term "diffusion-weighted structural connectivity analysis" refers to an imaging method that uses the diffusion of water molecules to generate contrast in MR images. It allows the mapping of the diffusion process of molecules, e.g. water, in biological tissues, in vivo and non-invasively.

The signaling in a biological neural network is based on a highly coordinated system of electric charges, neurotransmitters and action potentials. The ability to reliably and non-invasively incite and monitor neuronal activity changes from outside the head with the purpose of modulating activity in specific neural networks remains a roadblock to enable advances in the detection, monitoring, and treatment of psychiatric, neurological and related conditions. A neural network can be considered as a complex electrical circuit made of many neurons connected through synapses formed between axons and dendrites. Both types of synapses, known as chemical and electrical synapses, respectively, transfer information between adjacent axons and dendrites directly or indirectly through electric field energy. Consequently, the neural network is sensitive to external electric fields. Existing non-invasive brain stimulation methods include transcranial magnetic stimulation (TMS), transcranial direct current stimulation (tDCS) and transcranial alternating current stimulation (tACS).

As used herein, the term "connectivity efficiency" refers to the degree of connectivity between two or more cognitive regions (e.g. 10 or more, 20 or more, or 30 or more cognitive regions). In one example, connectivity efficiency may be a measure of functional and/or anatomical connectivity. In another example, connectivity efficiency may approximate direct anatomical connectivity via synaptic connection. These different types of connectivity efficiency may be, but are not necessarily, interrelated. For example, closely correlated activity amongst two brain nodes may not be indicative of a direct anatomical connection.

Connectivity efficiency can be quantified by applying graph theory to measures of neural activity. Mathematical models derived from graph theory allow for calculation of metrics use to quantify connectivity efficiency including "global efficiency", "system segregation", "participation coefficient" and "closeness centrality".

The term "transcranial magnetic stimulation" or "TMS" as used herein refers to a non-invasive brain stimulation method which employs a magnetic field generator applied near or on the head to locally stimulate an electrical current within the brain. TMS is a non-invasive technique that typically involves placing a coil near or on the patient's head to depolarize or hyperpolarize neurons of the brain. In particular, TMS uses electromagnetic induction to induce neuronal electrical currents using a rapidly changing magnetic field. A changing magnetic field leads to changing electrical currents by causing transient shifts in ions across neuron cell membranes. The brain region underneath the TMS coil is the primary target for the TMS effect, with further distant areas of the brain being impacted through the initial impulse delivered to the targeted region under the coil. TMS techniques typically act on a volume of brain tissue that is approximately two to three centimeters in diameter. TMS treatment therefore refers to treatment or therapy providing brain stimulation via TMS to a patient in need of such treatment for a desired purpose, e.g. treatment of depression. TMS treatment, depending on the stimulation types, can include repetitive TMS (rTMS), single pulse TMS (spTMS), or paired pulse TMS (ppTMS). As described above, TMS provides one or more electric stimulation or pulse from a coil during a given time or per treatment (or therapy). If the number of TMS stimulation or pulse during the treatment or at any given time (e.g. several milliseconds to several minute or hours) is once, it is considered as a single pulse TMS. A paired pulse TMS can provide stimulation with two stimuli or pulses through a coil at a certain interval; the intensities of two stimuli or pulses can be identical or varied independently. Repetitive TMS (rTMS) comprises a plurality of stimuli or pulses generated from a coil per treatment or at a given time, each of the plurality of stimuli or pulses can be identical or different in their intensities. Also, a time interval between two stimuli or pulses in rTMS can be identical or different.

In embodiments, TMS treatment or TMS therapy, which terms are used herein interchangeably, includes administering transcranial magnetic stimulation, such as repetitive transcranial magnetic stimulation (rTMS). Treatment with rTMS includes multiple TMS administrations, typically in multiple sessions (either daily across days or multiple times per day and across days) wherein TMS is delivered repetitively in a pattern that is intended to induce plasticity (defined as a change in brain activity). This plasticity may increase or decrease the activity of the brain region that is targeted. In embodiments, the rTMS is a "high frequency" protocol, involving stimulation at >5 Hz. In embodiments the rTMS is a "low frequency" protocol, involving stimulation at ≤1 Hz. In embodiments the rTMS is a "theta burst" protocol, involving stimulation with either a continuous or intermittent theta burst pattern. In embodiments, the rTMS provides a protocol involving stimulations at any value from or at about 1 Hz to about 5 Hz. In embodiments, the rTMS provides a protocol involving stimulations having more than one frequency.

The term "frequency" in the context of TMS may refer to a rate at which one pulse of TMS occurs or is repeated over a particular period of time. For example, a frequency of TMS can vary, e.g. from about 1 to about 30 Hz or more. In some examples, a frequency of TMS may vary over a course of time so that a frequency of TMS at an early stage of treatment may be increased or decreased as the treatment continues. In some other examples, a frequency of TMS may substantially remain unchanged throughout a course of treatment.

The term "intensity" or "power" in the context of TMS may refer to an extent of an energy transferred per unit area. For example, a frequency of TMS can vary, e.g. from about 0.25 Hz to 100 Hz or more. In some examples, the intensity or power of TMS may vary over a course of time so that the intensity or power of TMS at an early stage of treatment may be increased or decreased as the treatment continues. In some other examples, the intensity or power of TMS may substantially remain unchanged throughout a course of treatment.

The term "duration" in the context of TMS may refer to a period of time which TMS continues per one protocol or a course of treatment. One or more number of TMS can be administered to a subject in duration from about a few seconds to about a minute, about a few minutes to about an hour, about one or more hours, about one day to several days, about one week to several weeks, about one month to several months or longer.

The term "waveform" in the context of TMS may refer to a curve showing the shape of a wave (or TMS pulse) at a given time. Some examples of TMS waveform include, but not limited to monophasic and biphasic. A waveform of TMS can vary or substantially remain unchanged throughout a course of treatment.

The term "pattern" in the context of TMS may refer to the temporal sequence of stimulation. Some examples of TMS pattern include, but not limited to fixed patterns at 1 Hz, clusters of stimuli at 10 Hz separated by a rest period, or theta burst. A pattern of TMS can vary or substantially remain unchanged throughout a course of treatment.

The terms "site" or "TMS site" in the context of TMS may refer to a location or area, relative to the head of a subject, where a stimulation is administered to the subject. In some examples where TMS is administered by placing a coil on the subject's head and TMS is generated by and administered from the coil, the site may include the location or area where the coil is placed as well as an angle of the coil relative to the head of the subject. In some examples, a site of TMS, e.g. a location and/or angle of a coil individually or in combination may vary over a course of time. In some other examples, the site of TMS, e.g. the location and/or angle of coil individually or in combination may substantially remain unchanged throughout a course of treatment.

In an example treatment protocol, daily rTMS induces long-lasting cortical neuromodulatory effects across broadly distributed regions. These effects are temporally and spatially removed from the onset and location of stimulation, but are highly predictive of clinical outcome. Mechanistically, non-invasive and invasive studies suggest that rTMS induces a reduction in early, local evoked gamma power and an early excitatory electrophysiological response, and an increase in later alpha power and slower inhibitory electrophysiological responses, suggesting a lasting alteration in the excitability of brain networks and altered interaction between brain regions and networks.

Treatment protocols for each type of TMS vary in duration, time course, pulse sequence, magnitude of stimulation and area of stimulation. Course of treatment can vary in duration from about one day, two days, three days, four days, five days, six days, seven days, one week, two weeks, three weeks, four weeks, five weeks, six weeks, seven weeks, eight weeks, or more. Frequency of TMS stimulation can vary (e.g., about 10, 20, or 30 Hz). TMS stimulation can be 1 Hz TMS, 3 Hz TMS, 5 Hz TMS, 7 Hz TMS, 10 Hz TMS, 15 Hz TMS, 20 Hz TMS, 25 Hz TMS, 30 Hz TMS or intermittent theta burst TMS. Paired pulse TMS can be administered at a time offset of about 10 milliseconds (msecs or ms), 20 msecs, 30 msecs, 40 msecs, 50 msecs, 100 msecs, 150 msecs, 200 msecs, 250 msecs, 300 msecs, or more. In embodiments, TMS can be administered to the right or left prefrontal cortices (e.g., left dorsolateral prefrontal cortex (DLPFC), right DLPFC, dorsal cingulate, dorsomedial prefrontal cortex, frontopolar cortex, ventrolateral prefrontal cortex.)

The term "biomarker" as used herein applies to a measure of a patient's biological functioning. In the present context a biomarker may be a pattern of neural functioning (e.g. a neural network connectivity or efficiency), an evoked response (e.g. a potential elicited by non-invasive brain stimulation), a pattern of behavioral or cognitive functioning (e.g. a performance on a memory deficit test), or a genetic or molecular marker or a combination of thereof.

The term "reduce", "decrease", "prolong" or "increase" is meant to alter negatively or positively, respectively, by at least 5%. An alteration may be by 5%, 10%, 25%, 30%, 50%, 75%, or even by 100%.

The terms "measurable", "notable", "substantial" or "substantially" are meant to refer to an perceptible alteration, variation or change. In some examples, a substantial alteration, variation or change can be, negatively or positively, respectively, by at least 1%, 2%, 3%, 4%, 5%, 10%, 25%, 30%, 50%, 75%, or even by 100% or more. In some other examples, a substantial alteration, variation or change can be about 2-fold, 3-fold, 4-fold, 5-fold, 10-fold, 20-fold, 30-fold, 50-fold, or 100-fold or more of difference.

A "subject" as used herein refers to an organism. In certain embodiments, the organism is an animal. In certain embodiments, the subject is a living organism. In certain embodiments, the subject is a cadaver organism. In certain preferred embodiments, the subject is a mammal, including, but not limited to, a human or non-human mammal. In certain embodiments, the subject is a domesticated mammal or a primate including a non-human primate. Examples of subjects include humans, monkeys, dogs, cats, mice, rats, cows, horses, goats, and sheep. A human subject may also be referred to as a patient.

A subject "suffering from or suspected of suffering from" a specific disease, condition, or syndrome has a sufficient number of risk factors or presents with a sufficient number or combination of signs or symptoms of the disease, condition, or syndrome such that a competent individual would diagnose or suspect that the subject was suffering from the disease, condition, or syndrome. Methods for identification of subjects suffering from or suspected of suffering from conditions associated with cancer is within the ability of those in the art. Subjects suffering from, and suspected of suffering from, a specific disease, condition, or syndrome are not necessarily two distinct groups.

As used herein, "susceptible to" or "prone to" or "predisposed to" a specific disease or condition and the like refers to an individual who based on genetic, environmental, health, and/or other risk factors is more likely to develop a disease or condition than the general population. An increase in likelihood of developing a disease may be an increase of about 10%, 20%, 50%, 100%, 150%, 200%, or more.

As used herein, the terms "treat," treating," "treatment," and the like refer to reducing or ameliorating a disorder and/or symptoms associated therewith. It will be appreciated that, although not precluded, treating a disorder or condition does not require that the disorder, condition or symptoms associated therewith be completely eliminated.

Ranges provided herein are understood to be shorthand for all of the values within the range.

Unless specifically stated or obvious from context, as used herein, the term "or" is understood to be inclusive.

Unless specifically stated or obvious from context, as used herein, the terms "a", "an", and "the" are understood to be singular or plural.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of various embodiments, suitable methods and materials are described below. Any published foreign patents and patent applications cited herein are incorporated herein by reference. Any other published references, documents, manuscripts and scientific literature cited herein are incorporated herein by reference. In the case of conflict, the present specification, including definitions, will control. In addition, the materials, methods, and examples are illustrative only and not intended to be limiting.

Non-Invasive Brain Stimulation

The signaling in a biological neural network is based on a highly coordinated system of electric charges, neurotransmitters and action potentials. The ability to reliably and non-invasively incite and monitor neuronal activity changes from outside the head with the purpose of modulating activity in specific neural networks remains a roadblock to enable advances in the detection, monitoring, and treatment of psychiatric, neurological and related conditions. A neural network can be considered as a complex electrical circuit made of many neurons connected through synapses formed between axons and dendrites. Both types of synapses, known as chemical and electrical synapses, respectively, transfer information between adjacent axons and dendrites directly or indirectly through electric field energy. Consequently, the neural network is sensitive to external electric fields. Existing non-invasive brain stimulation methods include transcranial magnetic stimulation (TMS), transcranial direct current stimulation (tDCS) and transcranial alternating current stimulation (tACS).

TMS is a non-invasive technique that typically involves placing a coil near the patient's head to depolarize or hyperpolarize neurons of the brain. In particular, TMS uses electromagnetic induction to induce neuronal electrical currents using a rapidly changing magnetic field. A changing magnetic field leads to changing electrical currents by causing transient shifts in ions across neuron cell membranes. The brain region underneath the TMS coil is the primary target for the TMS effect, with further distant areas of the brain being impacted through the initial impulse delivered to the targeted region under the coil. TMS techniques typically act on a volume of brain tissue that is approximately two to three centimeters in diameter. TMS methods can include repetitive TMS (rTMS), single pulse TMS (spTMS), or paired pulse TMS (ppTMS).

In embodiments, TMS therapy or treatment may include administering rTMS. In an example treatment protocol, daily rTMS induces long-lasting cortical neuromodulatory effects across broadly distributed regions. These effects are temporally and spatially removed from the onset and location of stimulation, but are highly predictive of clinical outcome. Mechanistically, non-invasive and invasive studies suggest that rTMS induces a reduction in early, local evoked gamma power and an early excitatory electrophysiological response, and an increase in later alpha power and slower inhibitory electrophysiological responses, suggesting a lasting alteration in the excitability of brain networks and altered interaction between brain regions and networks.

Treatment protocols for each type of TMS vary in duration, time course, pulse sequence, magnitude of stimulation and area of stimulation. Course of treatment can vary in duration from about one day, two days, three days, four days, five days, six days, seven days, one week, two weeks, three weeks, four weeks, five weeks, six weeks, seven weeks, eight weeks, or more. Frequency of TMS stimulation can vary (e.g., about 10, 20, or 30 Hz). TMS stimulation can be 1 Hz TMS, 3 Hz TMS, 5 Hz TMS, 7 Hz TMS, 10 Hz TMS, 15 Hz TMS, 20 Hz TMS, 25 Hz TMS, 30 Hz TMS or intermittent theta burst TMS. Paired pulse TMS can be administered at a time offset of about 10 milliseconds (msecs or ms), 20 msecs, 30 msecs, 40 msecs, 50 msecs, 100 msecs, 150 msecs, 200 msecs, 250 msecs, 300 msecs, or more. In embodiments, TMS can be administered to the right or left prefrontal cortices (e.g., left dorsolateral prefrontal cortex (DLPFC), right DLPFC, dorsal cingulate, dorsomedial prefrontal cortex, frontopolar cortex, ventrolateral prefrontal cortex)

Non-Invasive Brain Stimulation Evoked Response

Non-invasive brain stimulation (e.g., TMS) locally alters brain electrical signaling. These local alterations in signaling can result in broader alterations to neuronal signaling throughout the brain. These circuit-wide effects of non-invasive brain stimulation reflect the brain effects of stimulation as well as the network rebound response to a burst of activity entering the system. This set of events is referred to herein as a non-invasive brain stimulation evoked response (e.g., a TMS evoked response).

In embodiments, the disclosures herewith provide methods for assessing treatment progress or outcome via monitoring of the non-invasive brain stimulation evoked response (e.g., a TMS evoked response). In embodiments, non-invasive brain stimulation (e.g., TMS) evoked response can be measured via electroencephalogram (EEG), Magnetoencephalography (MEG), Functional magnetic resonance imaging (fMRI), or Near-infrared spectroscopy (NIRS). In embodiments, a magnitude of a non-invasive brain stimulation evoked response is measured at 25-50 msecs, 100-150 msecs, or 180 and 200 msec following non-invasive brain stimulation. The TMS evoked response can be measured between 25-50 msecs (p30), 30-70 msecs (p60), 70-120 msecs (n100), 150-250 msecs (p200). Alternatively, the TMS evoked response can be measured on the amplitude of oscillations at theta (5-8 Hz), alpha (8-12 Hz), beta (12-30 Hz), or gamma (30-60 Hz) within the first second after a TMS pulse.

The non-invasive brain stimulation evoked (e.g., a TMS evoked response) response can be monitored for one or more factors including frequency of TMS, duration of TMS (including, but not limited to, a number of sessions or pulses), TMS stimulation wave form, pattern of TMS, as well as the site(s) of TMS stimulation (or a TMS site). In embodiments, TMS treatment or therapy includes administering repetitive transcranial magnetic stimulation or rTMS.

TMS stimulation can be administered to a subject via a coil positioned on the head of the subject, e.g. a patient. It is observed that different coil angles can change or even reverse the direction of the induced brain response, and simulation and empirical evidence support the fact that the angle of the TMS coil relative to the head can make a substantial difference on the elicited brain response. In embodiments, a substantial difference on the elicited brain responses may include any notable changes in results indicative of or associated with brain responses. Such results may include, for example, those measured by methods of assaying neural activity include blood flow analysis (e.g. fMRI, or near infrared spectroscopy (NIRS)), functional connectivity analysis (e.g. electroencephalogram (EEG) or magnetoencephalography (MEG)), or structural connectivity analysis (e.g. diffusion-weighted structural connectivity analysis). If any results or readouts from one or more assays show any notable difference upon changing the site or angle of coil, it can be considered as generating a substantial difference in brain responses. The angle of the coil can be considered as the angle can determine or influence how induced current flows in brain tissue and interacts with underlying anatomy to determine the physiological processes influenced by TMS. Similarly, alterations in coil shape or design can change the way current flows within the coil and such changes in shape or design of coil can also be considered as part of the factors for TMS-evoked response. Thus, in embodiments, the site(s) of TMS stimulation can include the site and/or an angle of the coil relative to the head of the subject. Also, the shape and/or design of the coil can be changed and monitored for their effects on TMS stimulation to the patient.

Non-invasive brain stimulation (e.g., a TMS) treatment (therapy) may be modified based on variations to one or more of these factors of the non-invasive brain stimulation evoked response (e.g., a TMS evoked response). In embodiments, modifications to the treatment include changing a TMS site. In embodiments, modifications to the treatment include changing a site and/or an angle of the coil. In embodiments, modifications to the treatment include increasing a frequency of non-invasive brain stimulation (e.g., a TMS stimulation). In embodiments, modifications to the treatment (e.g. TMS treatment) include decreasing a frequency of non-invasive brain stimulation (e.g., TMS). In embodiments, modifications to the treatment (e.g. TMS treatment) include increasing intensity (e.g. a power) of non-invasive brain stimulation (e.g. TMS). In embodiments, modifications to the treatment include decreasing intensity (e.g. a power) of non-invasive brain stimulation. In embodiments, modifications to the treatment include increasing a treatment duration of non-invasive brain stimulation. In embodiments, modifications to the treatment include decreasing a treatment duration of non-invasive brain stimulation relative to a treatment used prior to the modification, e.g. from an originally planned treatment protocol. In embodiments, modifications to the treatment include changing a pattern of TMS such as intensity of individual pulse or time interval between pulses relative to a treatment used prior to the modification, e.g. from an originally planned pattern of TMS or any TMS that was previously administered to the patient. In embodiments, modifications to the treatment include terminating rTMS treatment.

Modifications to a treatment protocol may be enacted in real time via monitoring of the non-invasive brain stimulation evoked response, for a closed-loop individualized treatment. For example, a machine learning protocol, which can be a type of algorithm or computer program code and configured to identify and process transcranial magnetic stimulation electroencephalogram (TMS-EEG) data collected during a TMS treatment, may be adapted to analyze characteristics of a non-invasive brain stimulation evoked response and alter the treatment as it continues. In embodiments, modifications to treatment protocols occur in real time, at a following treatment session (e.g., within hours, within a single day, within days, within weeks). Furthermore, monitoring a non-invasive brain stimulation evoked response may occur following an initial course of treatment as a disease monitoring, prophylactic of diagnostic method. In embodiments, monitoring of a non-invasive brain stimulation evoked response may occur about one to four weeks, one month, two months, three months, 6 months, one year, or more following a successfully complete course of treatment.

Concurrent TMS/EEG

In embodiments, TMS stimulation (single or repetitive pulses) can be linked to EEG so that the recording of EEG is performed concurrently with TMS. In embodiments, TMS treatment or therapy includes administering repetitive transcranial magnetic stimulation or rTMS. EEG can provide a tool for registering rapid changes in neural activity at a millisecond time scale. TMS-evoked potentials (TEPs) can represent the average EEG response across stimulations, and can be characterized by a series of deflections, largely similar in timing across cortical stimulation sites, and highly test-retest reliable. The initial potentials (e.g. at 30 msecs; p30) may reflect the burst of excitatory activity seen in the cat cortex work above. This can be followed by potentials at, for example, about 60 msecs, 100 msecs and 200 msecs (p60, n100, p200) that at least partly reflect inhibition, likely related to the ~300 msecs inhibitory rebound in the cat cortex work. The concurrent spTMS/EEG can offer a window into the in vivo human brain by providing an opportunity to understand how TMS works at a neuronal temporal scale. It can also be a tool for assessing the neurophysiological impact of rTMS (which animal work suggests targets intracortical inhibition), and thus a direct pathway for individualization and optimization of rTMS treatment by determining how TMS methodological variations alter neurophysiological responses. Finally, because spTMS/EEG equipment and operation can be standardized for routine clinical use (unlike functional MRI), it can provide a path for yielding a clinic-friendly tool with near-term utility.

Individualization and Optimization of a Treatment Protocol

In embodiments, a method for treating depression can comprise administering a repetitive transcranial magnetic stimulation (rTMS) therapy to a subject in need thereof and measuring a TMS evoked response in the subject. In some embodiments, the method may include administering an effective amount of rTMS therapy wherein the effective amount may refer to an amount effective to treat depression. In embodiments, the method can further comprise, prior to the administering the rTMS therapy, measuring the brain activity of the subject, thereby obtaining a first data set of brain activity data. In embodiments, the method can further comprise, after said measuring the TMS evoked response, obtaining a second data set of the brain activity from the measured TMS evoked response. The brain activity data, at least in some embodiments, include brainwaves which are produced by electrical pulses from masses of neurons communicating with each other in a subject's brain. The first data set of brain activity data therefore may refer to natural brainwaves of the patient or before TMS treatment. The second data set of brain activity may refer to brainwaves generated in response to TMS treatment, which may indicate the patient's TMS evoked response. In embodiments, the method can further comprise determining a treatment protocol for the subject based on the first data set and the second data set. In embodiments, the TMS evoked response can be measured via EEG concurrently with or immediately after the rTMS therapy (TMS/EEG). In embodiments, TMS used in the concurrent TMS/EEG measurements can be spTMS. In embodiments, the method can further comprise removing one or more artifacts from data measured via TMS/EEG. In embodiments, one or more artifacts can be removed by using an automated artifact rejection algorithm. In embodiments, the determination of the treatment protocol can comprise adapting a treatment protocol such as any selections of types of TMS (e.g. use of single pulse TMS, paired-pulse TMS, repetitive TMS or any combinations thereof), a frequency of TMS, intensity of TMS, duration of TMS, a TMS wave form, a pattern of TMS, and/or a TMS site. In embodiments, the adaptation of a treatment protocol can comprise selection of a TMS protocol providing a measurable modulation of the TMS evoked response and/or selection of a TMS protocol, which causes a measurable difference between the first data set and the second data set. In embodiments, a substantial modulation of TMS evoked response may refer to any measurable modulation, alteration, variation or change in the brainwaves measured in the first data set and the second data set. For example, any noticeable changes in electrical potential (or brainwaves) recorded from the subject between the first data set and the second data set can be considered as substantial modulations. In particular, any changes in a pulse illustrating the recorded electrical potential, e.g. a pattern (or shape) of a pulse, a number of pulses measured in a given time, a pulse altitude and more can be considered. In some embodiments, a substantial difference between a first data set and a second data set may refer to any noticeable or measurable difference between the first data set and the second data set. In certain embodiments, a TMS therapy or treatment protocol can be adjusted in a manner such that the second data set shows substantial or most positive changes as compared to the first data set.

In embodiments, electroencephalogram (EEG) can be used to measure a brain's responses to one or more stimuli applied during TMS treatment. An EEG device can include a plurality of electrodes, which may be placed along the surface of the scalp and/or implanted beneath the scalp to record electrical activities within the brain. While TMS may be an effective diagnostic and treatment tool for various disorders (e.g., depression), EEG measurements of the brain's immediate responses to one or more TMS stimuli can provide real-time guidance during a TMS procedure. For example, TMS parameters such as stimulation duration, stimulation frequency, stimulation magnitude, stimulation area, time interval between stimuli, and/or the like can be adjusted in real time based on the brain's responses to one or more TMS stimuli. In embodiments, EEG data associated with TMS (henceforth TMS-EEG data) can include a variety of artifacts that can skew subsequent analysis of the data. For instance, TMS-EEG data can include artifacts arising from the TMS stimulus itself, subject motion (e.g., scalp muscle activation, eye blinks), coil clicks, coil recharge, and/or the like. As such, in some example embodiments, a TMS-EEG system can be configured to automatically reject artifacts from TMS-EEG data.

Automated artifact rejection can generate clean TMS-EEG data at sufficient speed for clean TMS-EEG data to be available during the TMS procedure. This clean TMS-EEG data can be used to adjust the protocol of the TMS treatment. For example, stimulation duration, stimulation frequency, stimulation magnitude, stimulation area, and/or time interval between stimuli may be changed, in real-time, based on the clean TMS-EEG data generated through automated artifact rejection.

In embodiments, a TMS-EEG system can be configured to administer one or more types of TMS procedures such as single-pulse TMS (spTMS), paired-pulse TMS (ppTMS), repetitive TMS (rTMS), and/or the like. In embodiments, TMS treatment or therapy includes administering repetitive transcranial magnetic stimulation or rTMS. Moreover, the TMS-EEG system can be configured to collect, during a TMS treatment, corresponding TMS-EEG data indicative of a subject's responses to the TMS stimuli that is being administered to the subject. According to some example embodiments, the TMS-EEG system can perform automated artifact rejection to remove, from the TMS-EEG data, artifacts originating from a variety of artifactual sources including, for example, the TMS stimuli, subject motion (e.g., scalp muscle activation, eye blinks), coil clicks, coil recharge, and/or the like. In order to remove artifacts from TMS-EEG data, the TMS-EEG system can decompose TMS-EEG data, which can be preprocessed (e.g., to remove TMS stimulation and/or spectrally irrelevant artifacts), into a plurality of independent components (ICs) and apply machine learning protocol (e.g., a classifier such as a Fisher linear discriminant analysis (FLDA) classifier and/or the like) trained to identify one or more artifactual ICs. In some embodiments, the resulting clean TMS-EEG data can be used to provide real-time guidance during a TMS procedure. For instance, the TMS-EEG system can perform, based on the clean TMS-EEG data, real-time adjustments to one or more treatment protocols such as treatment duration, stimulation frequency, stimulation magnitude, stimulation area, time interval between stimuli, and/or the like.

In embodiments, measurement of a non-invased brain stimulation evoked response provides real time predictability of the efficacy of a treatment protocol in the treatment of depression. In embodiments, the systems and methods of the disclosures herewith may be particularly valuable in the tailoring or optimizing of a treatment protocol for maximal individual benefit, thereby providing an individualized and optimized treatment protocol for psychiatric disorders such as depression.

EXAMPLES

The inventors hypothesized that 10 Hz rTMS induces long-lasting plasticity within the stimulated network, and that the strength of neuromodulatory effects in turn predict clinical outcome. This was tested by conducting a double blind, sham-controlled, randomized clinical trial for patients undergoing rTMS treatment for major depressive disorder. By combining TMS-EEG and daily rTMS treatment, it was possible to directly measure networks modulated by a single session and daily rTMS treatments. A consistent neuromodulatory effect of rTMS was found in the late TMS-evoked potential located across pre-frontal cortices, and the degree of suppression was highly predictive of clinical outcome. This biomarker can be used to stratify based on predicted clinical outcome as well as be the target of novel stimulation protocols that maximize this neuromodulatory effect.

Example 1: Materials and Methods

Participants. 33 patients (17 female, age mean/SD 32.9/8.0 years) and 15 demographically similar healthy control subjects (7 female, age mean/SD 34.0/10.4 years) gave informed consent to participate in this study, which was approved by Stanford University Institutional Review Board. All participants were 18-50 years old, right handed, and met criteria for DSM-IV defined major depression. Subjects were either medication-free or tapered off of their medications ≥2 weeks prior to therapy initiation. In order to limit placebo response rates that can diminish sham-real rTMS comparisons, but not enrich for an excessively treatment-resistant population (21), inclusion study required one failed adequate trial of an antidepressant within-episode or treatment intolerance or not wanting psychopharmacological treatment (22), but not >3 treatment failures. Exclusion criteria included contraindications for MRIs (e.g. implanted metal), history of head trauma with loss of consciousness, history of seizures, neurological or uncontrolled medical disease, active substance abuse, and psychotic or bipolar disorders, as well as prior history of ECT or rTMS failure. Depressive symptoms were assessed in patients using both the Hamilton Depression Rating Scale (HAMD) and the Montgomery Asberg Depression Rating Scale (MADRS) before treatment initiation (day 1), at the midpoint (day 10), and at the end of treatment (day 20). Responders were characterized by those with a >50% reduction in depressive symptoms at the end of treatment.

Transcranial Magnetic Stimulation and Research Sessions. Patients were randomized to active or sham rTMS treatment in a double-blind sham-controlled design. Briefly, a computer-generated code determined whether a patient would receive active or sham rTMS. For both active and sham treatment, in order to maximize the validity of the double-blind sham-controlled design, both 1) a direction-sensor TMS coil alerted the operators to flip the coil over if the wrong side is being used, and 2) electrodes placed under the coil were activated with low-intensity electrical stimulation applied to the scalp for sham and placed but not activated in the active treatment arm. This electrical stimulation sham method has been successfully implemented and validated in a recent multi-site TMS treatment study (27). For both treatment arms, the TMS coil was placed above the left DLPFC as localized by independent component analysis from a resting-state functional magnetic resonance imaging dataset in a separate cohort, which corresponds roughly to the '5 cm rule' but is tied to a functional network (executive control network) rather than a distance measure, especially as ~⅓ of patients treated with the "5 cm rule" typically do not receive stimulation in the DLPFC (29).

Figure 1A:
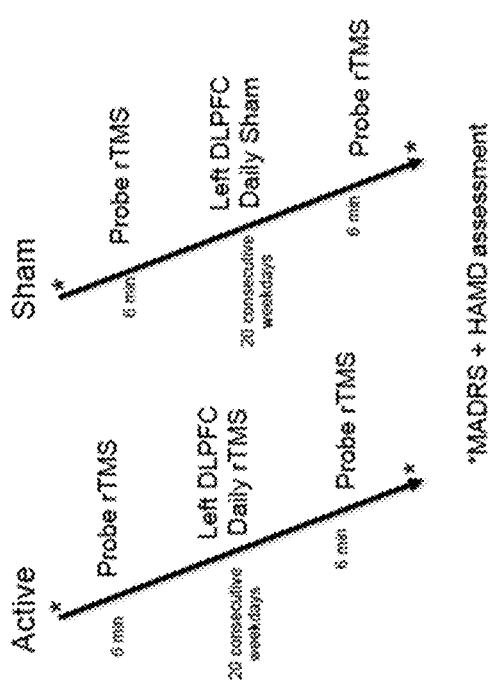

Those randomized to active rTMS treatment received daily left DLPFC rTMS treatments consisted 4 s trains of 10 Hz followed by 26 s rest (28), applied over 37.5 minutes (3000 total pulses) per day (FIG. 1). Stimulation was applied at 120% of each subject's resting motor threshold. This protocol is similar to effective rTMS treatment protocols (27), but extends beyond it by delivering more pulses within the same amount of time, which has proven both tolerable and highly effective (28). Patients received 4 weeks of daily treatment, followed by a HAMD depression assessment. Those patients with <25% change in HAMD scores from baseline exited the active rTMS treatment arm and proceed to follow-up with a TMS-EEG session, while those with >25% change can receive another 2 weeks of daily treatment in order to maximize response before undergoing the follow-up TMS-EEG session.

TMS-EEG acquisition. EEG data were recorded using a TMS-compatible 64-channel amplifier (ANT Neuro, Inc.), which has a large dynamic range to avoid saturation by the TMS pulse, using a system with small Ag/AgCl electrodes and active shielding. The impedances at all electrodes were kept below 5 kOhm and sampled at 5 kHz to minimize the stimulation artifact. The nose tip was used as the reference. To alleviate contamination of the EEG data by auditory potentials evoked by the TMS discharge clicks, subjects wore earplugs playing continuous masking noise mimicking the click sound. A thin pad was placed between the coil and electrodes to minimize TMS-induced vibratory noise. The TMS recharge artifact was avoided by delaying recharge. Electrode positions on the scalp were marked using the Visor2 neuronavigation system.

The recorded EEG data were analyzed offline using a custom script pipeline developed in MATLAB®. The pipeline consists of three stages: 1) artifact rejection: in addition to typical EEG artifacts (e.g. eye movements and EKG), the EEG data were also contaminated by the TMS pulse artifact, and TMS-induced scalp muscle artifacts. Since the pulse artifact was short lasting (<10 msecs), the affected data were discarded. All the other artifacts were effectively removed via a semi-automatic method based on independent component analysis (J. C. Mosher, R. M. Leahy, and P. S. Lewis, "EEG and MEG: Forward solutions for inverse methods," IEEE Trans. Biomed. Eng., vol. 46, pp. 245-259, 1999; Tadel F, Baillet S, Mosher J C, Pantazis D, Leahy R M, "Brainstorm: A User-Friendly Application for MEG/EEG Analysis," Computational Intelligence and Neuroscience, vol. 2011, Article ID 879716, 13 pages, 2011). 2) Source reconstruction: To alleviate volume conduction, the weighted minimum norm estimation (WMNE) algorithm was employed to estimate cortical source activity. To ensure the accuracy of source localization, we integrated the subjects' own anatomical MRI scans and electrode positions when building the forward model, which we accomplish through Brainstorm (e.g., at website neuroimage.usc.edu/brainstorm/). For the purpose of the group analysis, we projected the individual subject's source activity onto a standard source space using a Freesurfer parcellation, as known in the art. 3) Spatio-temporal-spectral analyses: All spatio-temporal-spectral analyses were performed in both the channel and source spaces. We quantified the temporal dynamics of brain responses by TMS-evoked potentials (TEPs), which are the average of the EEG signals across trials. The global mean-field power (GMFP) was obtained by averaging the TEP power across channels. The event-related spectral perturbation (ERSP) was calculated by using the wavelet transform with a −400 to −100 msecs pre-TMS baseline in each trial.

Intratrain-rTMS analysis. The ability to record changes in brain activity during, as opposed to, following treatment offers many benefits, including real-time monitoring and the potential for closed-loop approaches. Furthermore, understanding the dynamic changes in brain activity prior to treatment onset would provide insight into the degree of plasticity that can be induced by the current treatment regimen. To this end, the EEG activity during the probe rTMS period was recorded both before and after daily rTMS. Details of the EEG setup were identical to other components of the experiment. The focus on the test includes analysis on the TEP200, i.e. an EEG deflection in the p200 (200 msecs pulse) component, which is also referred to as p200 response or simply p200) based on results from the pre/post experiments described here. For each train of 10 Hz pulses during the probe period, the evoked response to the last pulse in the train was quantified, as the inter-pulse interval restricted analysis to potentials <100 msecs. Following a baseline correction, at each electrode the strength of TEP200 was quantified following the last pulse in each train. GMFP and regional MFP (described above) were then quantified, and a linear regression of the relationship of train number and MFP calculations were performed.

Figure 2A:
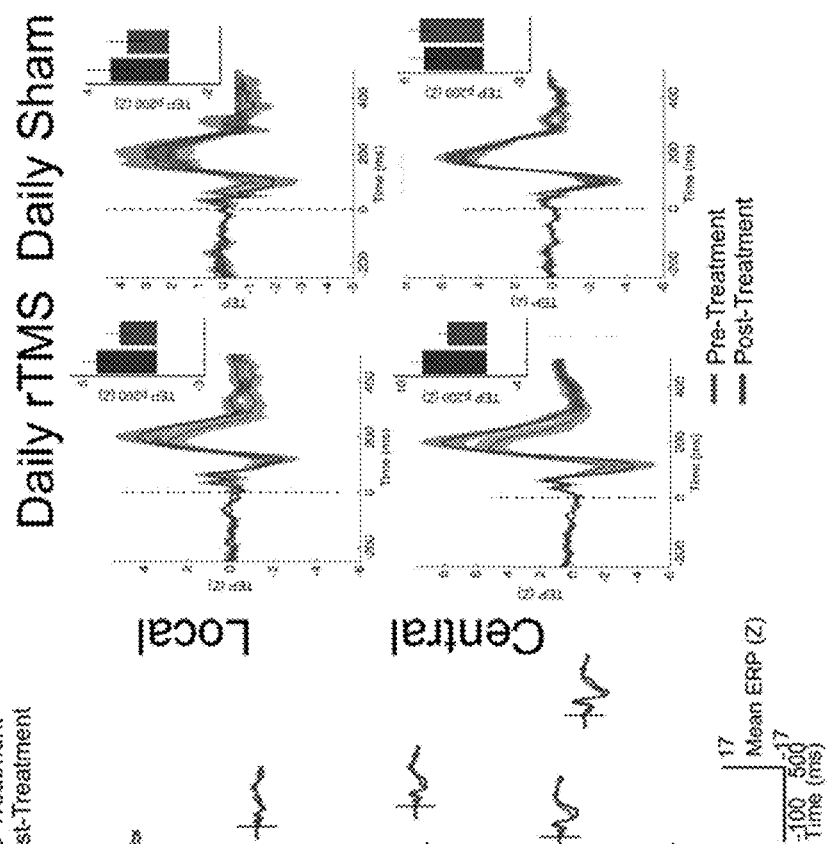
Figure 2B:
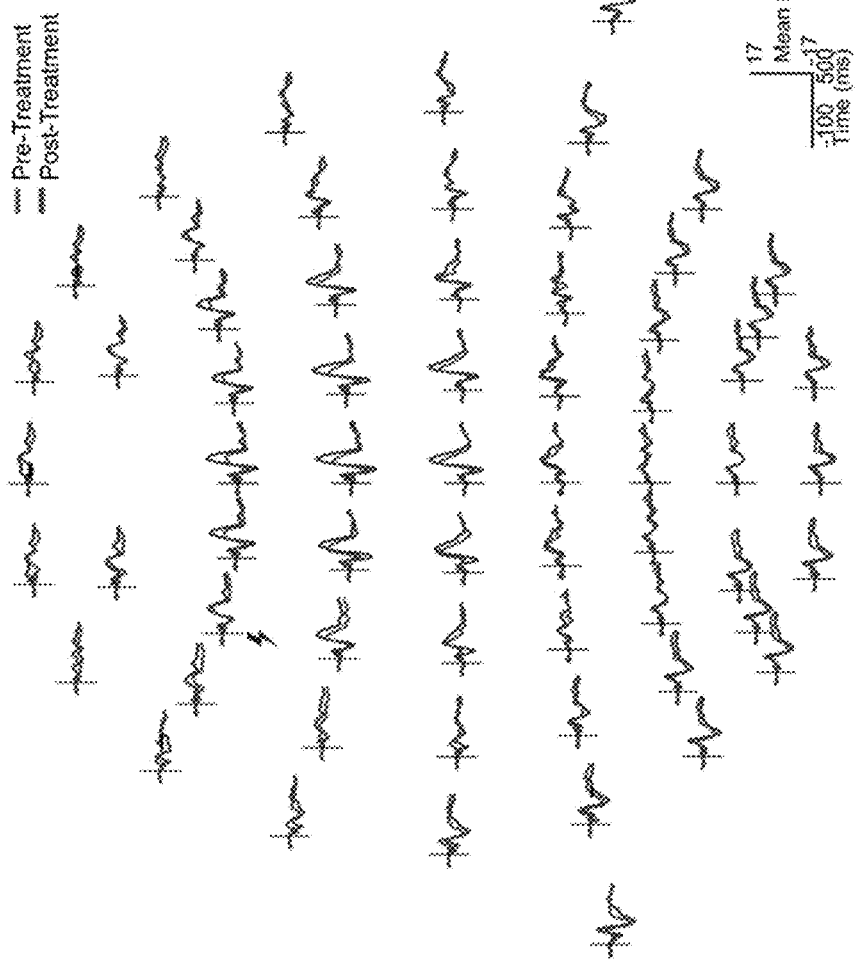

Example 2: Daily rTMS Modulates the Pattern of Evoked Electrical Activity Depending on Clinical Outcome First, the investigation determined the effect of rTMS on spTMS-evoked EEG potentials (TEPs) before and after 20 days of daily 10 Hz left DLPFC rTMS when delivering spTMS pulses to the DLPFC site later used for daily rTMS stimulation. As seen in FIG. 2A, rTMS induced both local and distributed sensor-level changes in the TEP. These changes were especially evident in ipsi-parietal, centro-parietal, and bilateral DLPFC regions. Focusing on electrodes near the site of stimulation ("local" in FIG. 2B) or centrally, a reduction in the p200 (200 msecs pulse) component of the TMS evoked response (TEP200, p200 response or simply p200) in particular is observed after daily rTMS but not after sham rTMS. This significant interaction is seen in FIG. 2C. The magnitude of change in TEP200 was best predicted by baseline magnitudes of the TEP200 (FIG. 2D). Next, the investigation was conducted to seek to characterize the TEP200 and further understand the regions and mechanism by which the TEP200 is modulated by rTMS. Scalp topography and source localized plots of the TEP200 demonstrate that the potential is located primarily in lateral and medial prefrontal cortices as well as motor and somatosensory regions (FIG. 2E). Stratifying by clinical response (>50% reduction in depressive symptoms) uncovered p200 suppression in lateral and medial prefrontal cortices in the responders group (FIG. 2F; n=6, t-stat>2) with no change in the non-responders group (n=9). The changes observed in the response group for the TEP200 were not observed for other components of the TEP or for the sham treatment group.

Figure 3A:
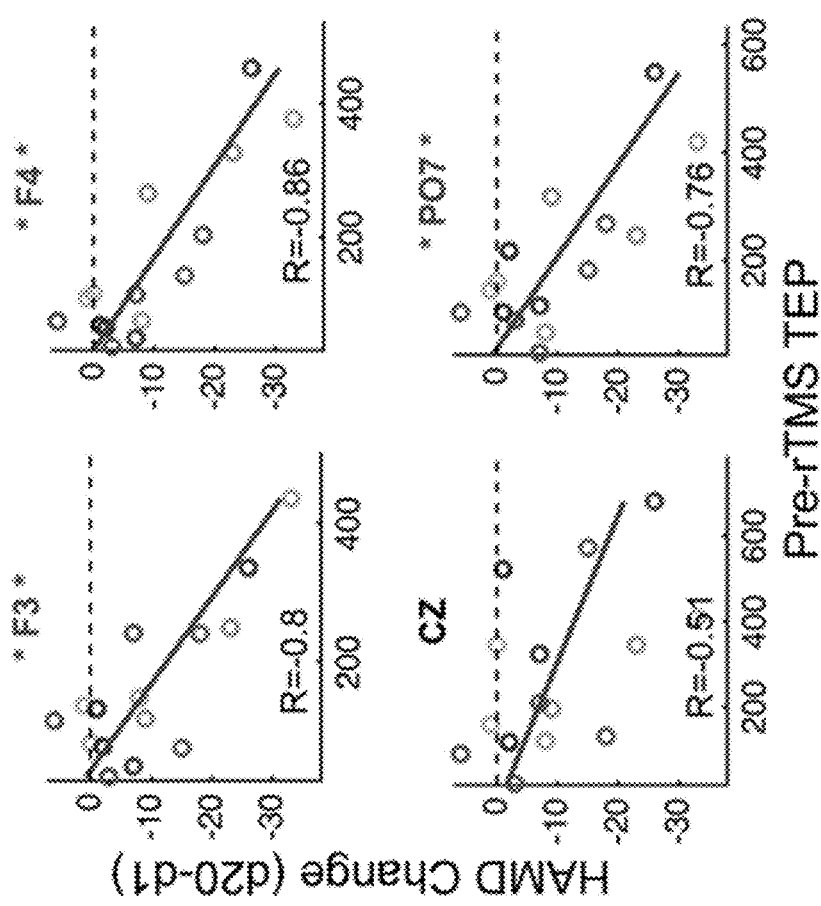
FIGS. 3A-3G. Pre-treatment TMS-evoked brain activity and change with rTMS predict clinical outcome.
Figure 3B:
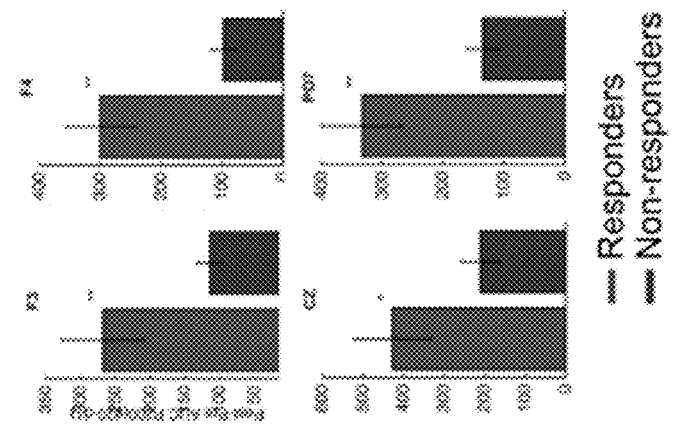
Figures 3C, 3D:
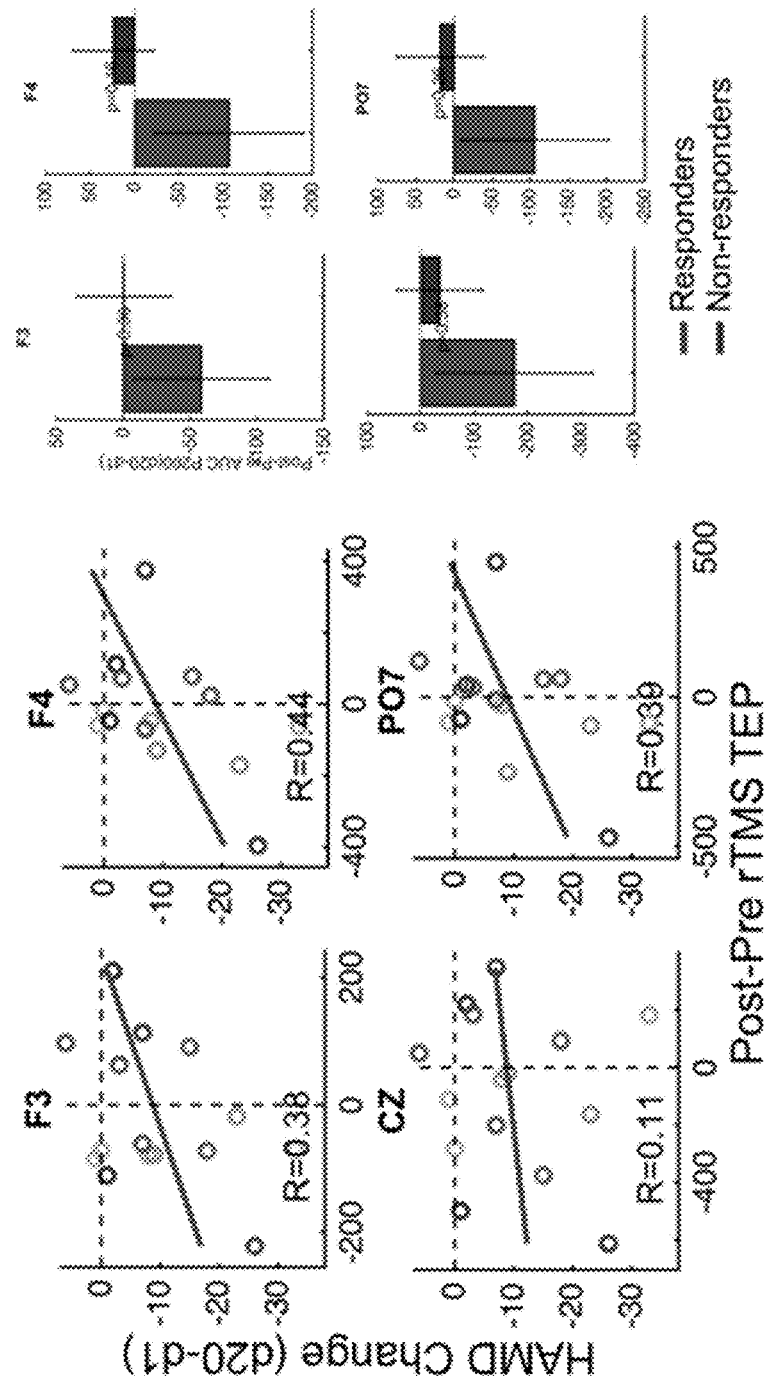
Figures 3E, 3F:
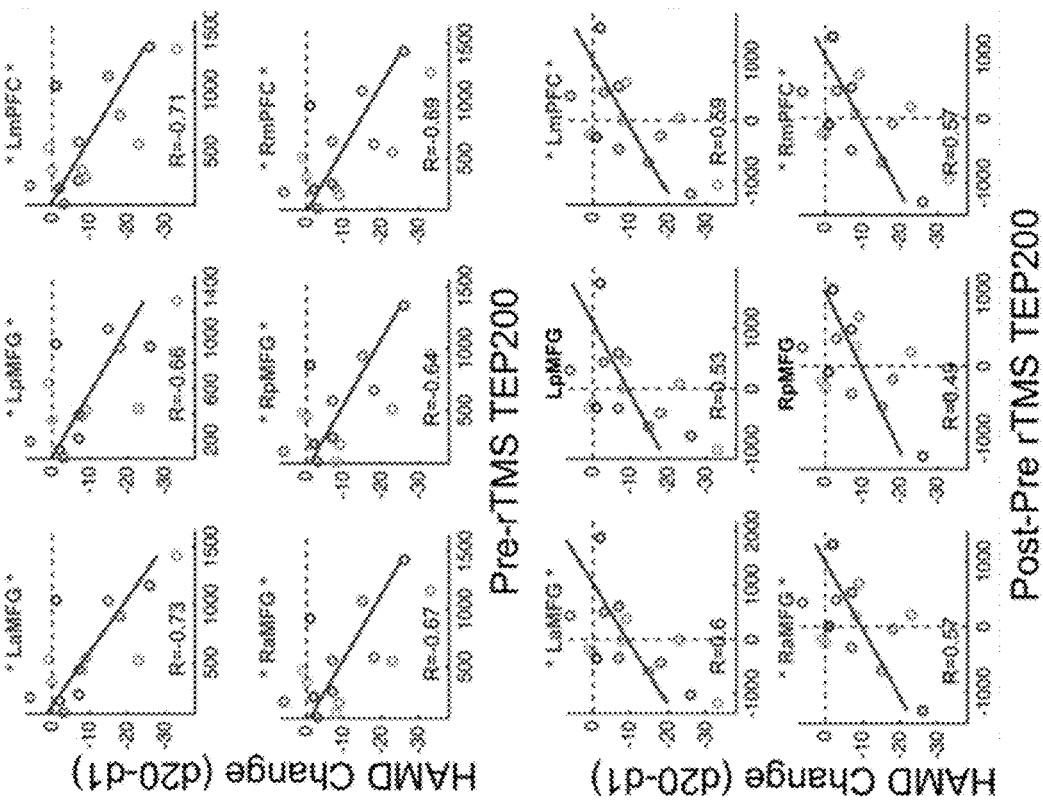
Figure 3G:
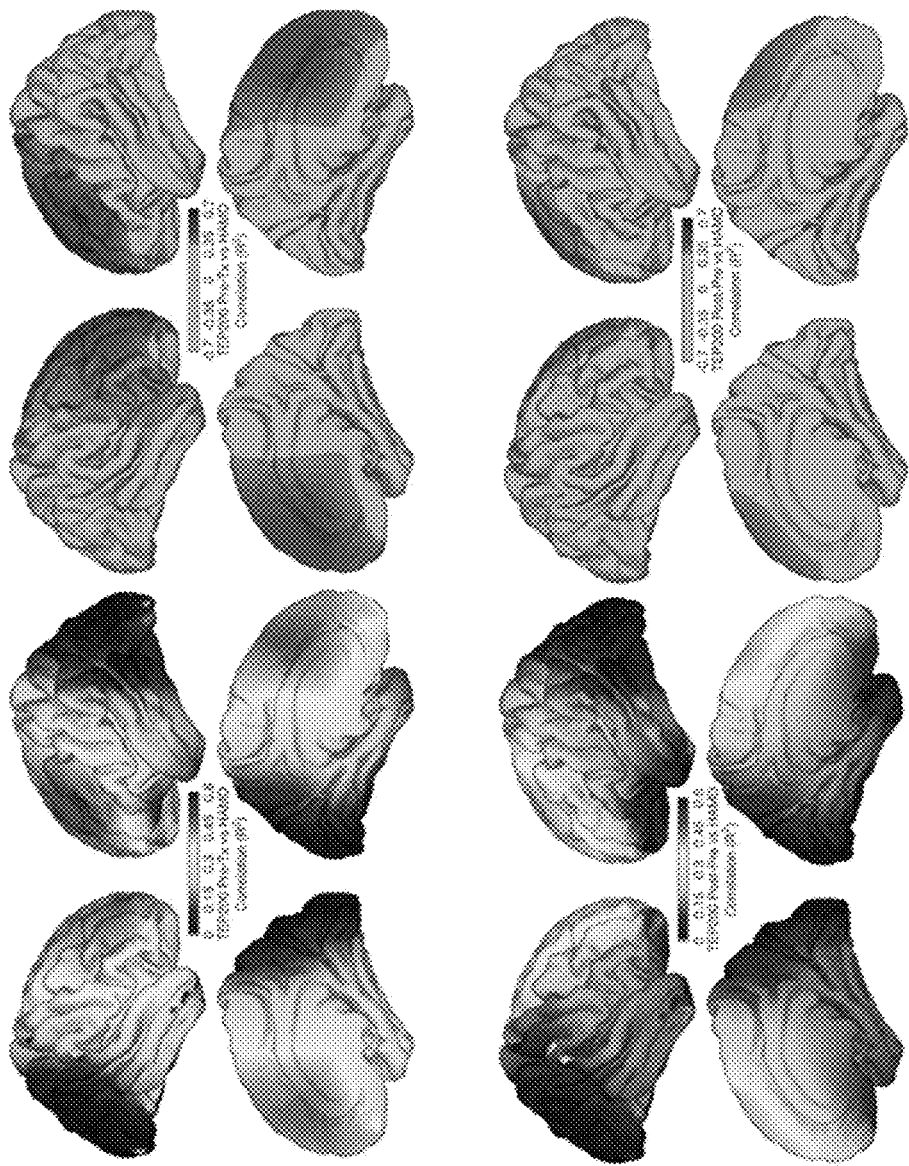

The experiments were conducted to examine whether baseline TEP200 magnitude or change in TEP200 across rTMS was related to treatment outcome. As seen in FIGS. 3A-3B, greater magnitude of the TEP200 in prefrontal, central and parietal channels at baseline was associated with a greater reduction in depression with treatment (based on a correlation analysis or a comparison of responders to non-responders). Similarly, across multiple electrodes, the amount of change in the TEP200 correlated with the amount of clinical change in depression (FIGS. 3C-3D), with those that had the greatest decrease in TEP200 with rTMS also showing the greatest clinical change. These results were then visualized in source space, where similar effects were observed (FIGS. 3E-3G).

Example 3: Modulation of Time-Frequency Dynamics by rTMS

The experiments were conducted to examine what changes rTMS induced in the frequency domain. At baseline, responses to single TMS pulses were characterized by an increase in broadband (1-40 Hz) power within the first 80 msecs, followed by prolonged suppression of power <15 Hz from 150-800 msecs (FIGS. 4A-4H). Group (rTMS/sham) x time (pre/post treatment) interactions demonstrated early differences in gamma power in local, ipsilateral parietal, and bilateral frontal regions and later differences in alpha power across centrally-located sensors (FIGS. 4A, 4B). Specifically, the rTMS arm showed greater early broadband suppression than the sham arm, which showed less suppression and only at lower frequencies. The rTMS arm also showed greater later alpha power increases (due to blunting of the alpha suppression observed at baseline), over left DLPFC and central regions (FIGS. 4C, 4D). In source localization analyses, rTMS was found to induce widespread early gamma power suppression localized to medial and lateral prefrontal regions (FIG. 4E, middle panel, T-stat >2). Sham treatment also induced early gamma suppression, but in a more confined region (FIG. 4E, right panel).

Finally, the experiments were conducted to examine if the both the strength of early gamma baseline power as well as the strength of early gamma power modulation predicted clinical outcome. Baseline gamma power correlated with clinical outcome in the left angular gyrus, left visual, as well as bilateral ventromedial prefrontal cortices, whereas the strength of early gamma modulation correlated with clinical outcome in left visual as well as right ventromedial prefrontal cortex (FIG. 4F; all R2>0.35). In contrast, late alpha power exhibited no change following rTMS treatment (FIG. 4G, middle panel) and neither baseline late alpha power nor the strength in late alpha power modulated predicted clinical outcome (FIG. 4H).

Example 4: Acute Vs Chronic Effects of rTMS

It is presently unknown whether a single rTMS session can induce the same network changes, even for a short period following rTMS, as are seen with daily rTMS treatment. A correspondence between acute and chronic rTMS changes would facilitate development of new rTMS methods as variations can be more readily tested in acute rTMS protocols. The investigation was conducted to examine the relationship between acute and chronic rTMS by analyzing spTMS responses before/after a brief 6 minute rTMS "probe" session using the same stimulation target and regimen as used for daily rTMS (FIG. 5A). Both pre-treatment probe rTMS and daily rTMS elicited similar ipsilateral DLPFC, bilateral parietal, and central TEP p200 suppression. Strikingly, repetition of the rTMS probe after treatment failed to result in acute suppression of the TEP200 post-treatment (FIG. 5C).

Next, the experiments were conducted to access whether the change in brain activity elicited by the probe rTMS also predicted clinical outcome, which would support a correspondence between the capacity for plasticity and treatment efficacy. Pre-treatment probe rTMS elicited TEP200 changes that corresponded to clinical outcome in lateral and medial prefrontal as well as right visual regions (FIG. 5A); daily rTMS elicited TEP200 changes that predicted outcome across more widespread prefrontal regions (FIG. 5B). By contrast, post-treatment probe rTMS changes did not predict clinical outcome (FIG. 5C).

Figure 6A:
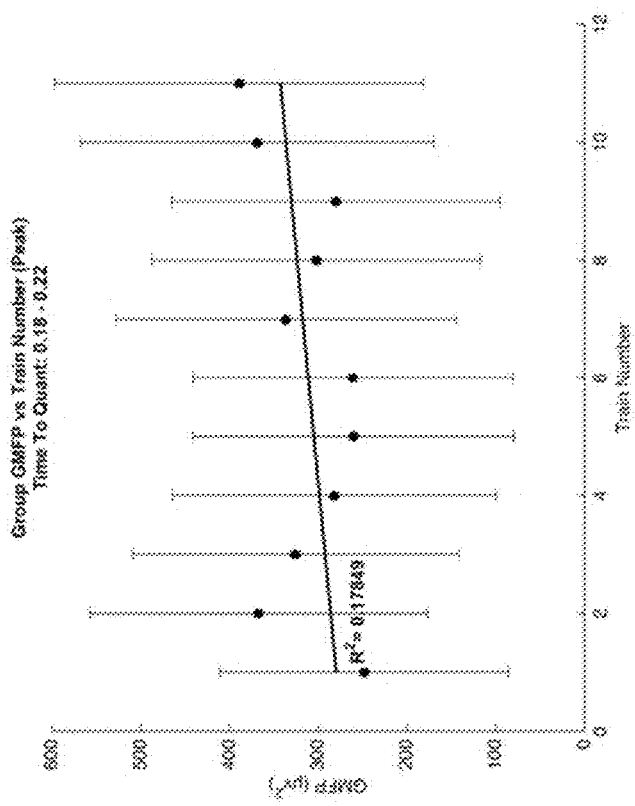
FIGS. 6A-6B. Intra-rTMS pulses monitor modulation of brain activity.
Figure 6B:
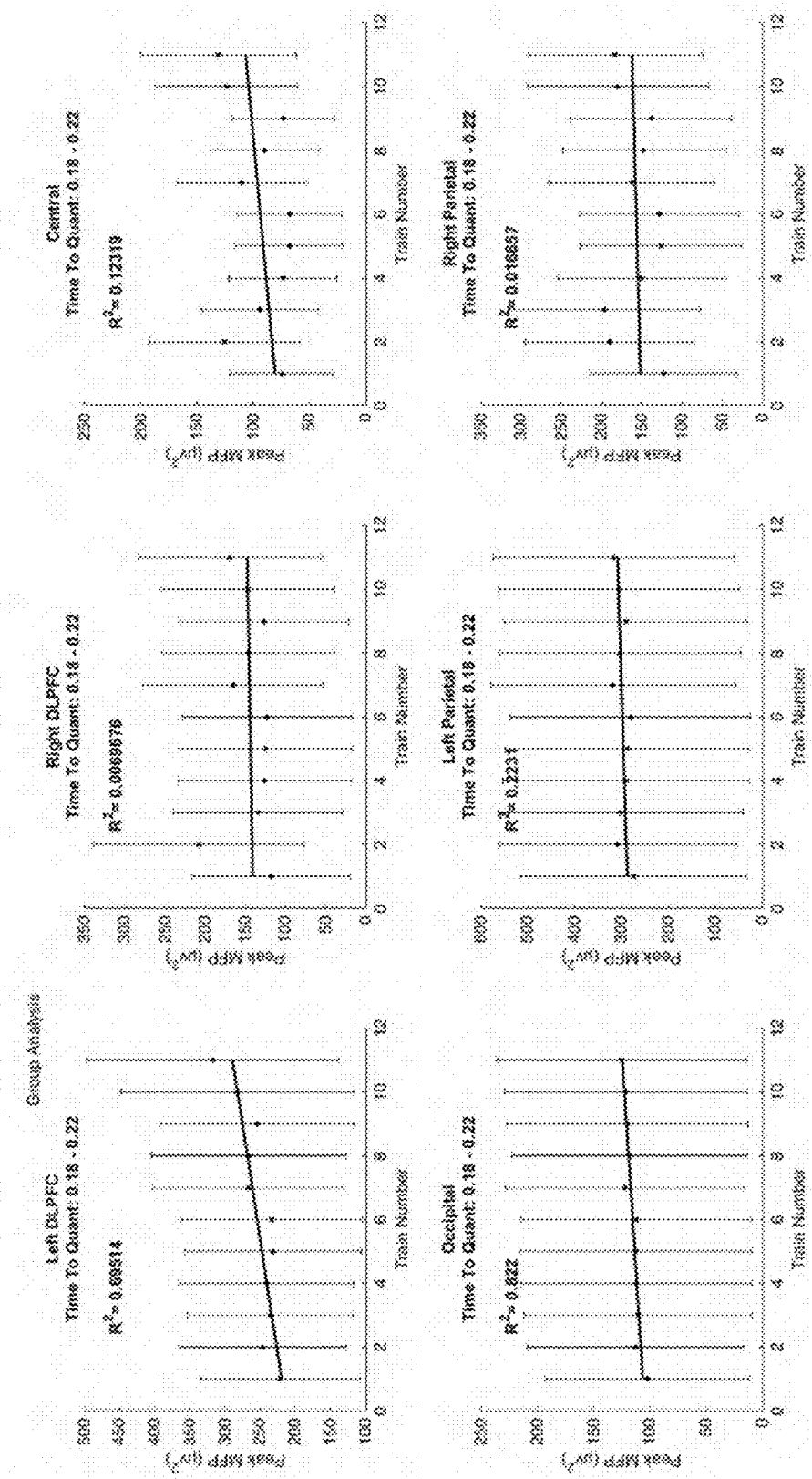
Figure 7A:
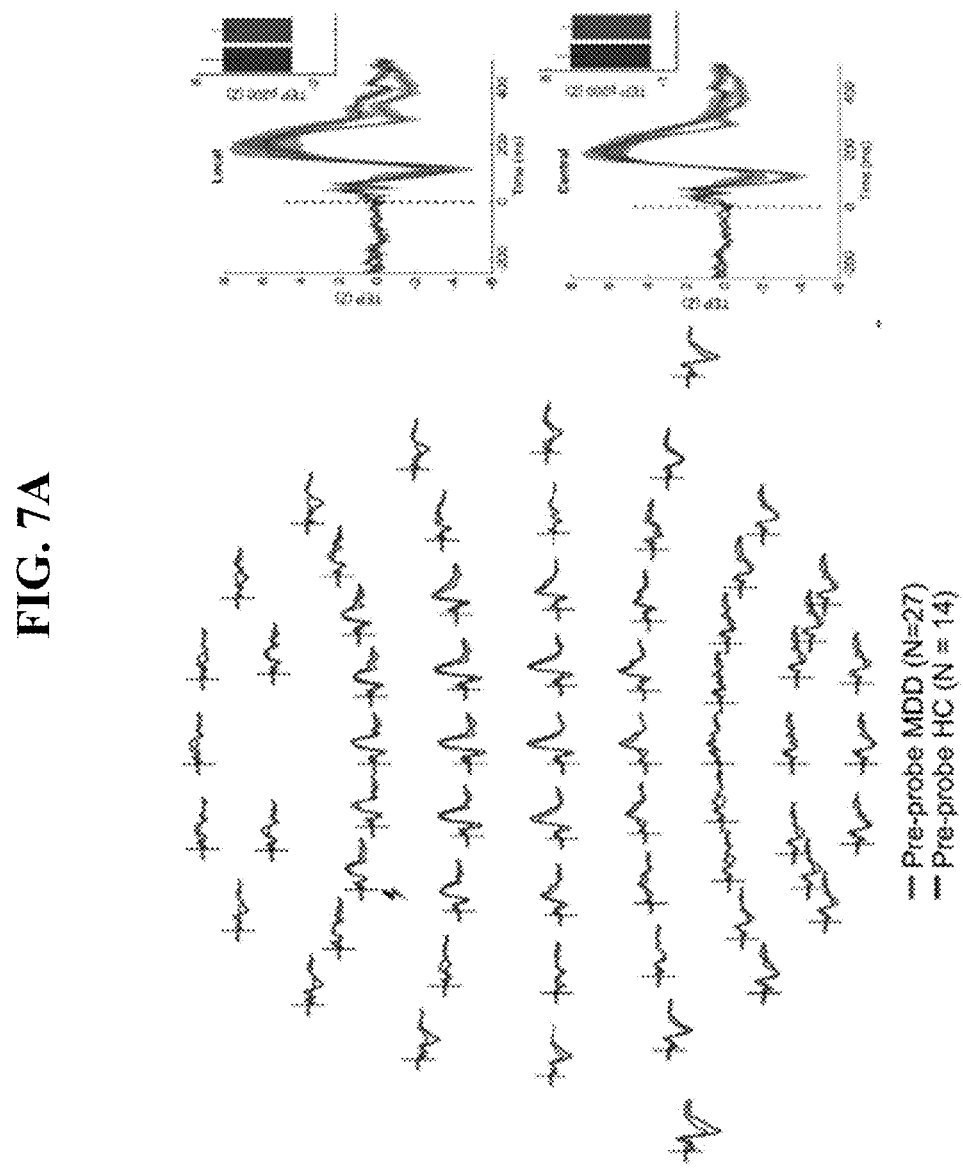
FIGS. 7A-7C. Healthy controls (HC) and patients with MDD demonstrate similar patterns of evoked brain activity.
Figure 7B:
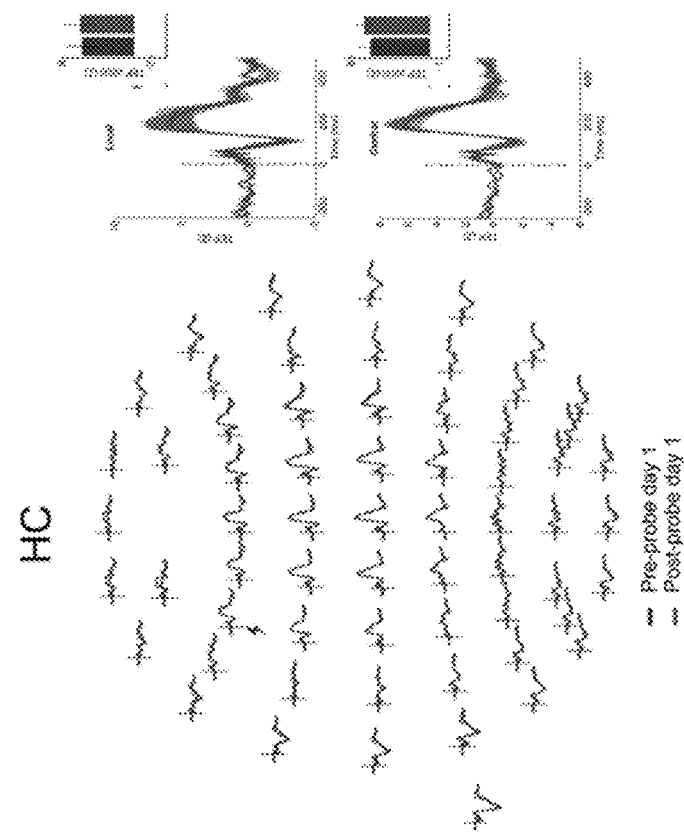
Figure 7C:
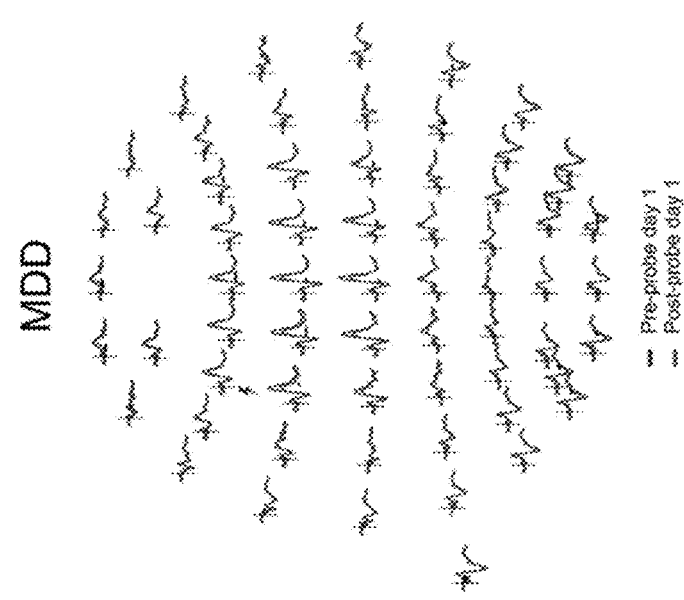
Figure 8:
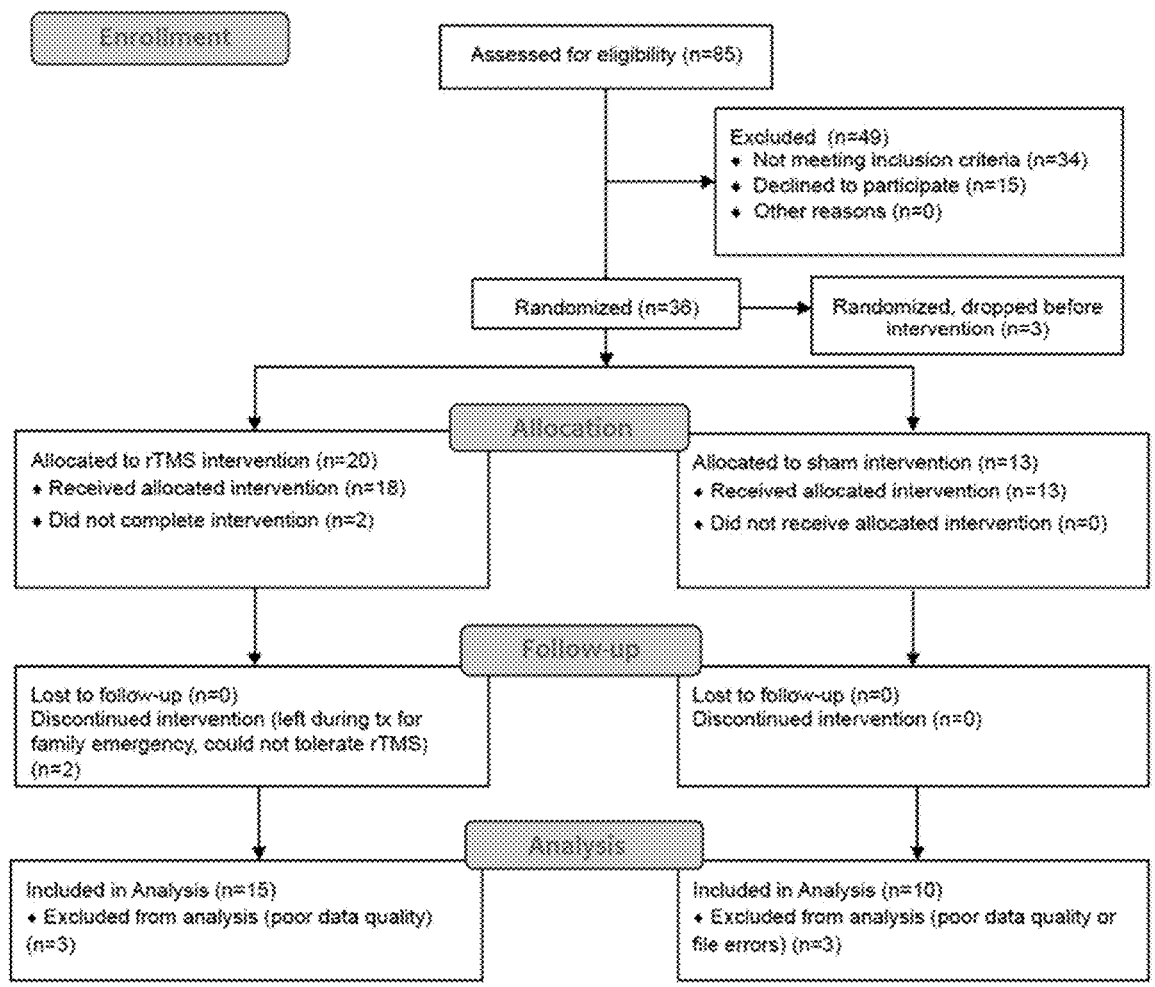
FIG. 8. Study enrollment flowchart.

Example 5: Changes in TMS-Evoked Potentials are Seen During the Course of an rTMS Treatment Session While the significant changes in the TEP due to rTMS were observed, the ability to monitor the degree to which rTMS modulates brain activity in real-time would represent a significant advantage. The experiments were conducted to examine the effects of probe rTMS by analyzing the TEP200 following the last pulse of each train during the rTMS session. Across subjects, the global mean field power increased throughout the probe session (N=22; $R^2$=0.18, FIG. 6A). On a regional level, these changes were most evident in the left DLPFC site of stimulation region (N=22; 30% increase in mean field power; $R^2$=0.69) and occipital regions (N=22; 20% increase in MFP; $R^2$=0.82). These changes were not evident in the earlier components of the TEP.

Example 6: Closed-Loop rTMS Treatment

Future applications include utilization of this EEG biomarker to optimize stimulation site, predict treatment outcome, monitor treatment efficacy, and propose novel stimulation protocols optimized for neuroplasticity as well as to support closed-loop rTMS. A machine learning algorithm can use EEG analysis of the rTMS evoked response to modulate an rTMS treatment protocol in real-time. The treatment protocol can be additionally modified as needed based on the individual's subsequent rTMS evoked response.

Example 7: Software for Automated Analysis of TMS/EEG Data

The analysis of the spTMS-EEG data can be complicated by the artifacts. In addition to typical EEG artifacts (e.g. eye movements and EKG), the spTMS-EEG data can also be contaminated by a number of unique artifacts, such as the TMS pulse artifact, TMS-induced scalp muscle artifacts, and recharge artifacts. Together, the amplitude of these artifacts can be several orders higher than that of the true neural signals, impeding the extraction of useful information from the data.

Despite the success of independent component analysis (ICA) in EEG artifact rejection, the classification of the ICs is often performed manually in a highly time-consuming and subjective manner. To address this issue, a fully automated spTMS-EEG artifact rejection algorithm based on ICA is developed. In the calibration stage, a training database is first built with the ICs labeled by EEG experts. Each IC has a binary label indicating whether it is a true neural signal or not. A linear classifier is then trained by using predefined features associated with the labeled ICs. After the calibration, the protocols of the classifiers are stored to allow the machine to automatically classify unseen ICs.

The design of the features is one of the important aspects for the performance of the algorithm. The developed algorithm computes a set of discriminative features that comprehensively capture the spatio-temporal-spectral characteristics of the artifact and non-artifact ICs. Results on the in-house spTMS-EEG data sets show that the performance of the algorithm is on par with EEG experts, achieving an average test accuracy of 92%. The developed algorithm is suited for the fast preprocessing of the spTMS-EEG data sets collected in large-scale or online research studies.

Example 8—Experimental Approach

Effects of rTMS on cortical circuitry in depression.

Figure 9A:
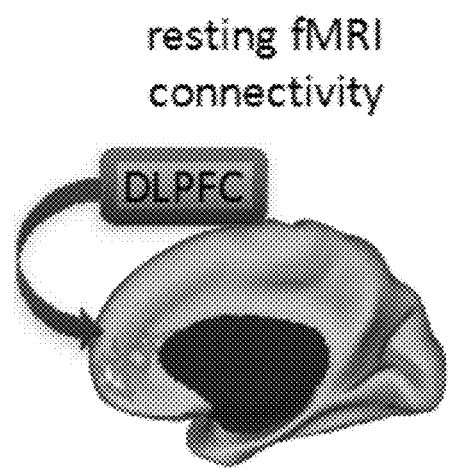
FIGS. 9A-9C.
Figure 9B:
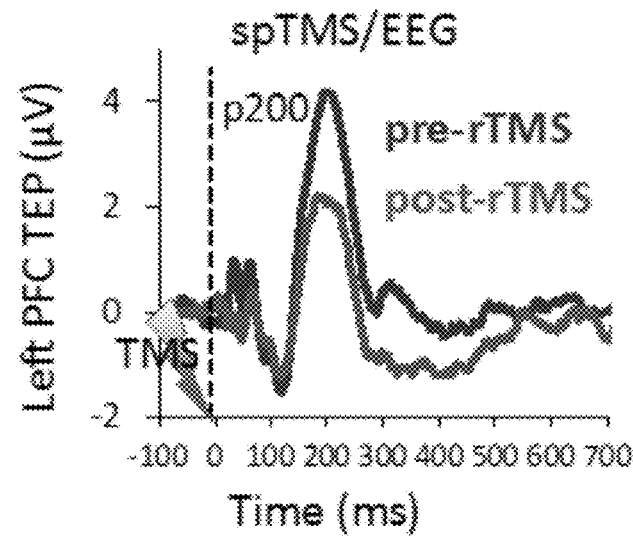
Figure 9C:
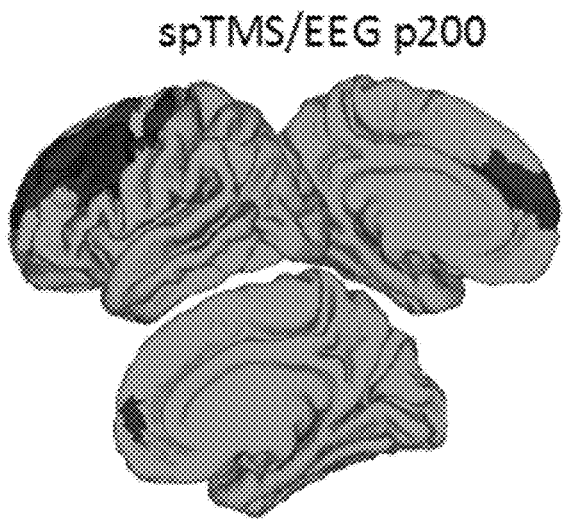

The experiments were conducted to study the impact of the FDA-cleared standard rTMS treatment protocol for depression on resting-state fMRI connectivity in 17 depressed outpatients. Based on prior literature showing hyperconnectivity within the default mode network and between the default mode network and the frontoparietal executive network (of which the dlPFC is part) in depression the experiments were conducted to examine the effect of rTMS on these networks. It was found that rTMS normalized hyperconnectivity between the dlPFC and the medial prefrontal portion of the default mode network (FIG. 9A). This effect is also consistent with the concurrent TMS/fMRI work in healthy participants, which found that single pulse stimulation to the executive network's dlPFC node modulated medial prefrontal activity. More recently, spTMS/EEG was used to characterize changes in causal circuit dynamics with rTMS treatment in depression. Randomized 30 depressed patients were tested to real versus sham left dlPFC rTMS (2:1 real/sham ratio), which we analyzed in an intent-to-treat manner using linear mixed modeling. It was found that real rTMS was associated with a significant reduction in the p60 ($p<0.05$) and p200 ($p=0.002$; FIG. 9B) potentials compared to sham rTMS, which may thus indicate a reduction in intracortical inhibition. Since the p200 is the potential most-reliably identified in individual patients for the purpose of optimizing TMS site/coil angle protocols, the investigation focuses on the p200 findings, though very similar results were obtained for the p60. Weighted minimum norm based source localization revealed, much like the resting-state fMRI study, that the change in the p200 originated from the dlPFC and medial prefrontal cortex (FIG. 9C).

The p200 TEP reflects intracortical inhibition, implications for the mechanism of rTMS.

Figure 10:
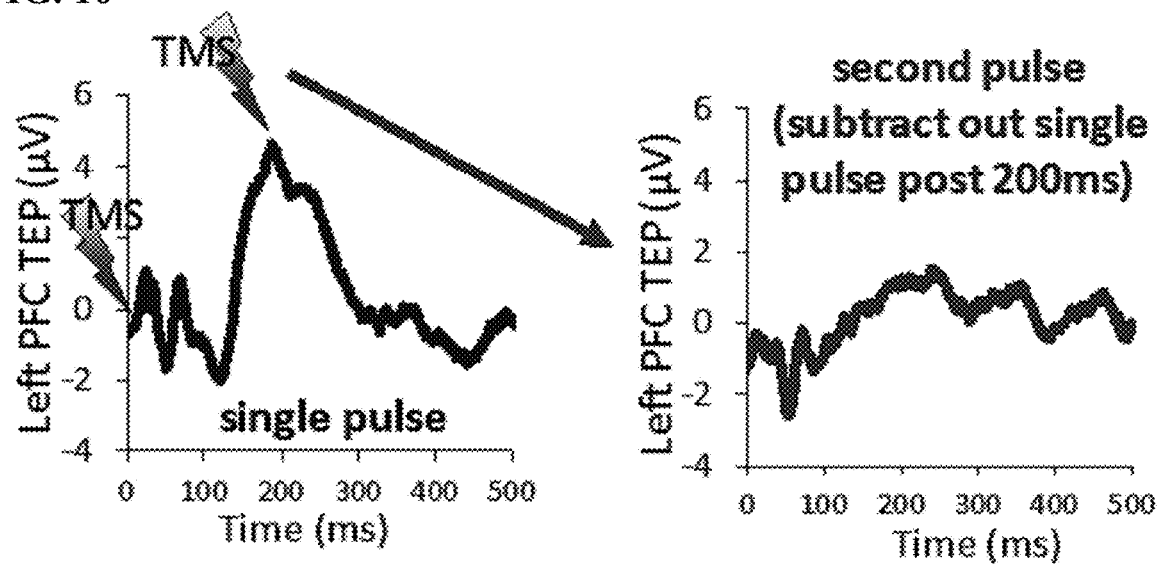
FIG. 10. The spTMS/EEG p200 is an inhibitory potential, evident by a blunted TEP for a second pulse, if delivered 200 milliseconds (msecs or ms) after an initial single pulse. That is, first pulse resulted in an inhibitory state for cortex at 200 ms which blunted the response to the second pulse.

To further understand the causal significance of the p200, a paired-pulse experiment was conducted in healthy individuals, as the majority of paired pulse protocols were performed only in motor cortex and examined only intervals <150 milliseconds (ms), with dlPFC paired pulse experiments only examining an interval of 100 ms. It was found that if a second pulse were delivered 200 ms after an initial TMS pulse to the dlPFC, it was much smaller in amplitude than if it were delivered alone (FIG. 10). Thus, the cortex is in a more inhibited state 200 ms after activation by a TMS pulse and therefore the magnitude of the p200 reflects in large part the amount of intracortical inhibition. These results are also consistent with expectations from the cat cortex work above, as well as a large body of human spTMS/EEG work showing that the n100 potential is likewise inhibitory with respect to delivery of a second TMS pulse. Taking these findings together with the spTMS/EEG changes following rTMS treatment above, rTMS appears to decrease intracortical inhibition in the dlPFC (indexed by a smaller p200), which may help normalize inter-regional connectivity.

Prediction and tracking of clinical outcome with rTMS.

Figure 11A:
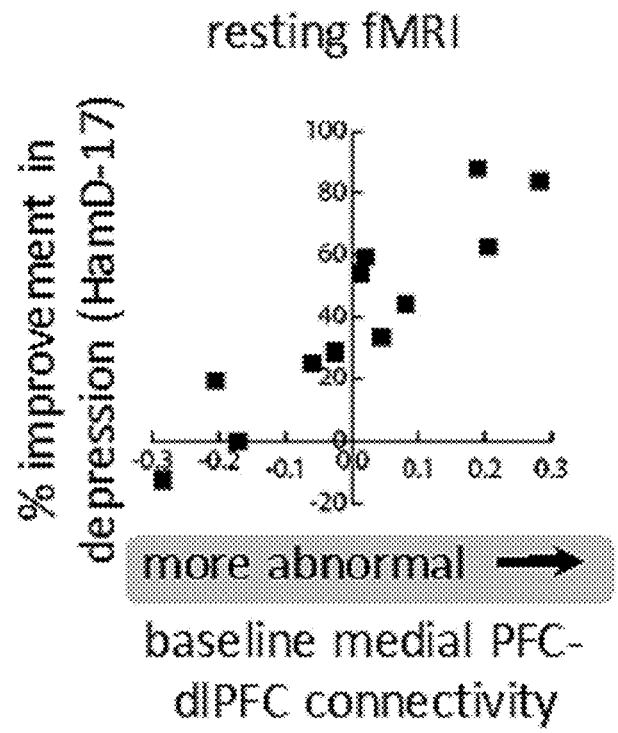
FIGS. 11A-11D.
Figure 11B:
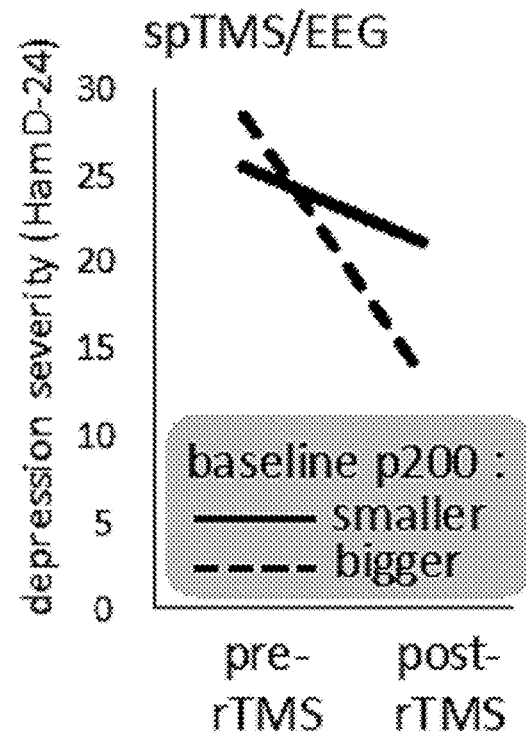
Figure 11C:
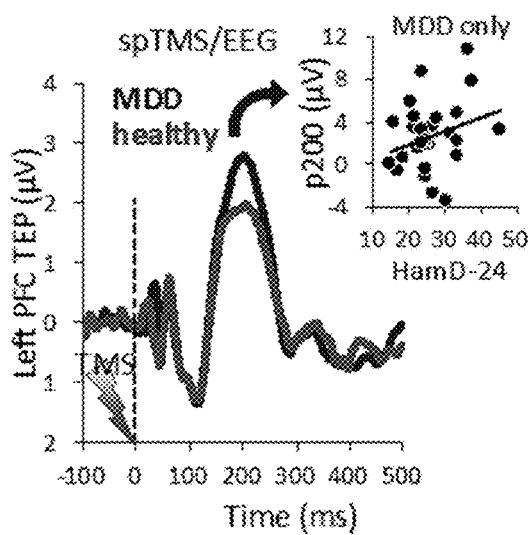
Figure 11D:
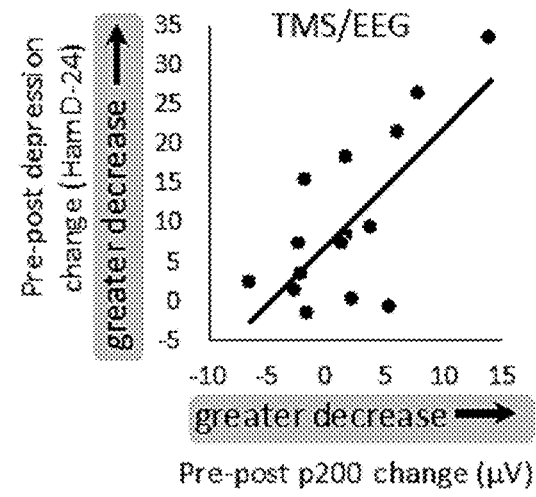

Previous work both using fMRI and TMS/EEG suggests that baseline circuit functioning robustly predicts rTMS outcome. It was found in the resting-state fMRI study that the more abnormally hyper-connected the medial prefrontal cortex and dlPFC were, the better patients responded to rTMS treatment (FIG. 11A). A similar result was obtained in the spTMS/EEG study, where the larger the baseline dlPFC p200, the greater the reduction in depression scores with treatment, even controlling for baseline depression (FIG. 11B; $p<0.001$; shown as a median split to represent results from the mixed model analysis). While some investigation focuses on results with electrodes overlying the left dlPFC, as this signal relates most closely to the proposed intervention target (i.e. left dlPFC intracortical inhibition), similar p200 results were obtained with central and right dlPFC electrodes. Baseline dlPFC p200 was also greater in depressed patients and correlated with greater depression scores (FIG. 11C; $p<0.05$). As in the resting fMRI work above, the more abnormal the dlPFC's response to TMS, the better patients responded to rTMS treatment. Finally, the greater the reduction in the dlPFC's p200 response with treatment, the greater the reduction in depression scores, while controlling for baseline p200 (FIG. 11D; $p=0.017$). In summary, the more abnormal the baseline dlPFC p200, baseline fMRI connectivity, or the greater the rTMS treatment-induced reduction in the p200, the better the clinical outcome with rTMS.

Figure 12:
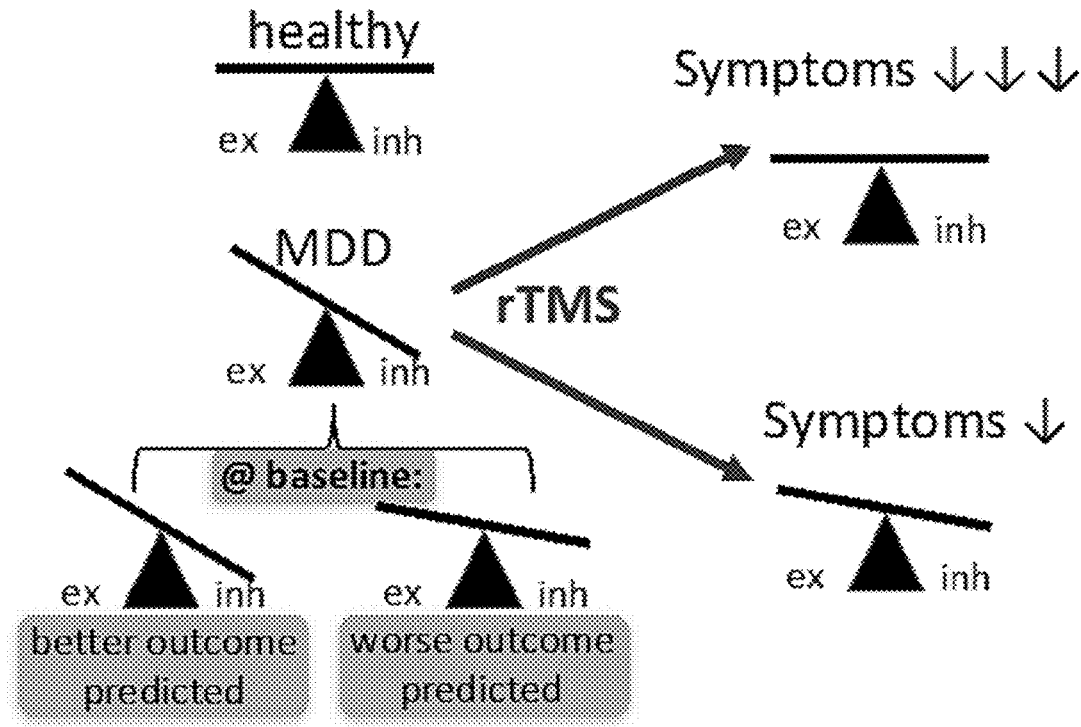
FIG. 12. A simplified diagram depicting one of working models of dlPFC intracortical inhibition and rTMS mechanism. Intracortical inhibition is increased in more depressed patients (indexed by the p200 TEP). Greater intracortical inhibition at baseline (larger p200) predicts better rTMS outcome. The greater the reduction in intracortical inhibition with treatment (p200 suppression), the better the treatment outcome. Inh: inhibition; ex: excitation.

It was found that the p200 TEP to dlPFC stimulation was increased in depression, reflects intracortical inhibition and is specifically reduced by rTMS treatment (wherein the degree of reduction correlates with the degree of symptom improvement). In the context of a principle of target engagement, reduction in intracortical inhibition in the left dlPFC is the physiological target of treatment, and the p200 TEP is the readout of target engagement (FIG. 12). Moreover, the more abnormal the dlPFC p200 response or fMRI connectivity at baseline, the better the clinical outcome with rTMS. This suggests that clinical outcome may be improved by finding the site and/or coil angle that yields the greatest baseline p200 (i.e. greatest engagement of intracortical inhibition), which is then targeted by rTMS treatment. Also, since the degree of rTMS-driven reduction in the p200 tracks the degree of clinical improvement, regularly following the p200 throughout treatment may indicate whether a sufficient dose of rTMS treatment has been delivered and whether there is any more to be gained by further treatment.

Individualized optimization of p200 TEP amplitudes.

Figure 13:
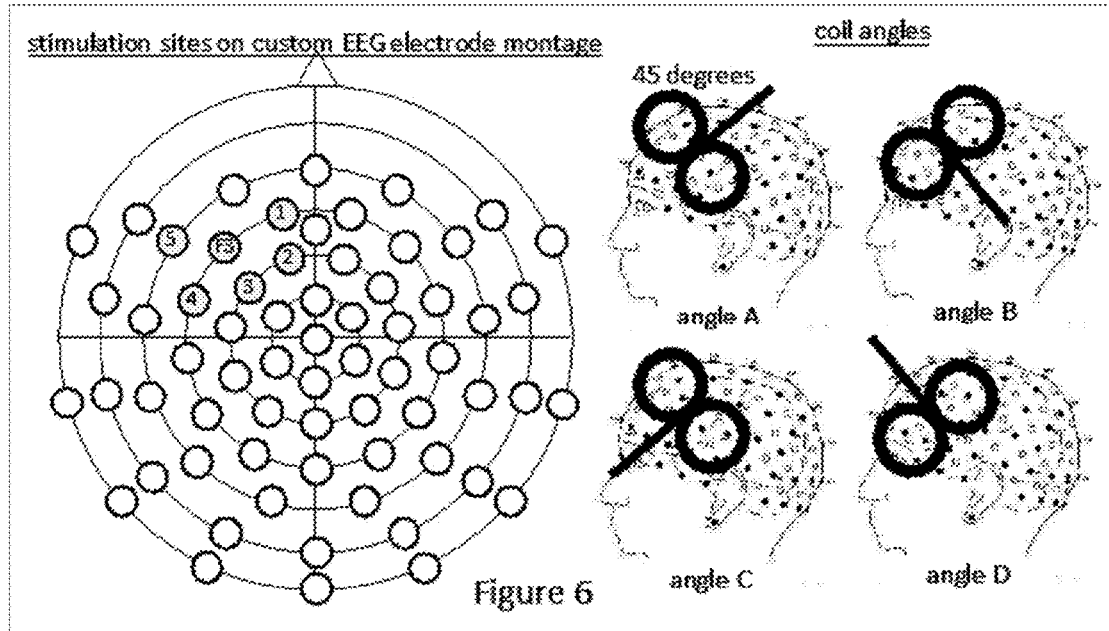
FIG. 13. Stimulation sites on custom EEG electrode montage.

To support the position that the magnitude of the p200 is sensitive to straightforward variation in how TMS is performed and not an invariant feature of the individual, the experiments were conducted to seek to demonstrate the expected impact of site of stimulation and coil angle in a pilot study. Taking the F3 electrode site and a 450 coil angle as the "default" procedure for rTMS (FIG. 13), the experiments were conducted to examine in eight individuals whether stimulation at nearby electrode positions or using other coil angles at F3 altered p200 responses. To do so, the p200 effect size differences between each variation and the default, expressed as Cohen's d was calculated. A moderate effect size difference ($d>0.5$) was considered as the required cutoff for a variation to be considered superior to the default. In the earlier experiments, the stimulation was done at nearby electrode positions (spaced by ~3 cm), but in the further work stimulation can be done at ~10 sites spaced across a 1 cm gap grid around F3. Likewise, because at the time of the pilot the automated spTMS/EEG artifact rejection algorithm was not yet sufficiently accelerated, the coil angles at the F3 site only at the initial experiments, but the coil angle in the further work can be varied at the site identified as optimal for each patient. The p200 potential was clearly identified for each of the eight pilot participants during the investigation, two of whom are shown as illustrative examples in FIGS. 14A and 14D. The bar graphs show the Cohen's d of the increase or decrease in the p200 amplitude relative to the default F3 site and 450 coil angle (which are therefore at a zero value). Data from Participant A show that no stimulation site yielded a larger p200 than the F3 site at $d>0.5$ (FIG. 14B), but that one coil angle was clearly superior to the default angle (FIG. 14C, denoted by a star). By contrast, data from Participant B show that three stimulation sites yielded larger p200 amplitudes than F3 (FIG. 14E, best site denoted by the star), but no coil angle was superior to the default 450 angle (angle A; FIG. 14F). Of the eight pilot participants, four had a site superior to F3, and three had an angle superior to 45 degrees. Two with sites superior to F3 also showed coil angle improvements over 45 degrees. In total, five of the eight participants showed either stimulation site or coil angle improvements over the default combination. The anatomical specificity in the further work can be further improved by performing the stimulation target search over more regions, and through use of MRI neuro-navigation. In summary, these data demonstrate that it is possible to individualize and optimize the site and coil angle for rTMS treatment based on each participant's spTMS/EEG response. This is the first step in being able to tie how rTMS is performed to the emerging understanding of its neurophysiological mechanisms.

Development of a fully-automated artifact-rejection algorithm for spTMS/EEG data.

Figure 15A:
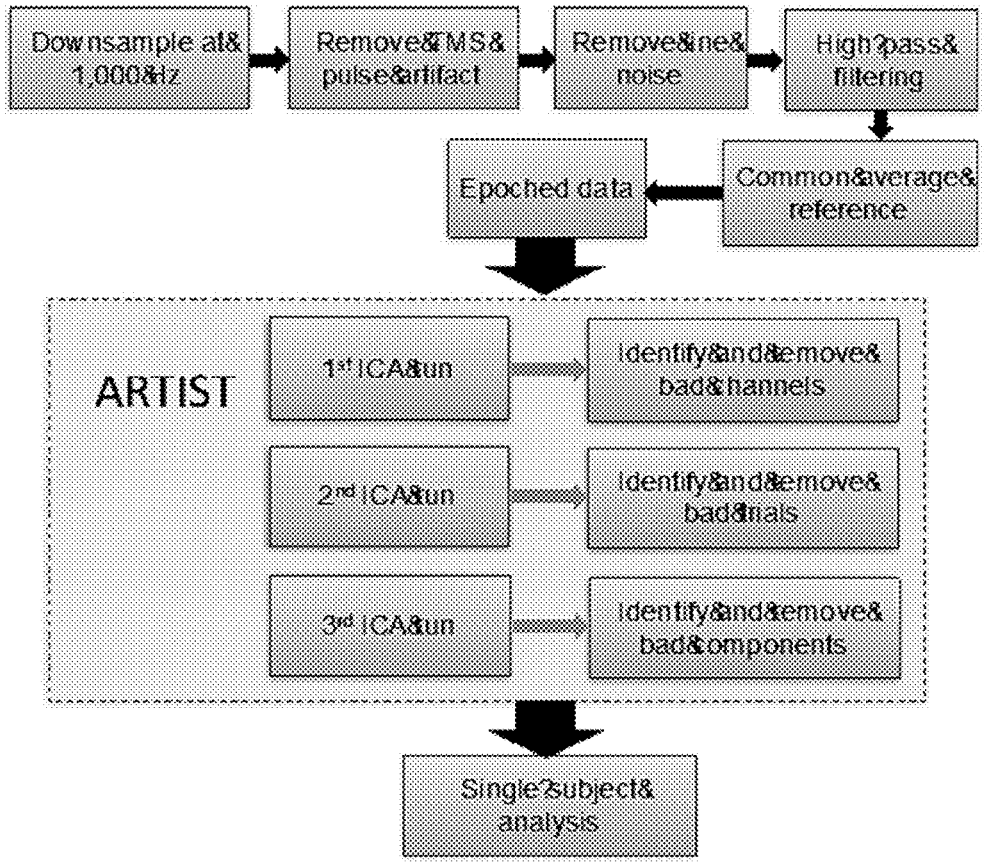
FIGS. 15A-15C.
Figure 15B:
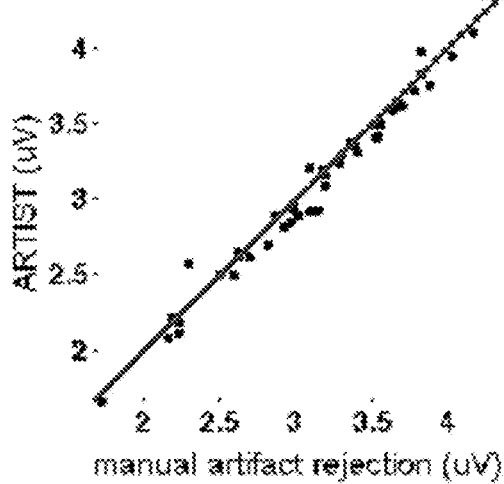
Figure 15C:
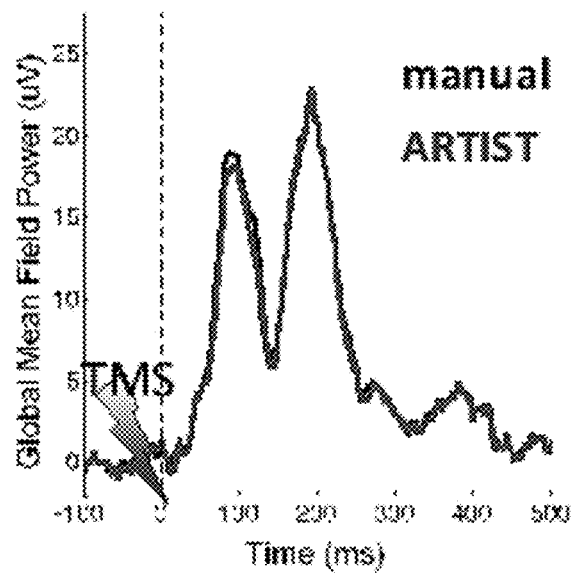

In addition to the conventional EEG artifacts, spTMS/EEG suffers from multiple stimulation-related artifacts including those derived from the stimulation pulse itself, scalp muscle activation, eye blinks, audible coil clicks, and coil recharge. Some of these artifacts can be minimized through experimental manipulations. For instance, noise-cancellation headphones with continuous masking white noise minimize auditory-evoked potentials; delay of the coil recharge can shift the recharge artifact beyond the time periods of interest. Scalp muscle activation artifacts, however, are of large magnitude and are unavoidable for frontal targets. As a result, removing artifacts from spTMS/EEG data becomes a time-consuming endeavor typically done through manual identification and rejection of artifactual channels and trials, and removal of artifact-associated independent components (ICs) extracted by independent component analysis (ICA). To be able to implement the individualization and optimization approach above in an efficient and clinic-friendly manner, it is essential that processing of spTMS/EEG be fully automated. Automatic artifact rejection for spTMS/EEG data is challenging as the morphology of the same artifact type may vary across subjects and stimulation sites, requiring that robust and invariant features be identified, including a set of temporally segregated TEPs. None of these issues are adequately dealt with by existing automated EEG processing algorithms. To address these challenges, the inventors developed and validated the first fully automated ICA-based artifact rejection algorithm that combines temporal and spectral features to separate artifacts from neural signals (Automated artifact rejection for Single-pulse TMS-EEG Data (ARTIST)). FIG. 15A shows the spTMS/EEG processing work flow, including the ARTIST algorithm. At the heart of this algorithm is a classifier, trained on manually-processed spTMS/EEG data from multiple stimulation sites and participants (2198 ICs), that labels artifacts based on 13 features (spatial range, regional activation, border activation, correlation with a horizontal eye movement template, correlation with a blink artifact template, EKG spatial features, EKG temporal features, current source density, maximum magnitude, short time magnitude, skewness, band-limited power and spectral features). Validation on data not used for training revealed that ARTIST classified artifact ICs at 96% accuracy, significantly out-performing a state-of-the art automated algorithm for conventional EEG data (Multiple Artifact Rejection Algorithm). The remaining misclassified ICs either explain a very small amount of the variance, or are ICs where manual rejection is uncertain. The magnitude of the resulting TEPs are highly correlated with manual processing (FIG. 15B; p200 r=0.989) and result in a TEP time course that is virtually identical to manually processed data (FIG. 15C).

Optimization of the rTMS protocol.

Based on the fact that there are several commonly-used rTMS stimulation patterns that are all thought to increase cortical excitability (i.e. 10 Hz, 20 Hz, intermittent theta burst), the inventors considered individualization and optimization of the stimulation pattern, by determining which one would most reduce p200 TEP amplitudes after a single rTMS session, for example, focusing on stimulation site and coil angle Optimization of the duration of rTMS (number of pulses or sessions): Tracking treatment-induced change in the p200 can help determine whether an adequate dose has been delivered, and whether additional improvement should be expected with more rTMS.

Selection of TMS stimulator/coils: There are presently three FDA-cleared "conventional TMS" stimulators for the treatment of depression, of which can be used (from MagVenture). Likewise, there are several TMS coil geometries that can be used (of which, the investigation can use a 65 mm liquid-cooled FIG. 15 coil).

spTMS/EEG acquisition methods.

The F3 electrode position can be located in each person and marked on their structural MRI scan (protocols below). Visor2 frameless stereotactic neuronavigation software (ANT Neuro) can be used to create a grid of ~10 stimulation sites (depending on specific patients' anatomy), each spaced by 1cm, designed to cover the lateral prefrontal cortex at sites accessible to TMS (i.e. avoiding frontopolar and ventrolateral prefrontal regions over which rTMS may be very painful due to nerve and muscle stimulation). EEG can be recorded using a TMS-compatible 64-channel Brainamp DC amplifier (which has a large dynamic range to avoid saturation by the TMS pulse), using an EasyCap system with small Ag/AgCl electrodes and an active shielding system. The nose tip can serve as the reference. To avoid contamination of the EEG data by auditory potentials evoked by the TMS discharge clicks, subjects can wear earplugs playing continuous masking noise mimicking the click sound. A thin pad can be placed between the coil and electrodes to minimize TMS-induced vibratory noise. The TMS recharge artifact can be avoided by delaying recharge. Electrode positions on the scalp can be marked using the Visor2 neuronavigation system. TMS stimulation can be delivered using a MagVenture MagPro X100 stimulator operating at 120% of each participant's abductor pollicus brevis (thumb) resting motor threshold (thereby calibrating stimulation intensity), using a cool-B65 MagVenture TMS coil. The single-pulse TMS/EEG protocol entails jittered delivery of 150 TMS pulses with an average inter-stimulus interval of 2.5 seconds for each stimulation site or coil angle. Coil angles can be varied at 900 angles from the default angle of 450 off the anterior-posterior axis of the brain (i.e. coil angle A in FIG. 13). All coil angles and stimulation sites can be recorded using Visor2 neuronavigation software.

rTMS treatment protocol and spTMS/EEG assessment points.

Figure 16:
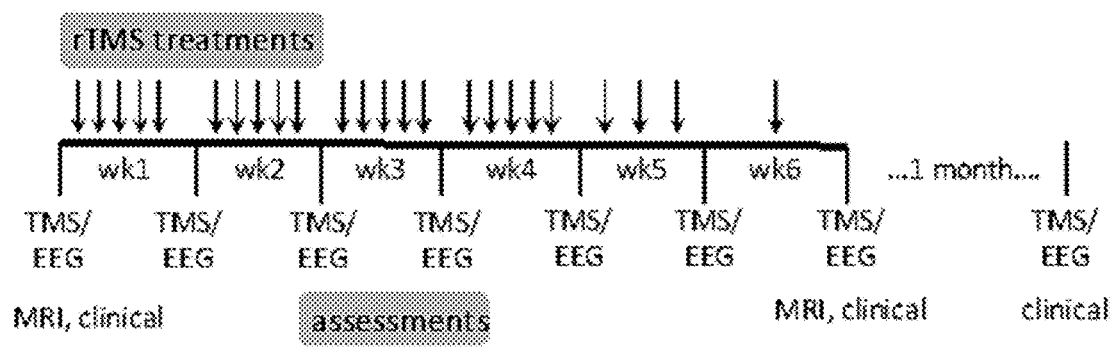
FIG. 16. rTMS treatment and assessment timeline.
Figure 17A:
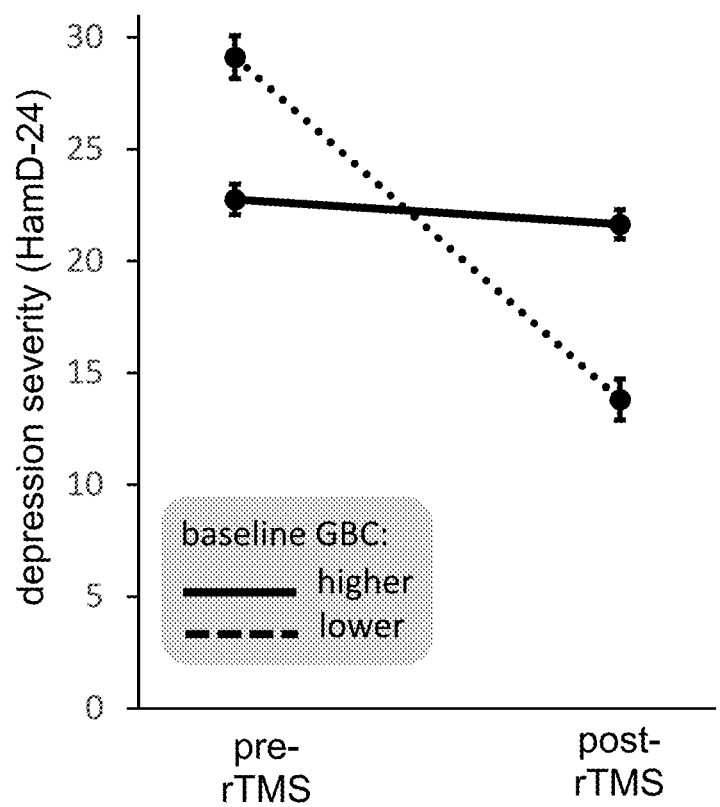
FIGS. 17A-17B.
Figure 17B:
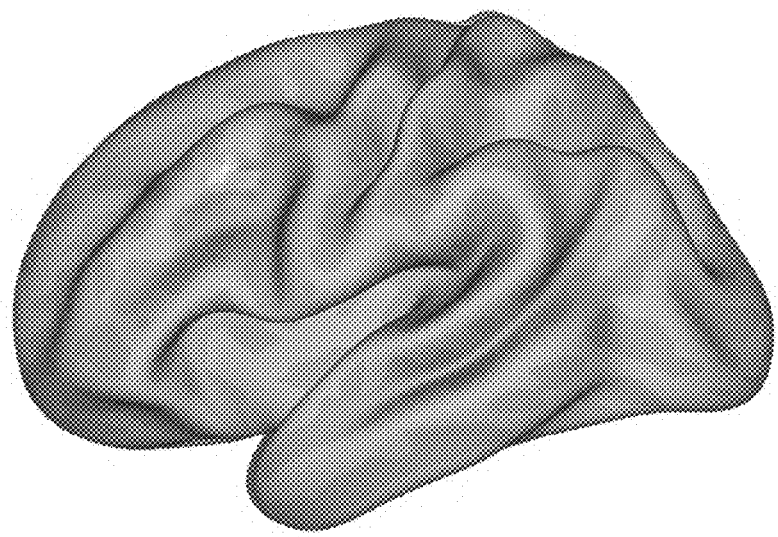

Drawing on the efficacy of 10 Hz rTMS stimulation, and suggestions that is important to deliver a sufficiently large number of pulses (e.g. patients received up to 90,000 pulses in the two major recent studies), as well as improvements in cooling of TMS coils, rTMS can be performed at 120% of motor threshold (MT) daily with 40 pulses delivered at 10 Hz (i.e. 4 s of 10 Hz) every 15 seconds (see FIG. 16). Treatment can occur over 20 sessions, with the first two days performed at 80% and 100% MT, respectively, to acclimate patients to the experience of rTMS. Patients can then receive a two-week taper, reducing to three and then one session per week. Durability of the intervention can be assessed again at a month following the end of the taper.

Example 9—Resting fMRI Connectivity and its Relationship with TMS/EEG Data

Figure 18A:
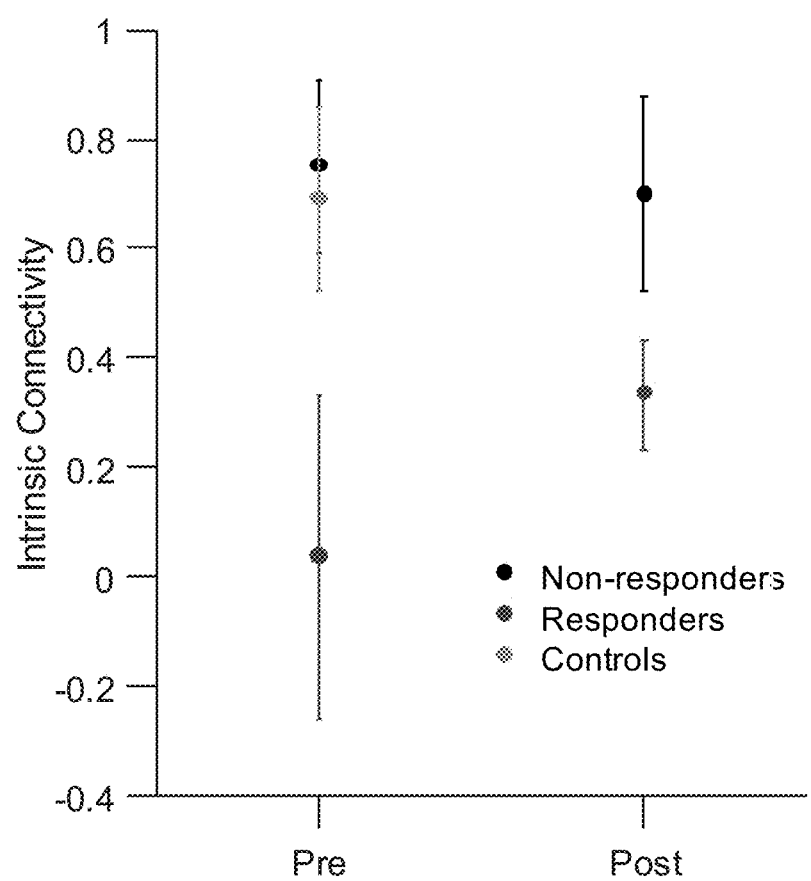
FIGS. 18A-18B.
Figure 18B:
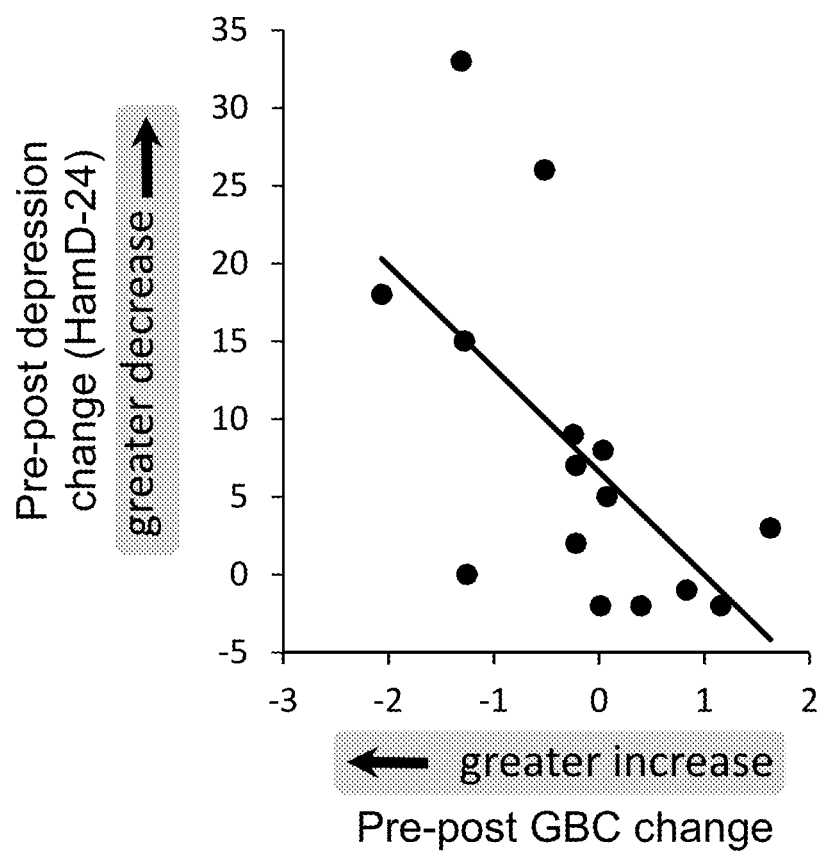
Figure 19:
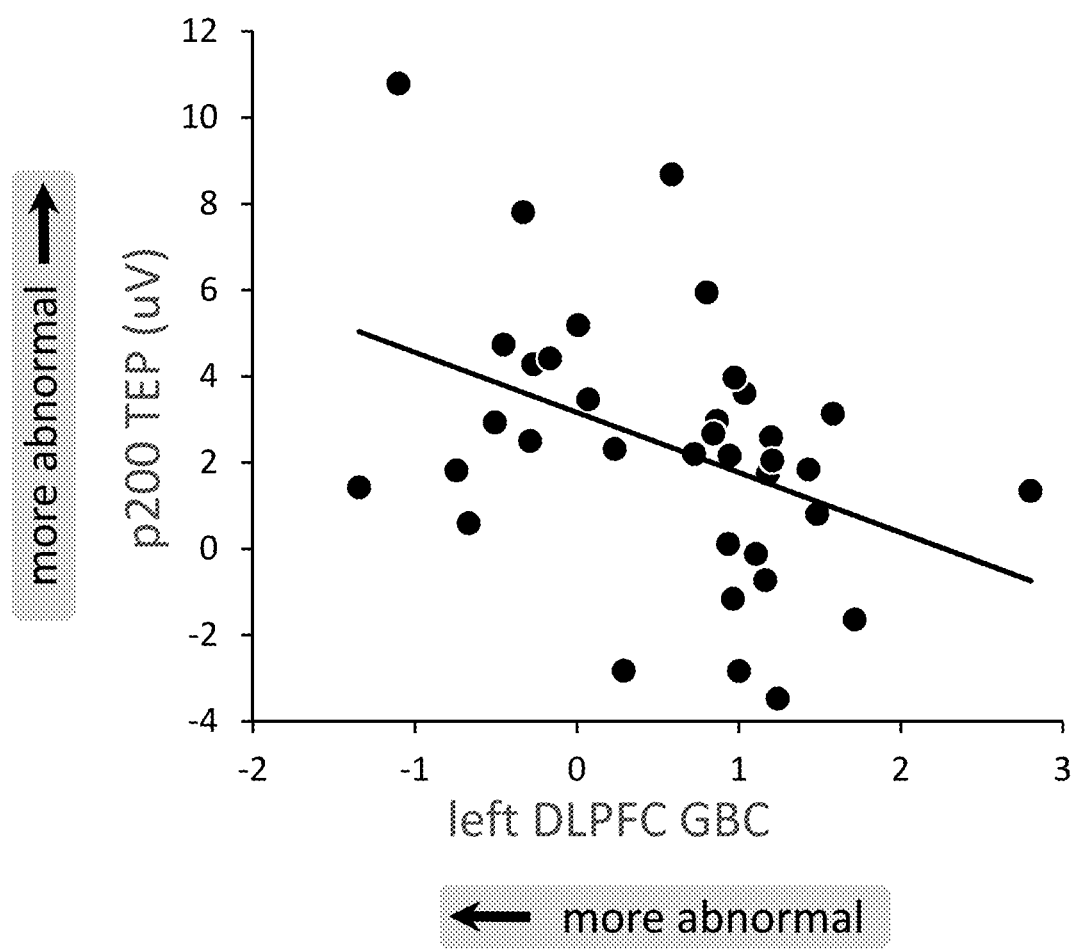
FIG. 19.

The data shown on FIGS. 17A, 17B, 18A, 18B and 19, which show the resting fMRI connectivity data and its relationship with TMS/EEG data, demonstrate that the more abnormal the brain region being targeted for treatment the better a subject (e.g. a patient) will do. This type of result can provide a good basis to access around which to adapt treatment. In the data shown in FIGS. 17A and 17B, the global connectivity of each voxel (3-D point) in the brain is measured. This measurement can look at how connected each voxel is with each other voxel in the brain. The finding may indicate that the more abnormal the global brain connectivity (GBC), which in this case means low GBC, the better the person can do. On FIG. 17A, there is an arbitrary breakdown into more or less abnormal (with abnormal being in reference to where controls are). Those with a greater abnormality (lower GBC) have a steeply declining symptom slope, while those with higher GBC fail to show response. On FIG. 17B, there is an image of the brain showing where across the whole cortex there is a relationship of baseline GBC to outcome, and it reveals a cluster just near the stimulation site. The graph on FIG. 18A demonstrates much the same indications as FIGS. 17A and 17B but shows not an arbitrary split on the median but rather a split by responders/non-responders. One of the findings from the data on FIG. 18A is that the result of treatment only in the responders was an increase (normalization) after treatment. FIG. 18B shows a correlation between the magnitude of the change in GBC across all patients and the change in their symptoms, which is consistent with the findings from the data of FIG. 18A, i.e. the more there was normalization of the GBC abnormality, the better the person did clinically. The data from FIG. 19 shows a correlation between the fMRI GBC finding and the TMS/EEG p200 finding, specifically that the greater the abnormality by fMRI, the greater the abnormality by TMS/EEG.

While preferred embodiments of the disclosures have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

CERTAIN EMBODIMENTS

Embodiment 1

A method for treating depression, the method comprising: administering a transcranial magnetic stimulation (TMS) therapy to a subject in need thereof; and measuring a TMS evoked response in said subject.

Embodiment 2

The method of Embodiment 1, wherein TMS provided in said TMS therapy is repetitive TMS (rTMS).

Embodiment 3

The method of Embodiment 1, wherein TMS provided in said TMS therapy is single pulse TMS (spTMS).

Embodiment 4

The method of Embodiment 1, wherein TMS provided in said TMS therapy is paired pulse TMS (ppTMS).

Embodiment 5

The method of Embodiment 4, wherein the ppTMS initial pulse precedes a paired pulse by 50-250 milliseconds (msecs).

Embodiment 6

The method of Embodiment 4 or 5, wherein the ppTMS is used to assess long-interval intracortical inhibition (LICI).

Embodiment 7

The method of any of Embodiments 1-6, wherein TMS provided in said TMS therapy is 1 Hz TMS, 3 Hz TMS, 5 Hz TMS, 7 Hz TMS, 10 Hz TMS, 15 Hz TMS, 20 Hz TMS, 25 Hz TMS, 30 Hz TMS or intermittent theta burst TMS.

Embodiment 8

The method of any of Embodiments 1-7, wherein the TMS therapy is administered to the left or right prefrontal cortices.

Embodiment 9

The method of any of Embodiments 1-8, wherein the TMS therapy is administered to the left dorsolateral prefrontal cortex (DLPFC), right DLPFC, dorsal cingulate, dorsomedial prefrontal cortex, frontopolar cortex, and/or ventrolateral prefrontal cortex.

Embodiment 10

The method of any of Embodiments 1-9, wherein the TMS evoked response is measured via electroencephalogram (EEG), Magnetoencephalography (MEG), Functional magnetic resonance imaging (fMRI), and/or Near-infrared spectroscopy (NIRS).

Embodiment 11

The method of Embodiment 10, wherein the TMS evoked response is measured via EEG concurrently with or immediately after said TMS therapy (TMS/EEG).

Embodiment 12

The method of Embodiment 11, wherein TMS provided in said TMS therapy is spTMS.

Embodiment 13

The method of Embodiment 11, where the method further comprises removing one or more artifacts from data measured via TMS/EEG.

Embodiment 14

The method of Embodiment 13, wherein said removing the one or more artifacts is done by using an automated artifact rejection algorithm.

Embodiment 15

The method of any of Embodiments 1-14, wherein the TMS evoked response is measured between 25-50 msecs, 100-150 msecs and 180-200 msecs.

Embodiment 16

The method of any of Embodiments 1-14, wherein the TMS evoked response is measured between 25-50 msecs (p30), 30-70 msecs (p60), 70-120 msecs (n100), 150-250 msecs (p200).

Embodiment 17

The method of any of Embodiments 1-16, wherein the TMS evoked response .is measured on the amplitude of oscillations at theta (5-8 Hz), alpha (8-12 Hz), beta (12-30 Hz), or gamma (30-60 Hz) within the first second after a TMS pulse.

Embodiment 18

The method of any of Embodiments 1-17, further comprising adapting a course of treatment according to variations in at least one factor of the TMS evoked response selected from the group consisting of a frequency of TMS, power of TMS, duration of TMS, a TMS wave form, a pattern of TMS, and a TMS site.

Embodiment 19

The method of Embodiment 18, wherein adapting a course of treatment comprises selection of a TMS site with a greater response to TMS. In certain embodiments, a subject (e.g. a patient) may be administered with TMS from a plurality of different TMS sites and the subject's response to each of the TMS sites may be measured. Among the plurality of TMS sites, one or more TMS sites can be selected as part of individualized or personalized treatment protocols for the subject when the subject's response to the specific TMS sites shows greater response compared to other TMS sites.

Embodiment 20

The method of Embodiment 18, wherein adapting a course of treatment comprises selection of a TMS protocol providing the greatest modulation of the TMS evoked response following a short course of rTMS. In some embodiments, a short course of rTMS may include, for example, rTMS for about 5-30 minutes. In certain embodiments, a subject (e.g. a patient) may be administered with a plurality of TMS treatments and the subject's response to each of the TMS treatments may be measured. Among the plurality of TMS treatments, a TMS treatment and the protocol thereof can be selected as an individualized or personalized treatment protocol for the subject when the subject's response to the specific TMS treatment shows the greatest response compared to other TMS treatments.

Embodiment 21

The method of Embodiment 18, wherein adapting a course of treatment comprises increasing a frequency of rTMS.

Embodiment 22

The method of Embodiment 18, wherein adapting a course of treatment comprises decreasing a frequency of rTMS by at least 5%, 10%, 25%, 30%, 50%, 75%, or even by 100% from an originally planned frequency of rTMS treatment or the frequency of rTMS that was previously administered to the subject.

Embodiment 23

The method of Embodiment 18, wherein adapting a course of treatment comprises increasing a power of rTMS by at least 5%, 10%, 25%, 30%, 50%, 75%, or even by 100% from an originally planned power of rTMS treatment or the power of rTMS that was previously administered to the subject.

Embodiment 24

The method of Embodiment 18, wherein adapting a course of treatment comprises decreasing a power of rTMS by at least 5%, 10%, 25%, 30%, 50%, 75%, or even by 100% from an originally planned frequency of rTMS treatment or the frequency of rTMS that was previously administered to the subject.

Embodiment 25

The method of Embodiment 18, wherein adapting a course of treatment comprises prolonging a treatment duration by at least 5%, 10%, 25%, 30%, 50%, 75%, or even by 100% from an originally planned duration of TMS treatment or the duration of TMS treatment that was previously administered to the subject.

Embodiment 26

The method of Embodiment 18, wherein adapting a course of treatment comprises decreasing a treatment duration by at least 5%, 10%, 25%, 30%, 50%, 75%, or even by 100% from an originally planned duration of TMS treatment or the duration of rTMS that was previously administered to the subject.

Embodiment 27

The method of Embodiment 18, wherein adapting a course of treatment comprises terminating rTMS treatment.

Embodiment 28

The method of Embodiment 18, wherein adapting a course of treatment is implemented according to a machine learning protocol.

Embodiment 29

The method of any of Embodiments 1-17, further comprising, prior to said administering the TMS therapy, measuring a brain activity of said subject, thereby obtaining a first data set of the brain activity data.

Embodiment 30

The method of Embodiment 29, further comprising, after said measuring the TMS evoked response, obtaining a second data set of the brain activity from the measured TMS evoked response.

Embodiment 31

The method of Embodiment 30, further comprising, determining a treatment protocol for said subject based on said first data set and said second data set.

Embodiment 32

The method of Embodiment 31, wherein said determining the treatment protocol comprises adapting a treatment protocol selected from the group consisting of a frequency of TMS, intensity of TMS, duration of TMS, a TMS wave form, a pattern of TMS, and a TMS site.

Embodiment 33

The method of Embodiment 32, wherein said TMS site comprises a site and/or an angle of a coil that is positioned on the head of the subject.

Embodiment 34

The method of Embodiment 33, wherein said adapting a treatment protocol comprises selection of a TMS site with a greater response to TMS. In certain embodiments, a subject (e.g. a patient) may be administered with TMS from a plurality of different TMS sites and the subject's response to each of the TMS sites may be measured. Among the plurality of TMS sites, one or more TMS sites can be selected as part of individualized or personalized treatment protocols for the subject when the subject's response to the specific TMS sites shows greater response compared to other TMS sites.

Embodiment 35

The method of Embodiment 33, wherein said adapting a treatment protocol comprises selection of a TMS protocol providing a substantial modulation of the TMS evoked response.

Embodiment 36

The method of Embodiment 33, wherein said adapting a treatment protocol comprises selection of a TMS protocol, which causes a substantial difference between said first data set and said second data set.

Embodiment 37

The method of Embodiment 33, wherein said adapting a treatment protocol comprises changing a TMS site.

Embodiment 38

The method of Embodiment 33, wherein said adapting a treatment protocol comprises changing a site and/or an angle of the coil from an originally planned site and/or angle of the coil or the site and/or angle of the coil that was previously located and treated to the subject.

Embodiment 39

The method of Embodiment 33, wherein said adapting a treatment protocol comprises increasing or decreasing a frequency of TMS negatively or positively by at least 5%, 10%, 25%, 30%, 50%, 75%, or even by 100% from an originally planned frequency of TMS treatment or the frequency of TMS that was previously administered to the subject.

Embodiment 40

The method of Embodiment 33, wherein said adapting a treatment protocol comprises increasing or decreasing intensity of TMS negatively or positively by at least 5%, 10%, 25%, 30%, 50%, 75%, or even by 100% from an originally planned intensity of TMS or the intensity of TMS that was previously administered to the subject.

Embodiment 41

The method of Embodiment 33, wherein said adapting a treatment protocol comprises prolonging or reducing TMS treatment duration negatively or positively by at least 5%, 10%, 25%, 30%, 50%, 75%, or even by 100% from an originally planned duration of TMS treatment or the duration of TMS treatment that was previously administered to the subject.

Embodiment 42

The method of Embodiment 33, wherein said adapting a treatment protocol comprises changing a TMS wave form from an originally planned waveform of TMS or the waveform of TMS that was previously administered to the subject.

Embodiment 43

The method of Embodiment 33, wherein said adapting a treatment protocol comprises changing a pattern of TMS from an originally planned pattern of TMS or the pattern of TMS that was previously administered to the subject.

Embodiment 44

The method of Embodiment 33, wherein said adapting a treatment protocol comprises terminating TMS treatment.

Embodiment 45

The method of Embodiment 33, wherein said adapting a treatment protocol is implemented according to a machine learning protocol.

Embodiment 46

The method of any of Embodiments 1-45, further comprising repeating the administering and measuring steps following a course of treatment.

Embodiment 47

The method of Embodiment 46, wherein repeating the administering and measuring steps is within a single day.

Embodiment 48

The method of Embodiment 47, wherein repeating the administering and measuring steps occurs within a 1-2 hours from the initial course of treatment.

Embodiment 49

The method of Embodiment 47, wherein repeating the administering and measuring steps occurs in real-time, responsive to a measured TMS evoked response.

Embodiment 50

The method of Embodiment 47, wherein repeating the administering and measuring steps occurs one or more weeks, one month, two months, three months, 6 months, or one year following a successfully complete course of treatment.

BIBLIOGRAPHY

Bliss, T. V. and G. L. Collingridge, A synaptic model of memory: long-term potentiation in the hippocampus. Nature, 1993. 361(6407): p. 31-9.
Hallett, M., Transcranial magnetic stimulation: a primer. Neuron, 2007. 55(2): p. 187-99.
Quartarone, A., H. R. Siebner, and J. C. Rothwell, Task-specific hand dystonia: can too much plasticity be bad for you? Trends Neurosci, 2006. 29(4): p. 192-9.
Ziemann, U. and H. R. Siebner, Modifying motor learning through gating and homeostatic metaplasticity. Brain Stimul, 2008. 1(1): p. 60-6.
Kaiser, R. H., et al., Large-Scale Network Dysfunction in Major Depressive Disorder: A Meta-analysis of Resting-State Functional Connectivity. JAMA Psychiatry, 2015. 72(6): p. 603-11.
Burt, T., S. H. Lisanby, and H. A. Sackeim, Neuropsychiatric applications of transcranial magnetic stimulation: a meta analysis. Int J Neuropsychopharmacol, 2002. 5(1): p. 73-103.
Holtzheimer, P. E., 3rd, J. Russo, and D. H. Avery, A meta-analysis of repetitive transcranial magnetic stimulation in the treatment of depression. Psychopharmacol Bull, 2001. 35(4): p. 149-69.
McNamara, B., et al., Transcranial magnetic stimulation for depression and other psychiatric disorders. Psychological medicine, 2001. 31(7): p. 1141-6.
George, M. S., et al., Daily left prefrontal transcranial magnetic stimulation therapy for major depressive disorder: a sham-controlled randomized trial. Arch Gen Psychiatry, 2010. 67(5): p. 507-16.
Janicak, P. G., et al., Repetitive transcranial magnetic stimulation versus electroconvulsive therapy for major depression: preliminary results of a randomized trial. Biological psychiatry, 2002. 51(8): p. 659-67.
O'Reardon, J. P., et al., Efficacy and safety of transcranial magnetic stimulation in the acute treatment of major depression: a multisite randomized controlled trial. Biological psychiatry, 2007. 62(11): p. 1208-16.
Eranti, S., et al., A randomized, controlled trial with 6-month follow-up of repetitive transcranial magnetic stimulation and electroconvulsive therapy for severe depression. Am J Psychiatry, 2007. 164(1): p. 73-81.
Grunhaus, L., et al., A randomized controlled comparison of electroconvulsive therapy and repetitive transcranial magnetic stimulation in severe and resistant nonpsychotic major depression. Biological psychiatry, 2003. 53(4): p. 324-31.
O'Connor, M., et al., Relative effects of repetitive transcranial magnetic stimulation and electroconvulsive therapy on mood and memory: a neurocognitive risk-benefit analysis. Cogn Behav Neurol, 2003. 16(2): p. 118-27.
George, M. S., J. J. Taylor, and B. Short, Treating the depressions with superficial brain stimulation methods. Handb Clin Neurol, 2013. 116: p. 399-413.
Lisanby, S. H., et al., Daily left prefrontal repetitive transcranial magnetic stimulation in the acute treatment of major depression: clinical predictors of outcome in a multisite, randomized controlled clinical trial. Neuropsychopharmacology: official publication of the American College of Neuropsychopharmacology, 2009. 34(2): p. 522-34.
Herwig, U., et al., Transcranial magnetic stimulation in therapy studies: examination of the reliability of "standard" coil positioning by neuronavigation. Biological psychiatry, 2001. 50(1): p. 58-61.
Hadley, D., et al., Safety, tolerability, and effectiveness of high doses of adjunctive daily left prefrontal repetitive transcranial magnetic stimulation for treatment-resistant depression in a clinical setting. The journal of ECT, 2011. 27(1): p. 18-25.
Privman, E., et al., Enhanced category tuning revealed by intracranial electroencephalograms in high-order human visual areas. J Neurosci, 2007. 27(23): p. 6234-42.
Keller, C. J., et al., Intrinsic functional architecture predicts electrically evoked responses in the human brain. Proceedings of the National Academy of Sciences of the United States of America, 2011. 108(25): p. 10308-13.
Keller, C. J., et al., Neurophysiological investigation of spontaneous correlated and anticorrelated fluctuations of the BOLD signal. J Neurosci, 2013. 33(15): p. 6333-42.
Keller, C. J., et al., Intrinsic functional architecture predicts electrically evoked responses in the human brain. Proc Natl Acad Sci USA, 2011. 108(25): p. 10308-13.
Matsumoto, R., et al., Functional connectivity in human cortical motor system: a cortico-cortical evoked potential study. Brain, 2007. 130(Pt 1): p. 181-97.
Matsumoto, R., et al., Functional connectivity in the human language system: a cortico-cortical evoked potential study. Brain, 2004. 127(Pt 10): p. 2316-30.
George, M. S., T. A. Ketter, and R. M. Post, Prefrontal cortex dysfunction in clinical depression. Depression, 1994. 2(59-72)
George, M. S., E. M. Wassermann, W. A. Williams, A. Callahan, T. A. Ketter, P. Basser, M. Hallett, and R. M. Post, Daily repetitive transcranial magnetic stimulation (rTMS) improves mood in depression. Neuroreport, 1995. 6(14): p. 1853-6
Glasser, M. F., T. S. Coalson, E. C. Robinson, C. D. Hacker, J. Harwell, E. Yacoub, K. Ugurbil, J. Andersson, C. F. Beckmann, M. Jenkinson, S. M. Smith, and D. C. Van Essen, A multi-modal parcellation of human cerebral cortex. Nature, 2016. 536(7615): p. 171-8
Ahdab, R., S. S. Ayache, P. Brugieres, C. Goujon, and J. P. Lefaucheur, Comparison of "standard" and "navigated" procedures of TMS coil positioning over motor, premotor and prefrontal targets in patients with chronic pain and depression. Neurophysiol Clin, 2010. 40(1): p. 27-36
Beam, W., J. J. Borckardt, S. T. Reeves, and M. S. George, An efficient and accurate new method for locating the F3 position for prefrontal TMS applications. Brain Stimul, 2009. 2(1): p. 50-4
O'Reardon, J. P., H. B. Solvason, P. G. Janicak, S. Sampson, K. E. Isenberg, Z. Nahas, W. M. McDonald, D. Avery, P. B. Fitzgerald, C. Loo, M. A. Demitrack, M. S. George, and H. A. Sackeim, Efficacy and safety of transcranial magnetic stimulation in the acute treatment of major depression: a multisite randomized controlled trial. Biol Psychiatry, 2007. 62(11): p. 1208-16

Carpenter, L. L., P. G. Janicak, S. T. Aaronson, T. Boyadjis, D. G. Brock, I. A. Cook, D. L. Dunner, K. Lanocha, H. B. Solvason, and M. A. Demitrack, Transcranial magnetic stimulation (TMS) for major depression: a multisite, naturalistic, observational study of acute treatment outcomes in clinical practice. Depress Anxiety, 2012. 29(7): p. 587-96

Gershon, A. A., P. N. Dannon, and L. Grunhaus, Transcranial magnetic stimulation in the treatment of depression. Am J Psychiatry, 2003. 160(5): p. 835-45

Herbsman, T., D. Avery, D. Ramsey, P. Holtzheimer, C. Wadjik, F. Hardaway, D. Haynor, M. S. George, and Z. Nahas, More lateral and anterior prefrontal coil location is associated with better repetitive transcranial magnetic stimulation antidepressant response. Biol Psychiatry, 2009. 66(5): p. 509-15

Fitzgerald, P. B., K. Hoy, S. McQueen, J. J. Maller, S. Herring, R. Segrave, M. Bailey, G. Been, J. Kulkarni, and Z. J. Daskalakis, A randomized trial of rTMS targeted with MRI based neuro-navigation in treatment-resistant depression. Neuropsychopharmacology, 2009. 34(5): p. 1255-62

Opitz, A., M. D. Fox, R. C. Craddock, S. Colcombe, and M. P. Milham, An integrated framework for targeting functional networks via transcranial magnetic stimulation. Neuroimage, 2016. 127: p. 86-96

Casarotto, S., L. J. Romero Lauro, V. Bellina, A. G. Casali, M. Rosanova, A. Pigorini, S. Defendi, M. Mariotti, and M. Massimini, EEG responses to TMS are sensitive to changes in the perturbation protocols and repeatable over time. PLoS One, 2010. 5(4): p. e10281

Koch, G., V. Ponzo, F. Di Lorenzo, C. Caltagirone, and D. Veniero, Hebbian and anti-Hebbian spike-timing-dependent plasticity of human cortico-cortical connections. J Neurosci, 2013. 33(23): p. 9725-33

Bakker, N., S. Shahab, P. Giacobbe, D. M. Blumberger, Z. J. Daskalakis, S. H. Kennedy, and J. Downar, rTMS of the dorsomedial prefrontal cortex for major depression: safety, tolerability, effectiveness, and outcome predictors for 10 Hz versus intermittent theta-burst stimulation. Brain Stimul, 2015. 8(2): p. 208-15

Noda, Y., W. K. Silverstein, M. S. Barr, F. Vila-Rodriguez, J. Downar, T. K. Rajji, P. B. Fitzgerald, B. H. Mulsant, S. N. Vigod, Z. J. Daskalakis, and D. M. Blumberger, Neurobiological mechanisms of repetitive transcranial magnetic stimulation of the dorsolateral prefrontal cortex in depression: a systematic review. Psychol Med, 2015. 45(16): p. 3411-32

Liston, C., A. C. Chen, B. D. Zebley, A. T. Drysdale, R. Gordon, B. Leuchter, H. U. Voss, B. J. Casey, A. Etkin, and M. J. Dubin, Default Mode Network Mechanisms of Transcranial Magnetic Stimulation in Depression. Biol Psychiatry, 2014

Fox, M. D., R. L. Buckner, M. P. White, M. D. Greicius, and A. Pascual-Leone, Efficacy of transcranial magnetic stimulation targets for depression is related to intrinsic functional connectivity with the subgenual cingulate. Biol Psychiatry, 2012. 72(7): p. 595-603

Kozyrev, V., U. T. Eysel, and D. Jancke, Voltage-sensitive dye imaging of transcranial magnetic stimulation-induced intracortical dynamics. Proc Natl Acad Sci USA, 2014. 111(37): p. 13553-8

Hoppenrath, K., W. Hartig, and K. Funke, Intermittent Theta-Burst Transcranial Magnetic Stimulation Alters Electrical Properties of Fast-Spiking Neocortical Interneurons in an Age-Dependent Fashion. Front Neural Circuits, 2016. 10: p. 22

Benali, A., J. Trippe, E. Weiler, A. Mix, E. Petrasch-Parwez, W. Girzalsky, U. T. Eysel, R. Erdmann, and K. Funke, Theta-burst transcranial magnetic stimulation alters cortical inhibition. J Neurosci, 2011. 31(4): p. 1193-203

Chung, S. W., N. C. Rogasch, K. E. Hoy, and P. B. Fitzgerald, Measuring Brain Stimulation Induced Changes in Cortical Properties Using TMS-EEG. Brain Stimul, 2015. 8(6): p. 1010-20

Hill, A. T., N. C. Rogasch, P. B. Fitzgerald, and K. E. Hoy, TMS-EEG: A window into the neurophysiological effects of transcranial electrical stimulation in non-motor brain regions. Neurosci Biobehav Rev, 2016. 64: p. 175-84

Rogasch, N. C. and P. B. Fitzgerald, Assessing cortical network properties using TMS-EEG. Hum Brain Mapp, 2013. 34(7): p. 1652-69

Valls-Sole, J., A. Pascual-Leone, E. M. Wassermann, and M. Hallett, Human motor evoked responses to paired transcranial magnetic stimuli. Electroencephalogr Clin Neurophysiol, 1992. 85(6): p. 355-64

Insel, T., B. Cuthbert, M. Garvey, R. Heinssen, D. S. Pine, K. Quinn, C. Sanislow, and P. Wang, Research domain criteria (RDoC): toward a new classification framework for research on mental disorders. Am J Psychiatry, 2010. 167(7): p. 748-51

Chen, A. C., D. J. Oathes, C. Chang, T. Bradley, Z. W. Zhou, L. M. Williams, G. H. Glover, K. Deisseroth, and A. Etkin, Causal interactions between fronto-parietal central executive and default-mode networks in humans. Proc Natl Acad Sci USA, 2013. 110(49): p. 19944-9

Daskalakis, Z. J., F. Farzan, M. S. Barr, J. J. Maller, R. Chen, and P. B. Fitzgerald, Long-interval cortical inhibition from the dorsolateral prefrontal cortex: a TMS-EEG study. Neuropsychopharmacology, 2008. 33(12): p. 2860-9

Fitzgerald, P. B., J. J. Maller, K. Hoy, F. Farzan, and Z. J. Daskalakis, GABA and cortical inhibition in motor and non-motor regions using combined TMS-EEG: a time analysis. Clin Neurophysiol, 2009. 120(9): p. 1706-10

Rogasch, N. C., R. H. Thomson, F. Farzan, B. M. Fitzgibbon, N. W. Bailey, J. C. Hernandez-Pavon, Z. J. Daskalakis, and P. B. Fitzgerald, Removing artefacts from TMS-EEG recordings using independent component analysis: importance for assessing prefrontal and motor cortex network properties. Neuroimage, 2014. 101: p. 425-39

Winkler, I., S. Haufe, and M. Tangermann, Automatic classification of artifactual ICA-components for artifact removal in EEG signals. Behav Brain Funct, 2011. 7: p. 30

Chung, S. W., K. E. Hoy, and P. B. Fitzgerald, Theta-burst stimulation: a new form of TMS treatment for depression? Depress Anxiety, 2015. 32(3): p. 182-92

Thut, G. and A. Pascual-Leone, A review of combined TMS-EEG studies to characterize lasting effects of repetitive TMS and assess their usefulness in cognitive and clinical neuroscience. Brain Topogr, 2010. 22(4): p. 219-32

Slotema, C. W., J. D. Blom, H. W. Hoek, and I. E. Sommer, Should we expand the toolbox of psychiatric treatment methods to include Repetitive Transcranial Magnetic Stimulation (rTMS)? A meta-analysis of the efficacy of rTMS in psychiatric disorders. J Clin Psychiatry, 2010. 71(7): p. 873-84

Chen, J., C. Zhou, B. Wu, Y. Wang, Q. Li, Y. Wei, D. Yang, J. Mu, D. Zhu, D. Zou, and P. Xie, Left versus right repetitive transcranial magnetic stimulation in treating major depression: a meta-analysis of randomised controlled trials. Psychiatry Res, 2013. 210(3): p. 1260-4

Berlim, M. T., F. Van den Eynde, and Z. Jeff Daskalakis, Clinically meaningful efficacy and acceptability of low-frequency repetitive transcranial magnetic stimulation (rTMS) for treating primary major depression: a meta-analysis of randomized, double-blind and sham-controlled trials. Neuropsychopharmacology, 2013. 38(4): p. 543-51

First, M. B., R. L. Spitzer, M. Gibbon, and J. B. W. Williams, Structured Clinical Interview for DSM-IV-TR Axis I Disorders, Research Version, Patient Edition. 2002, New York: Biometrics Research, New York State Psychiatric Institute Hamilton, M., A rating scale for depression. Journal of neurology, neurosurgery, and psychiatry, 1960. 23: p. 56-62

APA, Diagnostic and statistical manual of mental disorders. 4th ed 1994, Washington D. C.: American Psychiatric Press Chen, A. C. and A. Etkin, Hippocampal network connectivity and activation differentiates post-traumatic stress disorder from generalized anxiety disorder. Neuropsychopharmacology, 2013

Etkin, A., K. E. Prater, F. Hoeft, V. Menon, and A. F. Schatzberg, Failure of anterior cingulate activation and connectivity with the amygdala during implicit regulation of emotional processing in generalized anxiety disorder. Am J Psychiatry, 2010. 167(5): p. 545-54

Etkin, A., K. E. Prater, A. F. Schatzberg, V. Menon, and M. D. Greicius, Disrupted amygdalar subregion functional connectivity and evidence of a compensatory network in generalized anxiety disorder. Arch Gen Psychiatry, 2009. 66(12): p. 1361-72

Etkin, A. and A. F. Schatzberg, Common abnormalities and disorder-specific compensation during implicit regulation of emotional processing in generalized anxiety and major depressive disorders. The American journal of psychiatry, 2011. 168(9): p. 968-78

Kroenke, K., R. L. Spitzer, J. B. Williams, and B. Lowe, The Patient Health Questionnaire Somatic, Anxiety, and Depressive Symptom Scales: a systematic review. Gen Hosp Psychiatry, 2010. 32(4): p. 345-59

Blanchard, E. B., J. Jones-Alexander, T. C. Buckley, and C. A. Forneris, Psychometric properties of the PTSD Checklist (PCL). Behav Res Ther, 1996. 34(8): p. 669-73

Watson, D., K. Weber, J. S. Assenheimer, L. A. Clark, M. E. Strauss, and R. A. McCormick, Testing a tripartite model: I. Evaluating the convergent and discriminant validity of anxiety and depression symptom scales. J Abnorm Psychol, 1995. 104(1): p. 3-14

Watson, D., L. A. Clark, K. Weber, J. S. Assenheimer, M. E. Strauss, and R. A. McCormick, Testing a tripartite model: II. Exploring the symptom structure of anxiety and depression in student, adult, and patient samples. J Abnorm Psychol, 1995. 104(1): p. 15-25

Posner, K., G. K. Brown, B. Stanley, D. A. Brent, K. V. Yershova, M. A. Oquendo, G. W. Currier, G. A. Melvin, L. Greenhill, S. Shen, and J. J. Mann, The Columbia-Suicide Severity Rating Scale: initial validity and internal consistency findings from three multisite studies with adolescents and adults. Am J Psychiatry, 2011. 168(12): p. 1266-77

Bernstein, D. P. and L. Fink, Childhood Trauma Questionnaire: A retrospective self-report manual 1998, San Antonio, TX: The Psychological Corporation Skevington, S. M., M. Lotfy, and K. A. O'Connell, The World Health Organization's WHOQOL-BREF quality of life assessment: psychometric properties and results of the international field trial. A report from the WHOQOL group. Quality of life research: an international journal of quality of life aspects of treatment, care and rehabilitation, 2004. 13(2): p. 299-310

Fava, M., Diagnosis and definition of treatment-resistant depression. Biological psychiatry, 2003. 53(8): p. 649-59

Kim, D. H., E. Adalsteinsson, G. H. Glover, and D. M. Spielman, Regularized higher-order in vivo shimming. Magn Reson Med, 2002. 48(4): p. 715-22

Smith, S. M., Neuroimage, 2004. 23(S1): p. 208-219

Andersson, J. L., S. Skare, and J. Ashburner, How to correct susceptibility distortions in spin-echo echo-planar images: application to diffusion tensor imaging. Neuroimage, 2003. 20(2): p. 870-88

Holland, D., J. M. Kuperman, and A. M. Dale, Efficient correction of inhomogeneous static magnetic field-induced distortion in Echo Planar Imaging. Neuroimage, 2010. 50(1): p. 175-83

Feinberg, D. A. and K. Setsompop, Ultra-fast MRI of the human brain with simultaneous multi-slice imaging. J Magn Reson, 2013. 229: p. 90-100

Setsompop, K., B. A. Gagoski, J. R. Polimeni, T. Witzel, V. J. Wedeen, and L. L. Wald, Blipped-controlled aliasing in parallel imaging for simultaneous multislice echo planar imaging with reduced g-factor penalty. Magn Reson Med, 2012. 67(5): p. 1210-24

Ilmoniemi, R. J. and D. Kicic, Methodology for combined TMS and EEG. Brain Topogr, 2010. 22(4): p. 233-48

Friston, K. J., J. Ashburner, J. B. Poline, C. D. Frith, J. D. Heather, and R. S. Frackowiak, Spatial registration and normalization of images. Hum Brain Mapp, 1995. 2: p. 165-189

Glover, G. H., T. Q. Li, and D. Ress, Image-based method for retrospective correction of physiological motion effects in fMRI: RETROICOR. Magn Reson Med, 2000. 44(1): p. 162-7

Friston, K. J., A. P. Holmes, K. J. Worsley, J. B. Poline, C. D. Frith, and R. S. Frackowiak, Statistical parametric maps in functional imaging: a general linear approach. Hum Brain Mapp, 1995. 2: p. 189-210

Klein, A., J. Andersson, B. A. Ardekani, J. Ashburner, B. Avants, M. C. Chiang, G. E. Christensen, D. L. Collins, J. Gee, P. Hellier, J. H. Song, M. Jenkinson, C. Lepage, D. Rueckert, P. Thompson, T. Vercauteren, R. P. Woods, J. J. Mann, and R. V. Parsey, Evaluation of 14 nonlinear deformation algorithms applied to human brain MRI registration. Neuroimage, 2009. 46(3): p. 786-802

Cordes, D., V. M. Haughton, K. Arfanakis, J. D. Carew, P. A. Turski, C. H. Moritz, M. A. Quigley, and M. E. Meyerand, Frequencies contributing to functional connectivity in the cerebral cortex in "resting-state" data. AJNR Am J Neuroradiol, 2001. 22(7): p. 1326-33

Faul, F., E. Erdfelder, A. G. Lang, and A. Buchner, G*Power 3: a flexible statistical power analysis program for the social, behavioral, and biomedical sciences. Behav Res Methods, 2007. 39(2): p. 175-91

What is claimed is:

1. A method for treating depression, the method comprising:

measuring an electrical response of a brain of a subject having depression and detecting a presence of intracortical inhibition; and administering a transcranial magnetic stimulation (TMS) therapy to the subject having depression and intracortical inhibition, wherein the TMS therapy reduces the intracortical inhibition, thereby treating depression.

2. The method of claim 1, wherein the intracortical inhibition is in a left dorsolateral prefrontal cortex (dlPFC) of the subject and the TMS therapy is applied to the left dlPFC of the subject.

3. The method of claim 1, wherein the measuring provides a first data set of brain activity data, the method further comprising:
measuring a transcranial magnetic stimulation evoked response, thereby obtaining a second data set of brain activity data from a measured transcranial magnetic stimulation evoked response.

4. The method of claim 1, wherein the TMS therapy includes at least one of repetitive transcranial magnetic stimulation, single pulse transcranial magnetic stimulation, or paired pulse transcranial magnetic stimulation.

5. The method of claim 4, wherein a paired pulse transcranial magnetic stimulation initial pulse precedes a paired pulse by about 50 to about 250 milliseconds.

6. The method of claim 1, wherein the administering the TMS therapy includes: applying the transcranial magnetic stimulation to a plurality of sites for the subject;
measuring a transcranial magnetic stimulation evoked response for each of the plurality of sites; and
selecting at least one site of the plurality of sites for applying the TMS therapy based on the transcranial magnetic stimulation evoked response.

7. The method of claim 6, wherein the transcranial magnetic stimulation evoked response is measured via electroencephalogram concurrently with or immediately after the TMS therapy.

8. The method of claim 6, wherein the transcranial magnetic stimulation evoked response is measured via electroencephalogram, magnetoencephalography, functional magnetic resonance imaging, near-infrared spectroscopy, or a combination of two or more thereof.

9. The method of claim 1, wherein the transcranial magnetic stimulation provided in the TMS therapy is 1 Hz transcranial magnetic stimulation, 3 Hz transcranial magnetic stimulation, 5 Hz transcranial magnetic stimulation, 7 Hz transcranial magnetic stimulation, 10 Hz transcranial magnetic stimulation, 15 Hz transcranial magnetic stimulation, 20 Hz transcranial magnetic stimulation, 25 Hz transcranial magnetic stimulation, 30 Hz transcranial magnetic stimulation or intermittent theta burst transcranial magnetic stimulation.

10. The method of claim 1, wherein the TMS therapy is administered to a left dorsolateral prefrontal cortex, a right dorsolateral prefrontal cortex, a dorsal cingulate, a dorsomedial prefrontal cortex, a frontopolar cortex, a ventrolateral prefrontal cortex, or a combination of two or more thereof.

11. The method of claim 1, where the method further comprises: removing one or more artifacts from data measured via electroencephalogram.

12. The method of claim 11, wherein said removing the one or more artifacts is done by using an automated artifact rejection algorithm.

13. The method of claim 1, further comprising repeating the administering and measuring steps following a course of treatment.

14. The method of claim 13, wherein repeating the administering and the measuring steps occur in real-time, responsive to a measured transcranial magnetic stimulation evoked response; occurs from about 1 hour to about 2 hours after an initial course of treatment; or occurs following a successfully completed course of treatment.

15. The method of claim 1, wherein the measuring the electrical response further includes:
at least one of obtaining an electroencephalogram on the subject or performing functional magnetic resonance imaging on the subject.

16. The method of claim 1, wherein the TMS therapy comprises simulation at a suprathreshold intensity.

17. The method of claim 16, wherein the suprathreshold intensity is at about 120% of the subject's resting motor threshold.

18. The method of claim 1, wherein the method reduces p60 TMS-evoked potentials (TEP) and/or p200 TEP.

19. The method of claim 18, wherein a greater reduction in p60 TEP or in p200 TEP correlates with a greater reduction in a symptom of depression.

20. The method of claim 18, wherein the more abnormal p200 TEP a subject has prior to therapy, the greater a reduction in p200 TEP experienced following TMS therapy, wherein abnormal is relative to a non-depressed subject.

21. The method of claim 18, wherein the method reduces p200 TEP in a lateral prefrontal cortex and/or in a medial prefrontal cortex of the subject.

22. A method for treating depression, the method comprising:
performing electroencephalography on a subject having depression to determine at least one of a brain activity and a brain connectivity of the subject;
detecting a presence of long-interval intracortical inhibition; and
administering a transcranial magnetic stimulation (TMS) therapy to the subject in response to the electroencephalography indicating one long-interval intracortical inhibition, wherein the TMS therapy reduces the long-interval intracortical inhibition, thereby treating the depression.

* * * * *